US010378000B2

(12) United States Patent
Gladden et al.

(10) Patent No.: US 10,378,000 B2
(45) Date of Patent: Aug. 13, 2019

(54) IONIC LIQUID-TOLERANT CELLULASE ENZYMES

(71) Applicants: The Regents of the University of California, Oakland, CA (US); National Technology & Engineering Solutions of Sandia, LLC, Albuquerque, NM (US)

(72) Inventors: John Gladden, Alameda, CA (US); Joshua Park, Emeryville, CA (US); Steven Singer, Berkeley, CA (US); Blake Simmons, San Francisco, CA (US); Ken Sale, Livermore, CA (US)

(73) Assignees: National Technology & Engineering Solutions of Sandia, LLC, Albuquerque, NM (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/798,351

(22) Filed: Oct. 30, 2017

(65) Prior Publication Data

US 2018/0057805 A1 Mar. 1, 2018

Related U.S. Application Data

(62) Division of application No. 14/612,201, filed on Feb. 2, 2015, now Pat. No. 9,803,182.

(60) Provisional application No. 61/935,288, filed on Feb. 3, 2014.

(51) Int. Cl.
*C12N 9/42* (2006.01)
*C12P 19/02* (2006.01)
*C12P 19/14* (2006.01)

(52) U.S. Cl.
CPC ......... *C12N 9/2445* (2013.01); *C12N 9/2437* (2013.01); *C12P 19/02* (2013.01); *C12P 19/14* (2013.01); *C12Y 302/01004* (2013.01); *C12Y 302/01021* (2013.01)

(58) Field of Classification Search
None
See application file for complete search history.

(56) References Cited

PUBLICATIONS

Chen et al., "On the Formation of a Protic Ionic Liquid in Nature", Angew. Chem. Int. Ed. 53:11762-11765, 2014 (Year: 2014).*
Gladden et al., "Substrate Perturbation Alters the Glycoside Hydrolase Activities and Community Composition of Switchgrass-Adapted Bacterial Consortia", Biotechnol. Bioengineer. 109:1140-1145, 2012 (Year: 2012).*
U.S. Appl. No. 14/612,201, "Restriction Requirement," dated Nov. 4, 2015, 15 pages.
U.S. Appl. No. 14/612,201. Non-Final Office Action, dated May 4, 2016, 30 pages.
U.S. Appl. No. 14/612,201, "Final Office Action," dated Nov. 25, 2016, 36 pages.
U.S. Appl. No. 14/612,201, "Notice of Allowance," dated Jun. 27, 2017, 14 pages.
Benedetto, et al., "Room Temperature Ionic Liquids Meet Biomolecules: A Microscopic View of Structure and Dynamics," ACS Sustainable Chem. Eng. 4:392-412, 2016.
D'Haseseleer, et al., "Proteogenomic Analysis of a Thermophilic Bacterial Consortium Adapted to Deconstruct Switchgrass," *PLOS ONE* vol. 8, No. 7, pp. 1-11 (2013).
GenBank Accession No. WP_014065767, Jul. 2013, 1 page.
GenBank Accession No. ACJ68032, Nov. 2009, 1 page.
UniProt Accession No. D1CB40, Jan. 2013, 2 pages.
Gladden et al., "Glycoside Hydrolase Activities of Thermophilic Bacterial Consortia Adapted to Switchgrass," Appl. Environ. Microbiol. 77:5804-5812, 2011.
Gladden et al., "Discovery and characterization of ionic liquid-tolerant thermophilic cellulases from a switchgrass-adapted microbial community," Biotechnol. Biofuels 7:15, 2014, 12 pages.
Park et al., "A Thermophilic Ionic Liquid-Tolerant Cellulase Cocktail for the Production of Cellulosic Biofuels," PLoS One 7:e37010, 2012, 10 pages.

* cited by examiner

*Primary Examiner* — David Steadman
(74) *Attorney, Agent, or Firm* — Kilpatrick Townsend & Stockton LLP

(57) ABSTRACT

The present invention provides ionic liquid-tolerant cellulases and method of producing and using such cellulases. The cellulases of the invention are useful in saccharification reactions using ionic liquid treated biomass.

10 Claims, 2 Drawing Sheets

Specification includes a Sequence Listing.

IONIC LIQUID-TOLERANT CELLULASE ENZYMES

CROSS-REFERENCE TO RELATED APPLICATIONS

This application is a divisional application of U.S. application Ser. No. 14/612,201, filed Feb. 2, 2015, which claims priority benefit of U.S. provisional application No. 61/935,288, filed Feb. 3, 2014, each of which applications is herein incorporated by reference for all purposes.

STATEMENT AS TO RIGHTS TO INVENTIONS MADE UNDER FEDERALLY SPONSORED RESEARCH AND DEVELOPMENT

The invention was made with government support under Contract No. DE-AC02-05CH11231 awarded by the U.S. Department of Energy. The government has certain rights in the invention.

REFERENCE TO A "SEQUENCE LISTING" SUBMITTED AS AN ASCII TEXT FILE

This application includes a Sequence Listing as a text file named "SEQTXT_77429-1066487.txt" created on Oct. 30, 2017 and containing 127,909 bytes. The material contained in this text file is hereby incorporated by reference in its entirety for all purposes.

BACKGROUND OF THE INVENTION

With global energy demands rising rapidly, new technologies need to be developed that utilize new resources for transportation fuels. Lignocellulosic biomass is one promising resource, where an estimated one billion tons will be available annually by 2030 in the US alone. Lignocellulosic biomass is primarily composed of plant cell wall polysaccharides, such as cellulase and hemicelluloses, which together constitute 60-70% of the biomass by weight for potential energy crops such as switchgrass. These polymers are composed of hexose and pentose sugars that can be fermented into substitutes for gasoline, diesel and jet fuel, augmenting or displacing current petroleum-based sources of liquid transportation fuels. One of the challenges of using lignocellulosic biomass for production of biofuels is the recalcitrance of plant biomass to deconstruction, a property that necessitates some form of chemical or physical pretreatment to permit enzymes or chemicals to gain access to and hydrolyze the plant polymers into fermentable sugars.

Pretreating biomass with certain classes ILs, most notably those with imidazolium-based cations, can be more efficient and tunable than other existing forms of pretreatment, and technoeconomic analysis of this route suggests that there are potential routes to economically viability. However, cellulase cocktails derived from filamentous fungi are incompatible with ILs. These enzyme cocktails can be strongly inhibited by certain ILs, necessitating expensive and inefficient washing steps to remove residual IL from the biomass prior to addition of enzymes (e.g., Li et al., *Bioresource Technol* 101:4900-4906, 2010; Turner et al., *Green Chem* 5:443-447, 2003; Park et al, *PLoS One* 2012, 7:e37010, 2012; Gladden et al., *Appl Environ Microbiol* 77:5804-5812, 2011). One solution to this issue is to develop enzyme cocktails that are tolerant to ILs. It has been shown that certain thermophilic bacterial cellulase enzymes can tolerate high levels of these ILs, and in fact these enzymes have been used to develop an IL-tolerant cellulase cocktail called JTherm (e.g., Park et al., 2012, supra; Gladden et al, 2011, supra; Datta et al., *Green Chem* 12:338-345, 2010; Gladden et al., *Biotechnol Bioeng* 109:1140-1145, 2012; Zhang et al., *Green Chem* 13:2083-2090, 2011. It has been further demonstrated that JTherm can be used in a one-pot IL pretreatment and saccharification bioprocessing scheme that eliminates the need to wash the pretreated biomass with water, significantly reducing the number of process steps (e.g., Shi et al., *Green Chem* 15:2579-2589, 2013).

Recently, complex compost-derived microbial communities were cultivated on switchgrass under thermophilic conditions to enrich for organisms that produce mixtures of IL-tolerant cellulases and xylanases (Gladden et al., 2011, supra). The community was composed of several abundant bacterial populations related to *Thermus thermophilus, Rhodothermus marinus, Paenibacillus, Thermobacillus* and an uncultivated lineage in the Gemmatimonadetes phylum (D'Haeseleer et al., *PLoS ONE* 8:e68465, 2013). The glycoside hydrolases from this community were found to have high optimum temperatures (~80° C.) and tolerated relatively high levels of $[C_2mim][OAc]$ compared to commercial cellulase cocktails (>50% activity in the presence of 30% (v/v) $[C_2mim][OAc]$). Therefore, these communities provide a rich reservoir of potential enzyme targets to develop thermophilic and IL tolerant cellulase cocktails. To discover the genes that encode these IL- and thermo-tolerant enzymes, metagenomic and proteomic analysis was conducted on the community (Gladden et al., 2011, supra; D'Haeseleer et al. 2013, supra)

The present invention provides IL- and thermo-tolerant cellulase enzymes, including enzymes whose activities are stimulated in the presence of ILs, which can be used in saccharification reactions to obtain sugars from lignocellulosic biomass.

SUMMARY OF THE INVENTION

The invention provides ionic liquid-tolerant b-glucosidase and endoglucanase polypeptides and methods of making such peptide and employing them in saccharification reaction to obtain sugars from lignocellulosic biomass.

In one aspect, the invention provide an isolated ionic liquid-tolerant β-glucosidase having at least 70% identity, or at least 90% identity, or at least 95% identity, to an amino acid sequence of one of SEQ ID NOS:1-15; or to an amino acid sequence selected from the group consisting of SEQ ID NOS:2, 3, 4, 12, 14, and 15. In some embodiments, the β-glucosidase polypeptide comprises an amino acid sequence of one of SEQ ID NOS:1-15; or of SEQ ID NOS:2, 3, 4, 12, 14, or 15. In some aspects, the invention additionally provides a composition, such as a reaction mixture, comprising such a β-glucosidase polypeptide and an ionic liquid. In some embodiments, the ionic liquid has as an imidazolium cation. In some embodiments the ionic liquid is $[C_2mim][OAc]$. In some embodiments, the composition further comprises a lignocellulosic biomass. In some embodiments, the composition further comprises one or more additional enzymes, e.g., an endoglucanase, used in saccharification reactions and/or breaking down lignocellulosic biomass.

In a further aspect, the invention provides an isolated ionic liquid-tolerant endoglucanase having at least 70% identity, or at least 90% identity, or at least 95% identity, to an amino acid sequence of one of SEQ ID NOS:16-26; or to an amino acid sequence selected from the group consisting of SEQ ID NO:16, 17, 18, 19, 20, and 21; or to an amino acid sequence selected from the group consisting of SEQ ID NO:17, 18, and 21. In some embodiments, the endoglucanase comprises an amino acid sequence of one of SEQ ID NOS:16-26; or of SEQ ID NO:16, 17, 18, 19, 20, or 21; or of SEQ ID NO:17, 18, or 21. In some aspects, the invention additionally provides a composition comprising such an endoglucanase and an ionic liquid. In some embodiments, the ionic liquid has as an imidazolium cation. In some embodiments the ionic liquid is [C2mim][OAc]. In some embodiments, the composition further comprises a lignocellulosic biomass. In some embodiments, the composition further comprises one or more additional enzymes, e.g., an endoglucanase, used in saccharification reactions and/or breaking down lignocellulosic biomass.

In further aspects, the invention provides a recombinant host cell comprising a heterologous nucleic acid sequence encoding an ionic liquid-tolerant β-glucosidase or endoglucanase as described herein. In some embodiments, the recombinant host cell has the nucleic acid encoding the ionic liquid integrated into the genome of the microorganism. In some embodiments, the nucleic acid sequence is present on an autonomously replicating plasmid contained within the host cell. In some embodiments, the recombinant host cell is a bacterial host cell, e.g., such as *E. coli*, or a *Bacillus* sp. In some embodiments the recombinant host cell is a yeast host cell or a filamentous fungi host cell. In some embodiments, the recombinant host cell is *Aspergillus niger*.

In further aspects, the invention provides a method of producing an ionic liquid-tolerant β-glucosidase or endoglucanase as described herein, the method comprising culturing a recombinant host cell as described here under conditions in which the ionic liquid-tolerant β-glucosidase or endoglucanase is expressed. In some embodiment, the method further comprises isolating the ionic liquid-tolerant β-glucosidase or endoglucanase from the host cell or, if the polypeptide is secreted, from the culture media in which the host cell is grow.

In additional aspect, the invention provides a method of increasing the yield of soluble sugar from a biomass, the method comprising incubating biomass with a composition comprising an ionic liquid-tolerant β-glucosidase or endoglucanase as described herein in an enzymatic hydrolysis reaction. Such a reaction typically comprises biomass, such as lignocellulosic biomass that has been pretreated with ionic liquid.

The invention additionally provides a method of increasing the yield from a reaction in which soluble sugars are a source of carbon, the method comprising incubating biomass treated an ionic liquid with an ionic liquid-tolerant β-glucosidase or endoglucanase as described herein in a fermentation reaction.

Additional aspects of the invention are further described below.

DETAILED DESCRIPTION OF THE INVENTION

Definitions

Figures 1A, 1B, 1C, 1D:
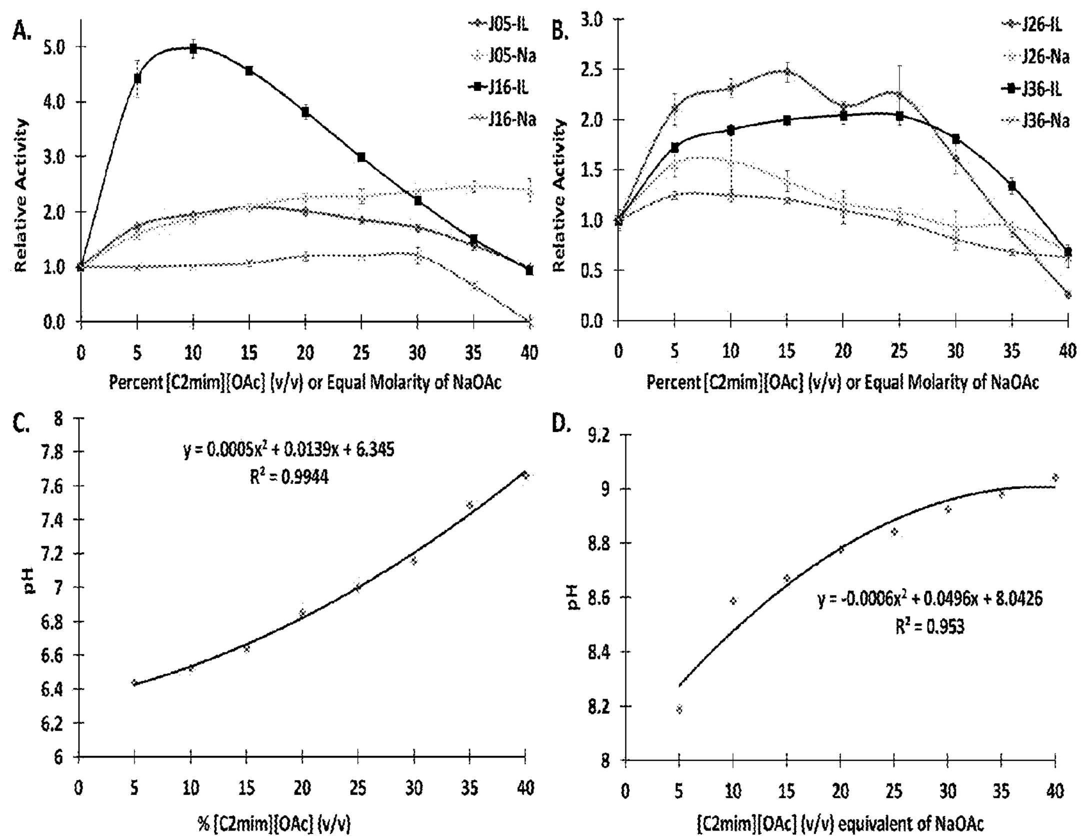
FIG. 1A-1D: Plot of enzyme activity in the presence of 0 to 40% [C2mim][OAc] or an equal molarity of NaOAc. Relative activity is based on activity in water (0% IL value). A) Two IL-tolerant Beta-glucosidases and B) two IL-tolerant endoglucanases were profiled. The pH was determined at each concentration of C) [$C_2$mim][OAc] and D) NaOAc. Error bars represent one standard deviation (they are too small to be visualized on C. and D.).

As used herein, the term “ionic liquid-tolerant β-glucosidase” refers to a β-glucosidase identified from a thermotolerant organism and fragments and variants thereof that retain activity, or have increased activity, in an ionic liquid such as [$C_2$mim][OAc]. The term encompasses variants and interspecies homologs of the specific polypeptides described herein. Beta-glucosidases are usually classified in the EC family 3.2.1.21 and catalyze the hydrolysis of terminal, non-reducing β-D-glucosyl residues with release of β-D-glucose. A nucleic acid that encodes an ionic liquid-tolerant protein refers to a gene, cDNA, pre-mRNA, mRNA, and the like, including nucleic acids encoding variants and interspecies homologs of the particular amino acid sequences described herein. Thus, in some embodiments, a gene encoding an ionic liquid-tolerant beta-glucosidase encodes a polypeptide having an amino acid sequence that has at least 40% amino acid sequence identity, or at least 45%, 50%, 55%, 60%, 65%, 70%, 75%, 80%, 85%, 90%, preferably 91%, 92%, 93%, 94%, 95%, 96%, 97%, 98% or 99% or greater amino acid sequence identity, preferably over a region of at least about 200, 300 or more amino acids, or over the length of the entire polypeptide, to an amino acid sequence of any one of SEQ ID NOS:1-15. In some embodiments, a gene encoding an ionic liquid-tolerant β-glucosidase encodes a polypeptide having an amino acid sequence that has at least 85% amino acid sequence identity to any one of SEQ ID NOS:1-15. In some embodiments, a gene encoding an ionic liquid-tolerant e β-glucosidase encodes a polypeptide having an amino acid sequence that has at least 90% amino acid sequence identity to any one of SEQ ID NOS:1-15. In some embodiments, a gene encoding an ionic liquid-tolerant β-glucosidase encodes a polypeptide having an amino acid sequence that has at least 95% amino acid sequence identity to any one of SEQ ID NOS:1-15.

As used herein, the term “ionic liquid-tolerant “endoglucosidase” refers to an endoclucanase identified from a thermotolerant organism and fragments and variants thereof that that retain activity, or have increased activity, in an ionic liquid such as [$C_2$mim][OAc]. The term encompasses variants and interspecies homologs of the specific polypeptides described herein. Endoglucanases are usually classified in the EC family 3.2.1.4 and catalyze the endohydrolysis of (1→4)-β-D-glucosidic linkages in cellulose, lichenin and cereal β-D-glucans. A nucleic acid that encodes an ionic liquid-tolerant protein refers to a gene, cDNA, pre-mRNA, mRNA, and the like, including nucleic acids encoding variants and interspecies homologs of the particular amino acid sequences described herein. Thus, in some embodiments, a gene encoding an ionic liquid-tolerant endoglucanase encodes a polypeptide having an amino acid sequence that has at least 40% amino acid sequence identity, or at least 45%, 50%, 55%, 60%, 65%, 70%, 75%, 80%, 85%, 90%, preferably 91%, 92%, 93%, 94%, 95%, 96%, 97%, 98% or 99% or greater amino acid sequence identity, preferably over a region of at least about 200, 300 or more amino acids, or over the length of the entire polypeptide, to an amino acid sequence of any one of SEQ ID NOS:16-26. In some embodiments, a gene encoding an ionic liquid-tolerant endoglucanase encodes a polypeptide having an amino acid sequence that has at least 85% amino acid sequence identity to any one of SEQ ID NOS:16-26. In some embodiments, a gene encoding an ionic liquid-tolerant endoglucanase encodes a polypeptide having an amino acid sequence that has at least 90% amino acid sequence identity to any one of SEQ ID NOS:16-26. In some embodiments, a gene encoding an ionic liquid-tolerant endoglucanase encodes a polypeptide having an amino acid sequence that has at least 95% amino acid sequence identity to any one of SEQ ID NOS: 16-26.

As used herein, the terms "retains activity in an ionic liquid" and "ionic liquid-tolerant" are used interchangeably to refer to a β-glucosidase or endoglucanase as described herein that retain at least 30%, typically at least 50%, at least 60%, at least 70%, at least 80%, at least 90%, or greater activity in the presence of an ionic liquid, such as [$C_2$mim][Oac], at a concentration of at least 5% (v/v) in comparison to a control reaction where the ionic liquid is absent. Typically, the activity is assessed at a temperature between 45 and 95° C. at a pH between 4 and 8 for an incubation period of from 15 minutes to an hour, but can be over an hour, e.g., 2, 3, 4, 5, 6, 7, 8, 9, 10, 11, 12, 13, 14, 15, or 16 hours, or up to 24 hours, or longer.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 40%, 45%, or 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are illustrative conservative substitutions for one another. 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety)

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide of the invention protein operably linked to a promoter, e.g., its native promoter, where the expression cassette is introduced into a heterologous microorganism. In some embodiments, an expression cassette comprises a polynucleotide sequence encoding a polypeptide of the invention where the polynucleotide that is targeted to a position in the genome of a microorganism such that expression of the polynucleotide sequence is driven by a promoter that is present in the microorganism.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used herein and in the appended claims, the singular "a", "an" and "the" include the plural reference unless the context clearly dictates otherwise. Thus, for example, reference to a "host cell" includes a plurality of such host cells.

I. Introduction

Ionic liquids are used to pretreat biomass to improve the yield of soluble sugars from downstream reactions such as enzymatic hydrolysis. This invention provides cellulase polypeptides, in particular β-glucosidase and endoglucanase polypeptides, that are tolerant to ionic liquids, methods of producing such cellulases, and methods employing the cellulases of the invention in saccharification reactions that employ lignocellulosic biomass as an initial substrate.

An ionic liquid-tolerant β-glucosidase of the invention has an amino acid sequence as set forth in any one of SEQ ID NOS:1-15, or is a variant or active fragment thereof that has substantial identity to the amino acid sequence. In some embodiments, the variant has at least 90%, or at least 95% identity, to one of the amino acid sequences of any one of SEQ ID NOS:1-15. In some embodiments, the variant has an amino acid sequence of any one of SEQ ID NOS:1-15.

An ionic liquid-tolerant endoglucanase of the invention has an amino acid sequence as set forth in any one of SEQ ID NOS:16-26, or is a variant or active fragment thereof that has substantial identity to the amino acid sequence. In some embodiments, the variant has at least 90%, or at least 95% identity, to one of the amino acid sequences of any one of SEQ ID NOS:16-26. An ionic liquid-tolerant endoglucanase of the invention often has an amino acid sequence as set forth in any one of SEQ ID NOS:16-21, or is a variant or active fragment thereof that has substantial identity to the amino acid sequence. In some embodiments, the variant has at least 90% identity, or at least 95% identity, to any one of SEQ ID NOS:16-21.

Ionic-Liquid Tolerant β-Glucosidase and Endoglucanase Polypeptide and Nucleic Acid Sequences The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009, supplements through 2012).

β-Glucosidases of the Invention

Ionic liquid-tolerant nucleic acid and polypeptide sequences suitable of the invention include nucleic acid sequences that encode a polypeptide of any one of SEQ ID NOs:1-15, or variants or fragments thereof that have β-glucosidase activity. In some embodiments, a variant typically has at least 60%, often at least 70%, or at least 75%, 80%, 85%, or 90% identity to one of SEQ ID NOs. 1, 2, 3, 4, 5, 6, 7, 8, 9, 10, 11, 12, 13 or 15. In some embodiments, a variant typically has at least 60%, often at least 70%, or at least 75%, 80%, 85%, or 90% identity to one of SEQ ID NOs. 2, 3, 4, 12, 14, or 15.

In identifying a variant of a an illustrative β-glucosidase of any one of SEQ ID NOS:1 to 15 as described herein, one of skill can identify residues likely to be tolerant to substitution based on the known structure and availability of other β-glucosidase sequences. For example, one of skill can obtain or identify a β-glucosidase variant for use in the invention by using the sequence alignments to the illustrative sequences provided to identify residues within the conserved sequences that would be expected to retain function as well as residues outside of the conserved regions that would be tolerant to substitution.

In some embodiments, a nucleic acid that encodes an ionic liquid-tolerant β-glucosidase polypeptide of the invention may comprise a polynucleotide sequence encoding a signal sequence. For example, in some embodiments, it may be desirable to employ a signal sequence from the host cell into which the nucleic acid encoding the polypeptide will be introduced.

Tolerance to ionic liquids can be assessed using known assays. For example, a gene encoding a variant of an ionic liquid-tolerant β-glucosidase of one of SEQ ID NOS:1-15 can be assessed for activity in the presence of an ionic liquid compared to the activity in the absence of ionic liquid. In typical embodiments, activity in the presence of the ionic liquid, e.g., 5% weight volume [$C_2$mim]OAc, is at least 50%, typically at least 80%, or greater than the activity in a control enzyme assay that does not include the ionic liquid. In some embodiments, the activity assay is conducted at a temperature above 40 degrees centigrade. Illustrative assays to determine activity of variants of an illustrative β-glucosidase polypeptide of any one of SEQ ID NOS:1 to 15 are typically performed at a temperature of 10 degrees below the $T_{opt}$ shown for the enzyme in Table 3

In some embodiments, the amount of ionic liquid employed in testing is in the range of from about 1% to about to about 20% IL, e.g., about 1%, 2%, 3%, 4%, 5%, 6%, 7%, 8%, 9%, 10%, or 15% or 20%, added to the enzyme assay reactions. In some embodiments, the amount of ionic liquid employed in testing is at least 5% (v/v) in the reaction. In some embodiments, the ionic liquid is [$C_2$mim][OAc].

In some embodiments, the assay for β-glucosidase activity is conducted at a pH in the range between 4 and 8. One of skill understands that the pH will typically depend on the concentration of ionic liquid. In some embodiments, the activity assay is conducted at a pH of from about 5 to about 7.5. For example, in some embodiments, the activity assay is conducted at a pH of about 5.5, about 6.0, about 6.5, about 7.0, or about 7.5. In some embodiments, a variant is identified by testing activity in 5% (v/v) [$C_2$mim]OAc], which results in a pH of about 6.4.

The following is an example of an assay using 4-nitrophenyl-β-D-gluccopyranoside as a substrate (see, e.g., the Example section). Up to 20 μL of lysate from a cell expressing the protein is employed in a reaction volume of 100 μL using 5 mM pNPG final concentration in a reaction that has 5% (v/v) [$C_2$mim][Oac]. The reaction is performed at about ~10° C. below the optimal temperature of the enzyme as shown in Table 3 for a timer period of from 15 minutes to an hour, e.g., 30 minutes.

One of skill understands that a β-glucosidase of the invention may also exhibit activity towards other substrates. For example, a β-glucosidase of the invention may exhibit Beta-xylosidase or cellobiohydrolase activity.

Endoglucanase of the Invention

In some embodiments, an ionic liquid-tolerant nucleic acid and polypeptide sequence of the invention encodes a polypeptide of any one of SEQ ID NOs:16-26, or a variant or fragment thereof having endoglucanase activity. In some embodiments, a variant has at least 60%, often at least 70%, or at least 75%, at least 80%, at least 85%, at least 90%, or at least 95% identity, or greater, to one of SEQ ID NOs. 16, 17, 18, 19, 20, 21, 22, 23, 24, 25, or 26. In some embodiments, the variant has at least 60%, often at least 70%, or at least 75%, at least 80%, at least 85%, at least 90%, or at least 95% identity, or greater, to one of SEQ ID NOs. 16, 17, 18, 19, 20, or 21. In some embodiments, the variant has at least 60%, often at least 70%, or at least 75%, at least 80%, at least 85%, at least 90%, or at least 95% identity, or greater, identity to one of SEQ ID NOs. 17, 19, or 21.

In identifying a variant of an illustrative endoglucanase of any one of SEQ ID NOS:16 to 26 as described herein, one of skill can identify residues likely to be tolerant to substitution based on the known structure and availability of other endoglucanase sequences. For example, one of skill can obtain or identify an endoglucanase variant for use in the invention by using the sequence alignments to the illustrative sequences provided to identify residues within the conserved sequences that would be expected to retain function as well as residues outside of the conserved regions that would be tolerant to substitution.

In some embodiments, a nucleic acid that encodes an ionic liquid-tolerant endoglucanase polypeptide of the invention may comprise a polynucleotide sequence encoding a signal sequence. For example, in some embodiments, it may be desirable to employ a signal sequence from the host cell into which the nucleic acid encoding the polypeptide will be introduced.

Tolerance to ionic liquids can be assessed using known assays. For example, a gene encoding a variant of an ionic liquid-tolerant endoglucanase of one of SEQ ID NOS:16-26 can be assessed for activity in the presence of an ionic liquid compared to the activity in the absence of ionic liquid. In typical embodiments, activity in the presence of the ionic liquid, e.g., 5% weight volume [$C_2$mim]OAc, is at least 50%, typically at least 80%, or greater than the activity in a control enzyme assay that does not include the ionic liquid. In some embodiments, the activity assay is conducted at a temperature above 40 degrees centigrade. Illustrative assays to determine activity of variants of an illustrative endoglucanase polypeptide of any one of SEQ ID NOS:16-26 are typically performed at a temperature of 10 degrees below the $T_{opt}$ shown for the enzyme in Table 3.

In some embodiments, the amount of ionic liquid employed in testing is in the range of from about 1% to about to about 20% IL, e.g., about 1%, 2%, 3%, 4%, 5%, 6%, 7%, 8%, 9%, 10%, or 15% or 20%, added to the enzyme assay reactions. In some embodiments, the amount of ionic liquid employed in testing is at least 5% (v/v) in the reaction. In some embodiments, the ionic liquid is [$C_2$mim][OAc].

In some embodiments, the assay for endoglucanase activity is conducted at a pH in the range between 4 and 8. One of skill understands that the pH will typically depend on the concentration of ionic liquid. In some embodiments, the activity assay is conducted at a pH of from about 5 to about 7.5. For example, in some embodiments, the activity assay is conducted at a pH of about 5.5, about 6.0, about 6.5, about 7.0, or about 7.5. In some embodiments, a variant is identified by testing activity in 5% (v/v) [$C_2$mim]OAc], which results in a pH of about 6.4.

The following is an example of an assay using carboxymethyl cellulose as a substrate (see, e.g., the Example section). Up to 20 μL of lysate from a cell expressing the protein is employed in a reaction volume of 100 μL using 15 carboxymethyl cellulose final concentration in a reaction that has 5% (v/v) [$C_2$mim][Oac]. The reaction is performed at about ~10° C. below the optimal temperature of the enzyme as shown in Table 3 for a time period of from 15 minutes to an hour, e.g., 30 minutes.

One of skill understands that endoglucanase of the invention may also exhibit activity towards other substrates. For example, an endoglucanase of the invention may exhibit endoxylanase activity.

Nucleic Acids Encoding an Ionic Liquid-Tolerant Polypeptide

Isolation or generation of polynucleotide sequences to express an ionic liquid-tolerant beta glucosidase or endoglucanase of the invention can be accomplished by any number of techniques well known in the art. In some embodiments, oligonucleotide probes based on the sequences disclosed herein can be used to identify the desired polynucleotide in a cDNA or genomic DNA library from a desired bacterial species. Probes may be used to hybridize with genomic DNA or cDNA sequences to isolate homologous genes in the same or different bacterial species.

Alternatively, the nucleic acids of interest can be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying a gene that encodes an ionic liquid-tolerant polypeptide of the invention from bacterial cells, such as thermotolerant bacterial cells, can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990).

Nucleic acid sequences for use in the invention includes genes and gene products identified and characterized by techniques such as hybridization and/or sequence analysis using exemplary nucleic acid sequences, e.g., any one of SEQ ID NOS:1 to 26.

Nucleic acid sequences encoding an ionic liquid-tolerant enzyme of the invention may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See, e.g., See e.g., Henaut and Danchin in "*Escherichia coli* and *Salmonella*," Neidhardt, et al. Eds., ASM Pres, Washington D.C. (1996), pp. 2047-2066; Nucleic Acids Res. 20:2111-2118; Nakamura et al., 2000, Nucl. Acids Res. 28:292.

Preparation of Recombinant Vectors

To use isolated sequences in the above techniques, recombinant DNA vectors suitable for transformation of host cells are prepared. Preparation of recombinant vectors is well known in the art. For example, a DNA sequence encoding an ionic liquid-tolerant β-glucosidase or endoglucanase of the invention can be combined with transcriptional and other regulatory sequences that direct the transcription of the sequence from the gene in the intended cells. In some embodiments, an expression vector that comprises an expression cassette that comprises the gene further comprises a promoter operably linked to the gene. Such a promoter can be a promoter from the native gene that encodes the ionic liquid-tolerant gene or can be a heterologous promoter. In other embodiments, a promoter and/or other regulatory elements that direct transcription of the gene are endogenous to the microorganism and an expression cassette comprising the gene encoding the ionic liquid-tolerant β-glucosidase or endoglucanase is introduced, e.g., by homologous recombination, such that the heterologous gene is operably linked to an endogenous promoter and is expression driven by the endogenous promoter.

Expression of the gene encoding the ionic liquid-tolerant β-glucosidase or endoglucanase can be controlled by a number of regulatory sequences including promoters, which may be either constitutive or inducible; and, optionally, repressor sequences. Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25) and tryptophan pormoter. Further promoters are described in "Useful proteins from recombinant bacteria" in Scientific American, 1980, 242: 74-94; and in Sambrook et al., 1989, supra.

In some embodiments, the ionic liquid-tolerant β-glucosidase or endoglucanase may be expressed in a fungal host cell. Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from the gene encoding neutral alpha-amylase in *Aspergillus niger* In which the untranslated leader has been replaced by an untranslated leader from the gene encoding triose phosphate isomerase in *Aspergillus nidulans*); and mutant, truncated, and hybrid promoters thereof.

Suitable promoters of use in a yeast host cell include promoters obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

Alternatively, an ionic liquid-tolerant β-glucosidase or endoglucanase of the invention may be produced in other expression systems, including insect, plant or mammalian expression systems. Such systems are well known in the art.

An expression vector may also comprise additional sequences that influence expression of a gene encoding an ionic liquid-tolerant β-glucosidase or endoglucanase of the invention. Such sequences include enhancer sequences or other sequences such as transcription termination sequences, and the like.

A vector expressing a nucleic acid encoding an ionic liquid-tolerant β-glucosidase or endoglucanase in accordance with the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated.

An expression vector of the invention preferably contains one or more selectable markers which permit easy selection of transformed hosts. For example, an expression vector my comprise a gene that confers antibiotic resistance (e.g., ampicillin, kanamycin, chloramphenicol or tetracycline resistance) to the recombinant host organism, e.g., a bacterial cell such as *E. coli*, that comprises the vector.

Suitable markers for other microbial host cells, such as yeast host cell are also well known and include, for example, ADE2, HIS3, LEU2, LYS2, MET3, TRP1, and URA3. Selectable markers for use in a filamentous fungal host include, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Markers for use in *Aspergillus* include the amdS and pyrG genes of *Aspergillus nidulans* ox *Aspergillus oryzae* and the bar gene of *Streptomyces hygroscopicus*. Markers for use in *Trichoderma* include bar and amdS.

An expression vector may additionally contain an element(s) that permits integration of the vector into the host's genome. In some embodiments, the expression vector may contain an element that permits autonomous replication of the vector in the cell independent of the genome.

Although any suitable expression vector may be used to incorporate the desired sequences, readily available bacterial expression vectors include, without limitation: plasmids, such as pSC1O1, pBR322, pBBR1MCS-3, pUR, pEX, pMR1OO, pCR4, pBAD24, pUC19; bacteriophages, such as M1 3 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

Expression vectors of the invention may be introduced into the host cell using any number of well-known methods, including calcium phosphate transfection, DEAE-Dextran mediated transfection, electroporation, injection, plant cell transformation techniques such as Agrobacterium mediated transformation, or any other method known in the art.

Host Cells

Any number of microorganism can be transformed with an expression vector comprising a gene encoding an ionic liquid-tolerant polypeptide in accordance with the invention. In some embodiments, the host cell is prokaryotic, such bacterial host cells. Examples of bacterial host cells include, without limitation, species assigned to the *Escherichia, Enterobacter, Azotobacter, Erwinia, Bacillus, Clostridium, Enterococcus, Lactobacillus, Lactococcu, Oceanobaciilus, Pseudomonas, Klebsiella, Proteus, Salmonella, Serratia, Shigella, Staphococcus, Strpeotcoccus, Streptomyces, Rhizobia, Vitreoscilla, Synechococcus, Synechocystis*, and *Paracoccus* taxonomical classes. In some embodiments, the prokaryotic host cells are *E. coli, Bacillus* sp. such as *Bacillus subtilis*. In some embodiments, the host cells are cyanobacteria.

In some embodiments, the host cell is a yeast. Examples of yeast host cells include *Candida, Hansenula, Kluyveromyces, Pichia, Saccharomyces, Schizosaccharomyces*, or *Yarrowia* host cells. In some embodiments, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In some embodiments, the yeast host cell is a *Kluyveromyces lactis* cell. In another embodiment, the yeast host cell is a *Yarrowia lipolytica* cell.

In other embodiments, the host cell is a filamentous fungal cell. In some embodiments, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Malbranchea, Mucor, Myceliophthora, Neocallimastix, Neurospora, Paecilomyces, Penicillium, Phanero-*

*chaete, Phlebia, Piromyces, Pleurotus, Schizophyllum, Talaromyces, Thermoascus, Thielavia, Tolypocladium, Trametes*, or *Trichoderma* cell. For example, a filamentous fungal host cell may be an *Aspergillus awamori, Aspergillus fumigatus, Aspergillus foetidus, Aspergillus japonicus, Aspergillus nidulans, Aspergillus niger* or *Aspergillus oryzae* cell. In other embodiments, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In further embodiments, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Malbranchea cinnamomea, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma Iongibrachiatum, Trichoderma reesei*, or *Trichoderma viride* cell. In some embodiments, the filamentous fungal host cell is *Ustilago maydis.*

In additional embodiments, the host cell may be a plant cell, insect cell, mammalian, avian, or other host cell.

The host cells of the present invention may be genetically modified in that recombinant nucleic acids have been introduced into the host cells, and as such the genetically modified host cells do not occur in nature. The suitable host cell is one capable of expressing one or more nucleic acid constructs encoding one or more proteins for different functions.

In some embodiments, the host cell naturally produces any of the proteins encoded by the polynucleotides of the invention. The genes encoding the desired proteins may be heterologous to the host cell or these genes may be endogenous to the host cell but are operatively linked to heterologous promoters and/or control regions which result in the higher expression of the gene(s) in the host cell. In other embodiments, the host cell does not naturally produce the desired proteins, and comprises heterologous nucleic acid constructs capable of expressing one or more genes necessary for producing those molecules.

Methods of Using an Ionic Liquid-Tolerant β-Glucosidase or Endoglucanase

An ionic liquid-tolerant β-glucosidase or endoglucanase of the invention may be used in a saccharification reaction or fermentation reaction to produces sugars. In typical embodiments, the enzyme is employed in a reaction mixture containing ionic liquids, biomass and other enzymes that break down the biomass. Biomass that is treated with an IL include, but is not limited to, a cellulose biomass, a hemicellulose biomass, a lignocellulose biomass and mixtures thereof. In some embodiments, the biomass is a lignocellulose biomass.

In practicing the invention a biomass, such as a lignocellulosic biomass, is typically pretreated with an ionic liquid and a β-glucosidase and/or endoglucanase of the invention is added following pretreatment. The enzyme may be added directly to the reaction. In some embodiments, pre-treated biomass may be washed prior to the addition of enzyme.

Examples of ILs suitable for treatment of the biomass and for the hydrolysis of cellulose by cellulases include, but are not limited to 1-ethyl-3-methylimidazolium acetate (EMIM Acetate), 1-ethyl-3-methylimidazolium chloride (EMIM CI or ([$C_2$mim]Cl), 1-ethyl-3-methylimidazolium hydrogensulfate (EMIM $HOSO_3$), 1-ethyl-3-methylimidazolium methylsulfate (EMIM $MeOSO_3$), 1-ethyl-3-methylimidazolium ethyl sulfate (EMIM $EtOSO_3$), 1-ethyl-3-methylimidazolium methanesulfonate (EMIM $MeSO_3$), 1-ethyl-3-methylimidazolium tetrachloroaluminate (EMIM AICI4), 1-ethyl-3-methylimidazolium thiocyanate (EMIM SCN), 1-butyl-3-methylimidazolium acetate (BMIM Acetate), 1-butyl-3-methylimidazolium chloride (BMIM CI), 1-butyl-3-methylimidazolium hydrogensulfate (BMIM $HOSO_3$), 1-butyl-3-methylimidazolium methanesulfonate (BMIM $MeSO_3$), 1-butyl-3-methylimidazolium methylsulfate (BMIM $MeOSO_3$), 1-butyl-3-methylimidazolium tetrachloroaluminate (BMIM AICI4), 1-butyl-3-methylimidazolium thiocyanate (BMIM SCN), 1-ethyl-2,3-dimethylimidazolium ethyl sulfate (EDIM $EtOSO_3$), Tris(2-hydroxyethyl) methylammonium methylsulfate (MTEOA $MeOSO_3$), 1-methylimidazolium chloride (MIM CI), 1-methylimidazolium hydrogensulfate (MIM $HOSO_3$), 1,2,4-trimethylpyrazolium methyl sulfate, tributylmethylammonium methylsulfate, choline acetate, choline salicylate, and the like. The ionic liquid can comprises one or a mixture of the compounds. In some embodiments, the ionic liquid has an imidazolium cation. Additional suitable ILs are taught in U.S. Pat. No. 6,177,575. It will be appreciated by those of skill in the art that others ILs that will be useful in the process of the present invention are currently being developed or will be developed in the future, and the present invention contemplates their future use.

The biomass, e.g., the lignocellulose biomass, can be hydrolyzed enzymatically to break down, for example, hemicellulose and/or cellulose, into sugars. Typically, the biomass undergoing treatment that has been treated with, or is concurrently treated with, an ionic liquid-tolerant β-glucosidase or endoglucanase of the invention is subjected to the action of multiple enzyme activities. In some embodiments, the biomass reaction comprises an ionic liquid-tolerant β-glucosidase and/or endoglucanase, and a cellobiohydrolase, and one or more other enzhymes such as a glucano-hydrolase, a protease, a pectinase, a xylanase, a lyase, a ferulic acid esterase, and a mannanase.

The present invention will be described in greater detail by way of specific examples. The following examples are offered for illustrative purposes, and are not intended to limit the invention in any manner. Those of skill in the art will readily recognize a variety of noncritical parameters, which can be changed or modified to yield essentially the same results.

EXAMPLES

Example 1. Identification of Ionic Liquid-Tolerant Cellulases

Identification of Cellulases in a Switchgrass-Adapted Metagenome

The metagenome of a thermophilic switchgrass-degrading bacterial community was curated for genes with cellulase-related annotations or homology to sequences for cellulase enzymes deposited in the CAZy database (at the cazy.org www website) including β-glucosidases (BG), cellobiohydrolases (CBH), and endoglucanases (Endo). A total of nineteen predicted BGs, two CBHs, and sixteen Endos were identified that appeared to be complete ORFs (Table 1; see methods). The top BLASTP hit for each identified cellulase is indicated in Table 1, including the maximum identity and source organism of the top hit in GenBank. Many of the ORFs are homologous to those found in isolates that cluster with abundant community members, such as *Rhodothermus marinus, Paenibacillus, Thermobacillus* and *Gemmatimonadetes*. Many of the ORFs fall into sequence bins assigned to these organisms in the metagenome that are consistent with the phylogenetic affiliation predicted by the BLASTP search (Table 1, and D'Haeseleer et. al., 2013, supra). Several of the ORFs in Table 1 contained sequencing errors or were identified as fragments and were manually corrected/assembled (see methods for details). For J08/09 and J38/39, the manual assembly resulted in two closely related proteins, and therefore both versions were tested.

Cell-Free and *E. coli* Expression and Screening of Predicted Cellulase Genes

Each of the thirty-seven predicted metagenome-derived cellulase genes were synthesized and cloned into a custom vector for in vitro cell-free expression using a T7 promoter/terminator-based system. Each gene was expressed in vitro and screened for endoglucanase, cellobiohydrolase and β-glucosidase activity (Table 2). For comparison to the cell-free system, each gene was then cloned into the pDEST17 vector for expression in *E. coli* and screened for the same activities (Table 2). There was a large degree of overlap between the two expression methods, but the *E. coli*-based screen detected activity from a larger subset of genes than the cell-free screen (26 vs 19). BG activity was detected for fifteen of the nineteen predicted β-glucosidases, and none of these enzymes showed endoglucanase activity, consistent with their annotation. Furthermore, twelve of these fifteen positive candidates exhibited CBH activity, indicating that these enzymes have activity on glucose oligomers with n>2. For the predicted endoglucanases, activity was detected for eleven of the sixteen candidates. In addition to endoglucanase activity, seven of the eleven endoglucanases also had BG and/or CBH activity. No activity was detected for the two predicted CBH genes.

Activity Profile of Cellulases

Of the thirty-seven enzymes in the initial screen, fifteen of the nineteen β-glucosidases and six of the sixteen endoglucanases were expressed at sufficient quantities to profile in greater detail. The activity of each enzyme was measured at temperatures ranging from 45 and 99° C., pH between 4.0 and 8.0, and IL concentrations ranging from 0 to 40% [C2mim][OAc] (v/v). These data were then plotted and optimal temperature/pH and IL-tolerance was determined for each enzyme (Table 3). To illustrate the dynamic activity range of each enzyme, the temperature, pH and IL concentration ranges that gave greater than 80 or 50% activity compared to the optimal activity are also reported in Table 3. All of the enzymes were active at elevated temperature, but the range of optimum temperatures (Topt) was broad, ranging from 45 to 95° C. The enzymes were divided into two groups: seven enzymes with a Topt within 5 degrees of 70° C. and another seven near 90° C. Of the remaining enzymes, five had a Topt below 70° C. and two had an intermediate Topt of 80° C. The enzymes also showed a similar clustering around optimal pH values (pHopt), with fourteen enzymes having a slightly acidic pHopt between 5.0 and 6.0 and the remaining seven enzymes having a pHopt between 6.5 and 7.5. However, many of these enzymes were active over a broad pH range, and all but J16 retained ≥50% activity at pH 7.0. Five of the enzymes were more than 80% active at the highest pH tested of 8.0, indicating that these enzymes also tolerate slightly alkaline conditions.

Surprisingly, most of the enzymes (sixteen of the twenty-one tested) showed an initial increase in activity in the presence of [C2mim][OAc] compared to water (0% IL), with a 15 to 500% enhancement in activity that eventually declined at higher [C2mim][OAc] concentrations (Table 3). This phenomenon is illustrated in the row labeled "Max Activity in IL" in Table 3 that lists the highest fold change in activity in the presence of [C2mim][OAc]. For example, enzyme J16 was found to be five times more active in 10% (v/v) [C2mim][OAc] than in water. The majority of the enzymes were active in at least 20% (v/v) [C2mim][OAc] and maintained greater than 50% activity. Six of the enzymes (J03, J05, J16, J25, J26 and J36) maintained more than 80% activity in 35 to 40% [C2mim][OAc]. Only a single enzyme, J15, lost activity at low [C2mim][OAc] concentrations. The β-glucosidase enzymes J5 and J16 and endoglucanase enzymes J26 and J36 showed the highest increase in activity in the presence of [C2mim][OAc]. To examine the relationship of IL-tolerance to potential halotolerance, their activity was measured in equal molar concentrations of [C2mim][OAc] and NaOAc (FIG. 1A-B). Each of these enzymes also showed greater or equal activity in the presence of NaOAc, despite this salt buffering the solution at a more basic pH, which tends to be outside the optimal activity range for these enzymes (in water), especially J16 (FIG. 1C-D).

Figure 2:
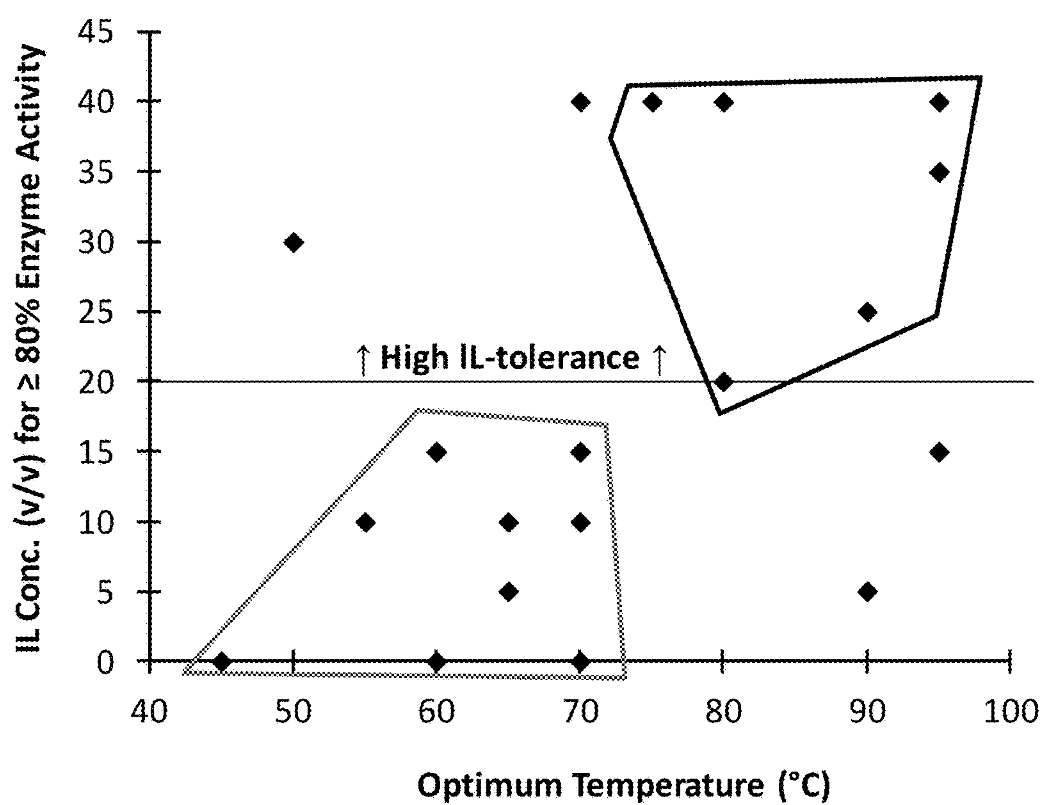
FIG. 2: A plot highlighting the correlation between thermotolerance and IL-tolerance of the enzymes in Table 3. The plot shows the maximum [$C_2$mim][OAc] concentration that permits ≥80% enzyme activity compared to water versus the optimum temperature of the enzyme. There are two overlapping data points at (95° C., 35% IL). Enzymes with high IL-tolerance are defined as the enzymes that can tolerate 20% (v/v) [$C_2$mim][OAc] or greater (above horizontal line). The enzymes fall into two clusters: the black polygon where 78% (7/9) of the enzymes with a Topt >70° C. have high IL-tolerance, and the grey polygon where 82% (9/11) of the enzymes with a Topt ≥70° C. have low or no IL-tolerance. Only 18% (2/11) of the enzymes with a Topt ≥70° C. have high IL-tolerance.

The Topt and pHopt of these enzymes were compared to their IL-tolerance, and only the Topt showed any discernable correlation with IL-tolerance (FIG. 2). It appears that a Topt of >70° C. is a positive indicator for high IL-tolerance. For the sample of enzymes in this study, those with a Topt of ≥70° C. have an 18% probability of being IL-tolerant (remaining more than 80% active in concentrations of at least 20% v/v [C2mim][OAc]), while enzymes with a Topt of >70° C. have a 78% chance of being highly IL-tolerant.

Discussion

Several reports investigating the behavior of thermophilic enzymes in the presence of ILs have found a correlation between thermotolerance and IL-tolerance (Park et al., 2012, supra; Gladden et al., 2011, supra; Datta et al., 2010, supra). Developing IL-tolerant enzymatic mixtures for cellulose hydrolysis will permit the development of technologies that combine IL-based pretreatment using [C2mim][OAc] with enzymatic hydrolysis. This type of process intensification will be important for the development of cost competitive lignocellulosic biofuel technologies (Klein-Marcuschamer et al., *Biofuels, Bioproducts and Biorefining* 5:562-569, 2011). This study sought to explore the hypothesis that thermotolerance and IL-tolerance were correlated by identifying, expressing, and characterizing multiple thermophilic biomass deconstructing enzymes sourced from a single compost-derived microbial community that was a promising test bed for comparing ionic liquid and thermotolerance (Gladden et al., 2011 supra; D'Haeseleer et al., 2013, supra). In the process, we compared cell-free and in vivo *E. coli* expression methods for rapidly (and with high fidelity)

screening through potential enzyme candidates to narrow down the list of targets to functional and properly annotated enzymes.

Comparison of the cell-free and in vivo *E. coli* screens yielded several observations: 1) both screens work well at quickly screening through candidate genes to identify functional genes; 2) the screens produce similar results in regards to predicted annotation; 3) the cell-free screen is more rapid (24 hours) compared to the in vivo screen (5 days); 4) the cell-free screen missed about 27% of the "positive" candidates (19 vs. 26); and 5) the cell-free screen will eventually require porting into an in vivo expression system to conduct more detailed enzyme profiling. In light of these observations, the cell-free screen would be advantageous if the number of candidates is to screen is large, as it is more rapid and less labor intensive than the in vivo screen, while the in vivo screen would be more advantageous in smaller screens as it provides greater returns and enables more detailed characterization efforts. Overall, the assigned annotation of each enzyme accurately reflected their measured activity. Several enzymes showed activity on multiple substrates, but in most cases the highest measured activity matched the annotation of the enzyme.

After the initial screening, there were twenty-one promising enzyme targets (15 BG and 6 Endo) to profile in more detail for optimum temperature, pH and IL-tolerance. The profiles revealed that the enzymes are indeed thermotolerant, and the two clusters of optimum temperatures observed for these enzymes (70 and 90° C.) mirror the pattern seen in the profile of the native enzymes produced by the parent community from which these genes were isolated, except that the native enzymes had their had two Topt peaks 10 degrees lower than the heterologous enzymes (60 and 80° C.) [14]. It is unclear why this may be, other than that the community produced a complex mixture of enzymes, the sum of which skewed the average optimum temperature observed down for the mixture compared to the individual enzymes.

The enzymes produced by the native community were also [C2mim][OAc]-tolerant, which was a trait mirrored by the majority of enzymes profiled in this study. An unanticipated observation was that many of these enzymes showed an increase in activity in low concentrations of [C2mim][OAc], some several fold over the activity in water. The fact that several of these enzymes also showed increased activity in the presence of NaOAc suggests that these enzymes may require the presence of salt for optimal activity. The increase in activity with NaOAc was not as high for enzyme J16 as in the corresponding amount of IL, which is likely due to the more basic pH of NaOAc and the lower pH optimum of J16 (pH 5.0). This phenomenon was less apparent for the other enzymes tested, but generally the enzymes demonstrated relatively higher levels of activity in the presence of [C2mim][OAc] compared to NaOAc. Unlike many fungal enzymes, these cellulases tend to prefer more neutral pH (6 or 7), and many retained more than 80% activity at the highest pH tested of 8.0. ILs such as [C2mim][OAc] tend to buffer around neutral pH in the range of concentrations tested, a property that may further lend to the tolerance of this IL by several of the enzymes tested. The affinity of these enzymes for more neutral pH may reflect their origin; for example, *R. marinus* grows optimally at pH 7.0 (Bjornsdottir et al., *Extremophiles* 10:1-16, 2006)

The mechanisms of IL-tolerance are not well understood; few enzymes have been investigated for IL-tolerance and there are no studies that have looked at a large enough set of enzymes with a single type of IL, such as [C2mim][OAc], to do any type of thorough comparative analysis. The twenty-one enzymes characterized in this study had varying degrees of [C2mim][OAc]-tolerance. There appears to be a correlation between IL-tolerance and Topt. A comparison of the IL-tolerance and Topt of this set of enzymes reveals that the enzymes with Topt greater than 70° C. tend to have a higher probability of tolerating high concentrations of IL. This indicates that evolution towards higher Topt frequently alters the properties of an enzyme in a manner that also promotes tolerance to ILs such as [C2mim][OAc].

The results presented here also illustrate a general strategy used to identify enzymes with a particular set of characteristics, in this case IL-tolerance. The microbial community from which these enzymes were derived was originally established under the premise that organisms endowed with a particular functionality could be selectively enriched in abundance from a complex microbial community by cultivation under defined conditions. This selective enrichment could then help researchers target organisms and genes with a desired set of characteristics. In this case, the desired functionality was production of cellulase enzymes and the desired characteristic was thermo- and IL-tolerant cellulase enzymes. This strategy was implemented by cultivating a microbial community derived from green-waste compost under thermophilic conditions with plant biomass as a sole carbon source (Gladden et al., 2011, supra). The native enzymes produced by this community were both thermo- and IL-tolerant and so were the recombinant enzymes derived from this community, suggesting that selective cultivation is a good method for discovering enzymes that function under a desired set of conditions.

The enzymes characterized in this report are some of the most tolerant to [C2mim][OAc] reported to date (Turner et al., 2003, supra; Gladden et al., 2011, supra; Datta et al., 2010, supra; Zhang et al., 2011, supra). Tolerance to this particular IL is of increasing interest as it is currently one of the most effective and well-studied ILs for pretreatment of lignocellulosic biomass (Sathitsuksanoh et al., *Journal of Chemical Technology & Biotechnology* 88:169-180, 2013). Recent efforts to develop IL-tolerant cellulase cocktails and to incorporate these cocktails into "one-pot" pretreatment and saccharification bioprocessing schemes show that IL-tolerant enzymes can be used to develop new technologies to deconstruct biomass, and open up the technological landscape for lignocellulosic biorefineries (Shi et al, 2013, supra). The enzymes described in this report can be used in these technologies.

Methods

Manual Cellulase Gene Assembly

While most of the full length ORFs in Table 1 were taken directly from the metagenome, several were manually reconstructed from fragmented genes identified in the assembly of the metagenomic dataset. The following ORFs were manually assembled: J03 had an incorrectly predicted start codon. The start of this ORF was moved 5' to match the start of its top BLAST hit. J08/09 are two versions of a single ORF composed of four gene fragments from the metagenome (IMG gene IDs 2061981261, 2062002762, 2062037967, 2061992858), which all have very high homology with a predicted beta-galactosidase from *Thermobaculum terrenum* ATCC BAA-798 (Gen Bank Accession # ACZ42845.1). J08 is an assembly of 2061981261 (N-terminus), 2062002762 (C-terminus), and ACZ42845.1 (sequence that encodes AAIVITENGAAYPDE (SEQ ID NO:27) inserted between the two sequences), while J09 is a compilation of 2062037967, 2061992858, and the same fragment from ACZ42845.1 assembled in the same order as J08. Overall, J08 and J09 differ by 5 AA. The same situation applies to J10, which is assembled from 2062002992 (N-term), 2062002993 (C-term), and a middle fragment (sequence encoding NAVKVTAAA (SEQ ID NO:28)) from ACX65411.1, a glycoside hydrolase family 3 protein from *Geobacillus* sp. Y412MC1. J11 was also assembled in the same manner; two consecutive ORFs (2062005533 and 2062005534) were merged with a fragment encoding (YVR) derived from a glycoside hydrolase family 3 protein from *Ktedonobacter racemifer* DSM 44963 (EFH83601.1). J38/39 are two versions of two consecutive orfs (2062019305, and 2062019306), which may be separated by a single base pair frame shift or a larger deletion. J38 is a merger of the two orfs by inserting a single base pair to encode a leucine codon at residue 103. J39 is a merger of the two ORFs with a 316 base pair insertion at the same location derived from, a beta-glucosidase from *Paenibacillus* sp. JDR-2 (ACT00588.1), to repair the glycoside hydrolase family 3 N-terminal domain.

Gene Synthesis and Cloning

Each gene was codon optimized for expression in *E. coli* and synthesized by Genscript (Piscataway, N.J.). They were then cloned into a modified pUC57 vector constructed at Genscript, pUC57CFv1, with an added T7 promoter and terminator, as well as gateway attB1/attB2 sequences flanking the ORF, and a 8× C-terminal 8× His and Strep-tag II dual tag. There was an in frame NheI-XhoI cloning site added between the attB1/attB2 sequences to place the ORFs into the pUC57CFv1 vector. The added vector sequences were cloned into the pUC57 vector at the EcoRI and SacI sites. Synthesized ORFs were then cloned into the pUC57CFv1 vector at the NheI-XhoI sites. The synthesized genes in the pUC57CFE1 vector were transformed in to TOP10 *E. coli* for storage at −80° C.

The T7, Gateway attB1/attB2 and His tag sequences added to pUC57are:

```
                                        (SEQ ID NO: 29)
GAATTCTAAATTAATACGACTCACTATAGGGAGACCACAACGGTTTCCCT

CTAGAAATAATTTTGTTTAACTTTAAGAAGGAGATATACATATGACAAGT

TTGTACAAAAAAGCAGGCTTCGCTAGCCCAATCCAATCTCGAGGACCCAG

CTTTCTTGTACAAAGTGGTCCATCATCACCATCACCATTAACAATAACTA

GCATAACCCCTTGGGGCCTCTAAACGGGTCTTGAGGGGTTTTTTGGAGCT

C.
```

In Vitro and In Vivo Expression of Cellulases

Each of the thirty-seven cellulases was expressed in vitro using the RTS 100 *E. coli* 100 Hy cell-free expression Kit (Roche Diagnostics, Germany Cat. No. 03 186 148 001), using 0.5 μg of vector and following the manufactures instructions. The lyophilized plasmids were dissolved in DNase/RNase-free water before use. The in vitro protein expression was performed at 30° C. for six hours. The expression products were used immediately for enzyme assay reactions.

To validate the enzyme activity results of in vitro protein expression and assays, the cellulase genes were cloned into the low-copy bacterial expression plasmid pDEST17 by Gateway cloning techniques following the manufacturer instructions (Invitrogen). The sequences of all cloned genes in the pDONR221 and pDEST17 vectors were verified by DNA sequencing (Quintara Biosciences; Albany, Calif.). All cellulase genes in the pDEST17 vector, except J24 and J29, were transformed into BL21(DE3) Star *E. coli* (Invitrogen). The J24 and J29 genes in the pDEST17 vector were transformed into the T7 Express Iq *E. coli* strain (New England BioLabs) to attenuate the basal level of cellulase expression during growth phase prior to induction of protein expression. This was done because the expression vectors containing J24 and J29 were toxic to TOP10 and BL21(DE3)Star strains of *E. coli*, presumably due to the 'leaky' activation of the T7 promoter. Bacterial cultures were grown in 96-deep well plates in 800 μL of LB containing carbenicillin (50 μg/ml) in each well. The overnight cultures of *E. coli* were inoculated to fresh LB medium containing Overnight Express Autoduction System 1 (Calbiochem) reagent and carbenicillin. In the autoinduction medium, the bacterial cultures were incubated at 37° C. with constant shaking at 200 RPM for the first four hours. Then the cultures were grown at 30° C. for 18 hr with constant shaking at 200 RPM. The cell pellets were harvested by centrifugation at 6,000 g for 30 min, and then stored at −20° C. Each of the frozen cell pellets was thawed and resuspended in 0.1 mL of BugBuster containing lysozyme (1 mg/mL), Benzonase (25 U/ml) and PMSF (1 mM). After 30 min of incubation at room temperature, the cell lysates were centrifuged at 4,000 g for 30 min at 4° C. The soluble protein extracts (supernatants) were filtered through 0.45 μm syringe filters, and then used for enzymatic assays.

Enzyme Assays for In Vitro and In Vivo Screens

The enzyme activities of the in vitro protein expression products from the pUC57CFE1 vector were screened on the following substrates: 4-nitrophenyl-β-D-glucopyranoside (pNPG, 5 mM), 4-nitrophenyl-β-D-cellobioside (pNPC, 5 mM), and 1% carboxymethyl cellulose (Sigma Aldrich). Each enzyme reaction mixture containing one of these substrates and 5 μL of in vitro expression product or soluble extract from *E. coli* cell lysates (before or after induction) was done in 50 mM sodium acetate buffer at pH 5 in a total volume of 50 μL. The final concentration of 4-nitrophenol labeled substrate (pNPC, or pNPG) was 5 mM, and that of CMC was 1% in each reaction. The enzymatic reaction was done at 50° C. for 16 hr. For the reaction mixtures containing CMC, DNS assay was used to quantify hydrolyzed products. For the reaction mixtures containing pNPG, or pNPC, an equal volume of 2% Na2CO3 was added prior to measuring absorbance at 420 nm to detect hydrolyzed 4-nitrophenol.

Enzyme Assays for Activity Profiling of Cellulases

To profile the enzyme activity of positive cellulases in the screen, each enzyme was expressed in vivo as described above, except the culture volume was scaled to 50 ml. For each enzyme assay, 5 to 20 μL of lysate was used, depending on the activity of the enzyme. Enzymes J1 to J19 were screened using pNPG (5 mM final concentration) and enzymes J21 to J39 were screened using CMC (1% w/v final concentration) in a 100 μL reaction volume. Each value reported in Table 3 is from the average of triplicate reactions. For the temperature profile, the reaction was set up using 50 mM MES buffer pH 6.5, and reactions were run for 15 to 60 min, depending on enzyme activity, at 5 degree increments from 45 to 99° C. For the pH profile, the reactions were run at ~10° C. below the optimal temperature of each enzyme in 100 mM NaOAc 50 mM MES and 50 mM HEPES buffers between pH 4.0 and 8.0. The buffers were made by mixing two aliquots of the aforementioned buffer set to either pH 4.0 (Buffer A) or 8.0 (Buffer B) in 10% increments, starting from 0% B to 100% B, giving 11 points total between pH 4.0 and 8.0. For IL-tolerance profiles, the reactions were run without added buffer in IL concentrations between 0 and 40% w/v [C2mim][OAc] at ~10° C. below the optimal temperature of each enzyme. Reaction times were set to keep the values within the linear range of detection. For some enzymes, the same reaction was set up substituting an equal molar amount of NaOAc for [C2mim][OAc]. FIG. 1C-D shows the pH at each concentration of IL and molar equivalent concentrations of NaOAc.

TABLE 1

Predicted cellulase enzymes identified in the switchgrass-adapted metagenome.

| ID | IMG Gene ID | GH Fam | Predicted Function | Max Identity (%) | Genbank Accession | Top Blast Hit Organism | Metagenome bin* |
|---|---|---|---|---|---|---|---|
| J01 | 2061974227 | 3 | β-glucosidase | 42 | ZP_06970881.1 | *Ktedonobacter racemifer* DSM 44963 | *Paenibacillus* |
| J02 | 2061976655 | 3 | β-glucosidase | 97 | YP_003321925.1 | *Thermobaculum terrenum* | *Thermobaculum* |
| J03 | 2061976732 | 3 | β-glucosidase | 96 | YP_003322827.1 | *Thermobaculum terrenum* | *Thermobaculum* |
| J04 | 2061977694 | 1 | β-glucosidase | 62 | ZP_10205923.1 | *Rhodanobacter thiooxydans* LCS2 | Gemmatimonadetes |
| J05 | 2061979262 | 3 | β-glucosidase | 44 | YP_002760449.1 | *Gemmatimonas aurantiaca* T-27 | Gemmatimonadetes |
| J06 | 2061979786 | 1 | β-glucosidase | 61 | ZP_08918778.1 | *Thermobacillus composti* KWC4 | *Paenibacillus* |
| J07 | 2061980390 | 1 | β-glucosidase | 66 | NP_242789.1 | *Bacillus halodurans* C-125 | Not Binned |
| J08 | 2062002762 | 1 | β-glucosidase | 99 | YP_003323667.1 | *Thermobaculum terrenum* ATCC BAA-798 | Not Binned |
| J09 | 2062002762 | 1 | β-glucosidase | 98 | YP_003323667.1 | *Thermobaculum terrenum* ATCC BAA-798 | Not Binned |
| J10 | 2062002993 | 3 | β-glucosidase | 77 | ZP_09004353.1 | *Paenibacillus lactis* 154 | Not Binned |
| J11 | 2062005533 | 3 | β-glucosidase | 42 | ZP_06970881.1 | *Ktedonobacter racemifer* DSM 44963 | Not Binned |
| J12 | 2062006736 | 3 | β-glucosidase | 94 | YP_003291338.1 | *Rhodothermus marinus* DSM 4252 | Rhodothermus1 |
| J13 | 2062007625 | 1 | β-glucosidase | 93 | YP_003318753.1 | *Sphaerobacter thermophilus* DSM 20745 | *Sphaerobacter* |
| J14 | 2062008681 | 3 | β-glucosidase | 97 | YP_003324065.1 | *Thermobaculum terrenum* ATCC BAA-798 | *Sphaerobacter* |
| J15 | 2062012385 | 3 | β-glucosidase | 75 | YP_823953.1 | *Candidatus Solibacter* usitatus Ellin6076 | Not Binned |
| J16 | 2062018481 | 3 | β-glucosidase | 100 | YP_004824792.1 | *Rhodothermus marinus* SG0.5JP17-172 | *Rhodothermus*1 |
| J17 | 2062019328 | 3 | β-glucosidase | 71 | ZP_08918857.1 | *Thermobacillus composti* KWC4 | *Paenibacillus* |
| J18 | 2062019735 | 1 | β-glucosidase | 99 | AAN05441.1 | *Thermus* sp. IB-21 | *Thermus* |
| J19 | 2062026722 | 1 | β-glucosidase | 72 | YP_002522957.1 | *Thermomicrobium roseum* DSM 5159 | *Thermomicrobium* |
| J21 | 2061975668 | 9 | Endoglucanase | 54 | YP_002759529.1 | *Gemmatimonas aurantiaca* T-27 | Gemmatimonadetes |
| J22 | 2061976479 | 8 | Endoglucanase | 72 | BAF49077.1 | *Paenibacillus* sp. W-61 | *Paenibacillus* |
| J23 | 2061977143 | 5 | Endoglucanase | 32 | ZP_09216417.1 | *Gordonia amarae* NBRC 15530 | *Sphaerobacter*2 |
| J24 | 2061979932 | 9 | Endoglucanase | 54 | ACJ68032.1 | *Paenibacillus provencensis* | *Paenibacillus* |
| J25 | 2061986269 | 12 | Endoglucanase | 98 | YP_004824941.1 | *Rhodothermus marinus* SG0.5JP17-172 | Rhodothermus2 |
| J26 | 2061990001 | 12 | Endoglucanase | 100 | YP_004824941.1 | *Rhodothermus marinus* SG0.5JP17-172 | Not Binned |
| J27 | 2061990054 | 5 | Endoglucanase | 35 | ZP_09309733.1 | *Rhodococcus pyridinivorans* AK37 | *Sphaerobacter*2 |
| J28 | 2061994288 | 5 | Endoglucanase | 98 | YP_003323917.1 | *Thermobaculum terrenum* ATCC BAA-798 | *Sphaerobacter* |
| J29 | 2062006179 | 5 | Endoglucanase | 52 | BAJ22272.1 | *Paenibacillus* sp. KSM-N546 | *Paenibacillus* |
| J30 | 2062016312 | 9 | Endoglucanase | 54 | ZP_08919343.1 | *Thermobacillus composti* KWC4 | Not Binned |
| J31 | 2062017860 | 5 | Endoglucanase | 57 | ZP_08873206.1 | *Verminephrobacter aporrectodeae* | Not Binned |
| J32 | 2062025020 | 5 | Endoglucanase | 96 | YP_003320228.1 | *Sphaerobacter thermophilus* DSM 20745 | Not Binned |
| J33 | 2062027867 | 8 | Endoglucanase | 72 | ZP_04851456.1 | *Paenibacillus* sp. oral taxon 786 str. D14 | Not Binned |
| J34 | 2062029826 | 6 | Endoglucanase | 37 | ZP_06416445.1 | *Frankia* sp. EUN1f | *Thermobaculum* |
| J35 | 2062032441 | 5 | Endoglucanase | 35 | ZP_08873206.1 | *Verminephrobacter aporrectodeae* | Not Binned |
| J36 | 2062035244 | 5 | Endoglucanase | 100 | YP_004823815.1 | *Rhodothermus marinus* SG0.5JP17-172 | *Rhodothermus*1 |
| J38 | 2062019306 | 3 | Cellobiohydrolase | 57 | ZP_08918880.1 | *Thermobacillus composti* KWC4 | *Paenibacillus* |
| J39 | 2062019306 | 3 | Cellobiohydrolase | 76 | ZP_08918880.1 | *Thermobacillus composti* KWC4 | *Paenibacillus* |

GH Fam = Glyohydrolase Family No.

*Metagenomic bin indicates the predicted source organism. Refer to D'Haeseleer et. al., supra, for details. Gene sequence and annotation can be found at the Joint Genome Institute's img/m website img.jgi.doe.gov/cgi-bin/m/main.cgi under the "Find Genes" tab using the IMG/M gene ID in the table.

TABLE 2

Screen of predicted glycoside hydrolase enzymes for β-glucosidase, endoglucanase, and cellobiohydrolase activity.

| Gene ID | 1 | 2 | 3 | 4 | 5 | 6 | 7 | 8 | 9 | 10 | 11 | 12 | 13 | 14 | 15 | 16 | 17 | 18 | 19 | 21 |
|---|---|---|---|---|---|---|---|---|---|---|---|---|---|---|---|---|---|---|---|---|
| Endo | | | | | | | | | | | | | | | | | | | | |
| CBH | | + | + | | | + | | + | + | | + | | | + | + | | + | + | + | |
| | + | | | | | + | + | + | + | | | | | + | | | + | + | + | |
| βG | + | + | + | | | + | | + | + | | + | | | + | + | | + | + | + | |
| | + | + | + | | + | + | + | + | + | | + | | | + | + | + | + | + | + | |

| Gene ID | 22 | 23 | 24 | 25 | 26 | 27 | 28 | 29 | 30 | 31 | 32 | 33 | 34 | 35 | 36 | 38 | 39 | |
|---|---|---|---|---|---|---|---|---|---|---|---|---|---|---|---|---|---|---|
| Endo | | | + | | | | + | + | + | | | | | | + | | | cell-free |
| | | + | + | | + | + | + | + | + | + | + | | | + | + | | | in vivo |
| CBH | | | | | | | | | | | | | | | | | | cell-free |
| | | | + | | + | | | + | + | | | | | | + | | | in vivo |
| βG | | | | | | | | | | + | | | | + | | | | cell-free |
| | | | | | + | | | | | + | | | | | | | | in vivo |

Cell-free and in vivo expressed enzymes are labeled in the far right column.

Enzyme activities are as follows: Endoglucanase (Endo), cellobiohydrolase (CBH), and β-glucosidase (βG).

Detection of enzymatic activity is indicated with a + for positive and a blank box for negative.

TABLE 3

Activity profile of the active glycoside hydrolase enzymes.

| Gene ID | 01 | 02 | 03 | 05 | 06 | 07 | 08 | 09 | 11 | 14 | 15 |
|---|---|---|---|---|---|---|---|---|---|---|---|
| $T_{opt}$ (° C.) | 45 | 90 | 75 | 70 | 65 | 70 | 90 | 90 | 60 | 70 | 70 |
| Temp (° C.) ≥80% Activity | 45-50 | 80-90 | 75 | 60-75 | 55-70 | 65-70 | 80-90 | 80-90 | 55-60 | 60-75 | 65-70 |
| Temp (° C.) ≥50% Activity | 45-55 | 70-90 | 70-80 | 45-80 | 45-75 | 60-75 | 65-90 | 65-90 | 45-65 | 50-75 | 60-70 |
| $pH_{opt}$ | 6 | 7 | 5.5 | 7 | 6 | 6 | 5 | 5 | 6 | 6 | 6.5 |
| pH ≥80% Activity | 6-6.5 | 5.5-8 | 4.5-6 | 6-7.5 | 5-6.5 | 6-7.5 | 4-8 | 4-8 | 5-6.5 | 5.5-7.5 | 6-7 |
| pH ≥50% Activity | 5-7 | 4.5-8 | 4.5-7 | 5.5-8 | 4.5-7.5 | 5.5-8 | 4-8 | 4-8 | 4.5-7 | 5-8 | 6-7.5 |
| IL % (v/v) ≥100% Activity | 0 | 15 | 40 | 35 | 5 | 10 | 0 | 0 | 10 | 5 | 0 |
| IL % (v/v) ≥80% Activity | 0 | 25 | 40 | 40 | 5 | 15 | 5 | 5 | 15 | 10 | 0 |
| IL % (v/v) ≥50% Activity | 15 | 35 | 40 | 40 | 5 | 15 | 20 | 20 | 20 | 20 | 0 |
| Max Activity in IL* | 0.68 (5) | 1.1 (5) | 1.2 (40) | 2.1 (15) | 1.3 (5) | 1.2 (5) | 0.87 (5) | 0.89 (5) | 1.5 (5) | 1.2 (5) | 0.45 (5) |

| Gene ID | 16 | 17 | 18 | 19 | 24 | 25 | 26 | 29 | 30 | 36 |
|---|---|---|---|---|---|---|---|---|---|---|
| $T_{opt}$ (° C.) | 80 | 60 | 95 | 80 | 55 | 95 | 95 | 65 | 50 | 95 |
| Temp (° C.) ≥80% Activity | 75-80 | 55-60 | 85-95 | 70-85 | 50-60 | 80-95 | 85-95 | 55-70 | 45-55 | 75-95 |
| Temp (° C.) ≥50% Activity | 70-80 | 45-60 | 70-95 | 60-85 | 45-65 | 60-95 | 75-95 | 50-70 | 45-55 | 55-95 |
| $pH_{opt}$ | 5 | 6 | 6 | 5.5 | 6.5 | 7.5 | 7.5 | 7.5 | 6 | 6 |
| pH ≥80% Activity | 5-5.5 | 5-7 | 4.5-7 | 4.5-7.5 | 5.5-7.5 | 4-8 | 5.5-8 | 5.5-8 | 5-7 | 6-7.5 |
| pH ≥50% Activity | 5-6.5 | 5-7.5 | 4-8 | 4.5-8 | 5-8 | 4-8 | 4-8 | 5-8 | 4.5-8 | 5.5-8 |
| IL % (v/v) ≥100% Activity | 35 | 0 | 5 | 10 | 10 | 40 | 30 | 5 | 25 | 35 |
| IL % (v/v) ≥80% Activity | 40 | 0 | 15 | 20 | 10 | 40 | 35 | 10 | 30 | 35 |
| IL % (v/v) ≥50% Activity | 40 | 5 | 30 | 30 | 15 | 40 | 35 | 15 | 35 | 35 |
| Max Activity in IL* | 5 (10) | 0.5 (5) | 1.2 (5) | 1.1 (5) | 2.1 (5) | 1.9 (15) | 2.5 (15) | 1.4 (5) | 2.5 (15) | 2 (25) |

Enzyme activity was profiled at temperatures between 45 and 95° C., pH between 4 and 8, and IL concentrations between 0 and 40% (v/v) of [C2mim][OAc].

The temperature and pH that elicited the highest activity is indicated in row Topt and pHopt, respectively.

Temperature and pH ranges that permitted greater than 80% and 50% activity are indicated below the optimum value.

IL-tolerance is indicated as the maximum concentration of [C2mim][OAc] that permits at least 80% and 50% enzyme activity (i.e. a value of 15 in the 80% row would indicate that 15% (v/v) of [C2mim][OAc] is the maximum concentration of [C2mim][OAc] that can be used to retain at least 80% enzyme activity).

Most enzymes showed a steady decline in activity with increasing IL concentrations.

*Max activity in IL is reported as the highest fold change of activity in the presence of IL compared to water and the ( ) indicates the IL concentration (v/v) in which that highest activity as achieved.

Values less than 1 indicate the enzyme is less active in IL than in water while values greater than 1 indicate the enzyme has increased activity in the presence of IL.

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession number, and patent applications cited herein are hereby incorporated by reference in their entirety for all purposes.

Table of Illustrative Sequences

J01-SEQ ID NO: 1

VRMEELVGRLTLEEKAALLEGADSWYTNPVPRLGIPRLHLTDGPHGVRQVRRAGGGFSVSDNEPATAFPTSA
AVASSWNPELARRMGEAIAEECLAAGVDVLLAPGINIKRSPLCGRNFEYYSEDPLVSAAFGAAFVQGVQSKG
VGCCVKHFAVNSNETFRFVGDSVVDERALREIYLRAFESVVKNAKPYAVMSAYNKVNGTFASENRLLLTDILR
REWGFDGVVMTDWGATCDRVEGLLAGCDLDMPGGSWHNRKAILEAARSGRLAADVLDASVRRMLRLIG
RCRTGKAERQAAPDFEKHAALACDIAKESAVLLKNDGTLPLSGGERLLVVGEMFEKMRFQGAGSSLVHPTD
VVTPKDAFDRRGISYAYEKGYRSFDPGRDERLEQAAVRAAEDADVILFFGGLTDFEESEGFDREHMRLGDNQ
TALLEKLAATGKKLVFVLFAGAPVELPFHDELSALLYMVLPGQRGGEAAAALLYGEAAPSGKLAESWPMRLE
DTSCFADYNRGPVSRYYESIYVGYRAYDKAGTKLRFPFGFGLSYTTFAYAGMTVREEDGRVAVSADITNTGKR
RGAEVVCILYVRHKASAVFRPDKELKAFAKVFLEPGETKRVELAFDKRDLAFWHAGLGRWVVENGTYELLLAA
SAADVRLAAELSVTDGETIGGTVPHPYPPDVADAYAMPPKDVPACFGRLAGRADAGDDPADGQAGGFHG
ETDKPLGKPDGSGGDGTGGNGPGGKADGRRRPSGRRRHPPLTMETQLRDFRRTFGGRIFYEMVMRSVRRE
YEAALAMPDSLERDSRLKNTHFFLRLMPLNTPRTMSMSSGGAFPYRVAEALVALANGQMLKGLSLLMKKEK
PVPLPKDAE

J02-SEQ ID NO: 2

VSSETFAYKDSSLPIDORIDDLLSRMSIDEKIAQLGCIWSTDLIREGRFDPDYAISQIPNGIGQVTRIGAATGLRP
NESANLMNSIQKVVIERTRLGIPVFIHEESVGGFCHRDATVFPQALGLACSWNPELIEKVAQVIREQMLAVGA
RLALAPVLDVARDPRWGRVEETYGEDPVLVGTMGTAYIKGLQGDDLAQGVAATGKHFLAYSFSLGGRNWG
PVHVGPRELREVYAEPFAAAIRDAGLSVIMNSYASVDGLPCAGSKSILTDLLRKELGFKGSVVADYFSVEMLRS
FHKVAADKSEAACIALNAGLDMELPALDCFGEPLKKAIEAGSINIEVIDTAVRRVLELKFRLGLFENPYVDAGVT
SSKFQTPEQRQLAYQAAAESVVLLKNDGVLPISKDDVKSIAVIGPAADDKRLLQGDYHYPAHLESLFESQSDTE
SLGLLSEEPAPTPAGQLNLGNFAPGPYYTPHVTPLQAIRDKHPDIDVIYEKGCDILGDDRSGFAAAVNAASNA
DVSIVFVGGKSGLKRPATSGEANDATSLSLTGVQADLVRAIAEAAKKLVVVVISGRVHTLEDLVDSTNALIFCV
PPGEEGGNAIVDVLFGSVCPSGKLPVSFPRRVGQVPDYFGQRNGGDRAMFFGDYIDSTVDPLFPFGYGLSYT
HFEYSQPNIEVGDTTKPTAISFEIKNVGEYTGSEVVQLYCQDVVASVSRPTNMLLGFTKVRLDPGQSKKLTFIV
HPSRLAFYNEAMQFVTEPGQYIFRVGSSSVDIRHELDVTLTGEAAYYNCIRDVVATTVVVE

J03-SEQ ID NO: 3

LTRDIKSLIAQMTLEEKASLCSGLGFWDTKPIERLGIPSIVMTDGPHGLRKQVPGSQNFFDSVPATCFPTAATI
ACSWDRSLVREIGIALGEECQAEGVSVILGPGVNIKRSPLCGRNFEYFSEDPFLSTELAASYIEGVQSQGVGTSI
KHFAANNQEHRRMSVNAIVDERTLREIYLASFEGAVKKSKPWTVMCAYNRLNGDYCSENHYLLTKVLREDW
GYEGLVVSDWGAVNERVKGLEAGLDLEMPGNGGVGDRKIIEAVRSGELSEEVLDRAVERILKLIFQAVDNRK
ENFRYDADAHHQLARKAARESMVLLKNDNSILPLRKEGTIAVIGAFAKHPRFQGGGSSHVNPTRIDIPYDEIQ
KVVGDSVRLLYSDGYQLGSDEVNQPLIEEARKIASQANVALIFAGLPENYESEGYDRVHMSMPRSHLELIQAV
SESQPNTVVLLCNGAPVEMPWLHNVPAVLECYLGGQAVGSAIADLLFGEASPCGKLAETFPQKLSDNPSYLN
FPGEDDKVEYREGIFVGYRYYDTKEIQPLFPFGHGLSYTTFEYSDLSVDKKSIKDNEIVNVQVTVKNTGKFAGKE
IVQLYVRDLASSVVRRPEKELKGFEKVDLQPGEEKTVNFTLDKRAFAYYNVDLSDWYVETGEFEICVGRSSRDIV
LTEIIHVDSTQAIPKRYHRNSLIGDLQEDPKAAALFNQMMQQGLANTPFASSGEFNSEMIMALLRYMPLRAL
VNFSRGSFSEEDLDKLLDQLNSAG

J05-SEQ ID NO: 4

KAIAQVLFPALRWKDGSGFDHEEQRIEEALRIGVGGFILFGGEAAAVRELTSDLRRRSRTPLLIGADLERGAGQ
QFRGATQLPPAAALAALDDLDITRRAGELTAREARALGVDWVYAPVADLDLEPRNPIVGTRSFGADPARAA
AHVTAWIEGCRAGGALSCAKHFPGHGRTLADSHAELPVVAAERHELETDLAPFRAAIRAGVDAVMTAHVAF
PALDPSGAPATLSSAIIQGLLRDELGFHGAVSTDALNMQGVIEGGGEGGAAAVRALAAGCDVLLYPAEPAAA
AAALEDALGGALPHARAEAALAAIARLRQRANTMTPQNAEWGRAEDHAWALSVAERTLRVVRGEPLRLPD
ALDLLTVDDDVGGPFPPGPRDAFPATLRSSGAEVTEVAQPTPGRPLVIAVYADIRGWKGRAGLSTRAVAAVA
NALEVAPDATVVLFGHPRLAAELPAKATHVLAAWGGERLMQEAAARRLAAGRTDE

J06-SEQ ID NO: 5

AIIQFPQGFVWGTATASYQIEGAYDEDGRGLSIWDTFSHTPGNIRNGDNGDVACDSYHRYEEDIELIKNLGTK
AYRFSIAWPRIIPDGDGAVNPKGVAYYHKFIDKLLEAGVEPYVTIYHWDLPQALQDKGGWTSRATIDAFVRY
AEVLFKEYGGKVKKWITLNEPWCASFLSYTIGEHAPGYRDLQMGVDAAHNLMVAHGKTVRRFRELGISGEI
GFAPNVTWKVPFSTRPEDAEEAARREMGWQNDWFLDPVFKGEYPQYLIGIFEKHGAKLHVQPGDMELIREP
LDFYCINYYSGNMVRHRDGAGMFDAEYVDYGRDRTEMGWIIMPEGLSSVLLHFKQKYGDMPVYISENGAC
YNDEPGPDGRVRDDRRIDYLRSHIAELGRAIASGVNLKGYFLWSLLDNFEWAFGYEKRFGIVHVDFRTLKRTP
KDSYYWYQKVVKNNWLEV

J07-SEQ ID NO: 6

AIIRFPDGFHWGTATAAYQIEGAWNEDGRGPSIWDTFSHTPGKVKNGDNGDVACDSYHRIEEDVRLLKELG
VTCYRFSISWPRVIPAGVGDVNPKGLDYYRRLVDRLLENGIEPFCTLYHWDLPQALQDRGGWANRDTIRAFA
DYAELMFKTFAGKIRFWLTINEPWCVSFLSNFLGVHAPGNRDLQLATDISHHLLVAHAEAVRRFRQLGIEGQI
GIVPNVTWVEPYSNRPEDVEACRRATGWFVEWFLDPVFRGEYPDFLLEWFRAKGVAPRVADGDLEVIRGSV
DFLGVNYYTGNVGRYKENEGLFDCEEIDEGYERTDIGWPIYPEGLYRVLTYMTQRYGRVPIYITENGACYNHE
PEDGRVRDGKRIDYLRKHLIQLHRCLSSGVDVRGYMLWSLLDNFEWAEGYSKRFGIVFVDFDTLERIPKDSYY
WYRKVIRNNWLDV

J08-SEQ ID NO: 7

SQPRTDLAPGRFPADFTWGTATAAYQIEGAVREDGRGESIWDRFSHTPGKTHNGDTGDVACDHYHRWQG
DIELMRRLHVNAYRFSIAWPRILPEGWGRVNPPGLDFYDRLVDGLLAAGITPWVTLYHWDLPQALEDRGG
WPNPDTSKAFAEYADVVTRRLGDRVKHWITLNEPWVVAFLGYFTGEHAPGRKEPESYLPVVHNLLLAHGLA
VPVIRENSRDSQVGITLNLTHAYPAGDSAEDEAAARRLDGFMNRWFLDPLFTGGYPRDMIDVFGSWVPSFD

-continued

Table of Illustrative Sequences

ESDLGVIGAPLDFLGVNYYSPSFVRHSEGNPPLHVEQVRVDGEYTDMGWLVYPQGLYDLLTRLHRDYSPAAI
VITENGAAYPDEPPVEGRVHDPKRVEYYASHLDAAQRAIRDGVPLRGYFAWSLMDNFEWAFGYSKRFGLYY
VDYETLERTIKDSGLWYSRVVAEGQLVPTESVA

J09-SEQ ID NO: 8
SQPRTDLAPGRFPADFTWGTATAAYQIEGAVREDGRGESIWDRFSHTPGKTHNGDTGDVACDHYHRWQG
DIELMRRLHVNAYRFSIAWPRILPEGWGRVNPPGLDFYDRLVDGLLAAGITPWVTLYHWDLPQALEDRGG
WPNPDTSKAFAEYADVVTRRLGDRVKHWITLNEPWVVAFLGYFTGEHAPGRKEPEVYLPVVHNLLLAHGLA
VPIIRENSRDSQVGITLNLTHAYPAGDSAEDEAAARRMDGFMNRWFLDPLFTRGYPRDMVDVFGSWVPSF
DESDLGVIGAPLDFLGVNYYSPSFVRHSEGNPPLHVEQVRVDGEYTDMGWLVYPQGLYDLLTRLHRDYSPA
AIVITENGAAYPDEPPVEGRVHDPKRVEYYASHLDAAQRAIRDGVPLRGYFAWSLMDNFEWAFGYSKRFGL
YYVDYETLERTIKDSGLWYSRVVAEGQLVPTESVA

J11-SEQ ID NO: 9
ENNLLGRLTLEEKAALLEGTDAWYTNPVPRLGIPQLHLTDGPHGVRKVRSAGGGFSVSANEPATAFPTSATV
ASSWNPELARRMGEAIAEECLAAGVDVLLAPGINIKRSPLCGRNFEYYSEDPLVSAAFGTAFVRGVQSRGVG
CCVKHFAVNSSENFRFVGNSVVDERALREIYLRAFESVVKNAEPYAVMCSYNQINGTFASRNRRLLTDILRHE
WGFDGVVITDWGATCDRVEGLLAGCDLDMPGGVWHNRKSIIEAARSGRLPAEVLDASVRRMLRMIERCRS
GKPQAVSAKPDAPEQGKAGPGAHPDLGKHAELACKIARESAVLLKNDGTLPLHGGERLLVVGEMFEKMRF
QGAGSSLVQPTRVITPKEAFDRRGVTYVYEKGYRCFDPRRDARLEQAAVRAAEEADVILFFGGLTDLEESEGF
DREHMRLGDNQTELMNLLLATGKKMVLVLFAGAPVELPFFDGLSALLHMVLPGMCGGEAAAALLFGEATP
SGKLAESWPLRPEDTSCHADYNRGPVARYYESIYVGYRFYDKAGTKLRFPFGYGLSYTTFRYANMSVREESGR
IVVTADISNTGSRSGAEVVQLYVRAKSGAVFRPDKELVAFAKVYLQPGETKKVELAFDKEELSFWHVGLGRRV
LENGVYELLLAASAADIRLTAELRVTDGEEAGNPYPPEVVEAYAMPPRDIPPCFDRMAGYADAPETPSPGRK
KNRKPAFTMETPLMEFRRAWTGRLFYNTVMRSIRREYENALKMPDSLERDSRIKNTHFLIRMLPFESIRTMC
MSSSGALPYHVAEAVVELANGRWLRGLSLLMKKEKPIPLPKETAQRSADG

J14-SEQ ID NO: 10
ASALWRREDGVTYRDLNKNGKLDPYEDPRLPVEARIEDLLGRMTLEEKAGMLFHTGLGMNPDGTLQEGDG
TFGRASTTELVTQKLLNHFNVWAVADPRPMAEWYNRLQALAEGTRLGIPVTISSDPRHSYSNNPAASLFAGR
FSQWPEPIGLAAIGDDELVRAFGDIARQEYLAVGIRVALHPMADLATEPRWARIAGTFGEDAHLAARLVAAY
IRGFQGEHLGAHSVACMTKHFPGGGPQQDGEDPHFPYGREQVYPGNNFEYHLIPFEAAFEAGTAQIMPYY
GMPVGLPLEEVGFGFNRDVIAGLLRQRYGFQGVVCTDWGLLTDHRMGDRVLPARAWGVEHLSLEDRVLK
ALDAGVDQFGGESCPEVVVQLVRSGRLPEERLDVSVRRLLRDKFRLGLFDNPFVDPEEAERVVGQEAFVRAG
EAAQRRSIVLLTNGETSGGRMLPLREGLRLYVEGVDPQVASRYAQVVDTPEGADAAFIRLQAPHEHRDNLPL
EAFFHAGDLSFPEPELRRILDLLRRVPTVVQIYLDRPAVIPEIARESAALLADFGASDEAVLDVAFGRHKPGGRL
PFEMPSSMDAVRKQLPDVPCDSEDPLFPLGHGLTW

J15-SEQ ID NO: 11
PRARTPPYRDPTLPPEERVADLLARMTLEEKAAQMLCVWQKKAETLVDEQGNFDPARAEAAFGHGHGLGQ
VGRPSDSGGGKDARAMAELTNAIQKFFIERSRLGIPVIFHEECLHGHAAVDATSFPQPIALAGTFDPELVQQV
YACTAEEARLRGTHQALTPVLDVARDPRWGRVEETFGEDPYLVAQMGIAAVRGFQGDRTFRDRKHLIATLK
HFAAHGQPESGMNCAPANVSMRVLRETFLYPFRQAIREAGAISVMASYNEIDGVPSHANRWLLRDVLRKE
WGFDGFVVSDYYAIWELSERPDTHGHFVAADKREACALAVRAGVNIELPEPDCYLHLVDLVREGVLSEAELD
ELVAPILLWKFRLGLFDDPYVDPEEAARVVGCDANRELALRAARDAITLLKNENGLLPLDPDRITTIAVIGPNA
HRVLLGGYSGVPKHYVTVLDGIRARVGDRVEVLYAEGCKITVGGSWNQDEVVLPDPEEDRRQIQEAVEVAR
RADVVILAIGENEQVSREAWSRQHLGDRASLDLVGRQQELADALLATGKPVVVLLFNGRPLSVPALAERAPA
LLECWYLGQETGRAVAEVLFGDHNPGGKLPITIPRSVGHLPAYYNYKPSARRGYLFDDVSPLFPFGYGLSYTTF
ElRNVRLEDPVIPTSGSTRVLADVTNTGPREGTEVVQLYIRDRVSSVTRPVKELKGFVKVRLRPGETRTVALDIT
PESLAFYNIDMEWVVEPGEFEIMVGTSSRDSDLTKVVLQVRD

J16-SEQ ID NO: 12
QERPAYLDPTLPIEVRVEDLLGRMTLEEKVAQMLSMRQTKRLIVDEQNRFDPSRAPEWFKLGIGRIERPSEYF
QTAREAAAFTNAIQRWVRENTRLGIPVIFHEEALHGLRAAEATSYPQAIALASTWNPALVERVYGRIAREVRA
RGVHQVLAPVVDVGREPRWGRIEETFGEDPYLVAEMGKAAVWGLQGRRVPPVGPGHVIATLKHMAGHG
QPESGINVAPVFFGERHLREVFLYPFREAVEKAHALSVMASYNEIDGIPSHANAWMLRDVLRGEWGFRGVI
VSDWHGIPQLITRHHVAENLEEAARLALQATVDVELPDYEAYATLVDQVRRELIPELAVDEAVRRLLWAKFA
VGLFDGEPYVDEAEASRVNASEEDRALALEAAREAIILLKNDGLLPLEAGRLDRVAVIGPHAGEVLLGGYSGRP
RYTVSILEGLRERLRGEAEVLYAEGVRITEDSVFTDEPQPHFGGTWAQQRNAAHRVVFTPPEANRSRIEEAVA
LARTSDVVVLVVGGNEQTAREAYAPYHLGDRLSLRLPGQQEELVKAVLATGVPVVLVVIGGQPYVITELVDRV
GAIVWGWYLGQETGRAVAEVLLGDYNPAGRLPITIPRHEGQLPAYYSHKPSKELDYVDGPSRPLFPFGYGLSY
TRFAYRSVRLEPDRVGGCGVVRVLVELENVGDRAGDEVVQVYVRDRVSSVARPVKELKGFRRVHLGPGERK
VVEIELGPEAFAFYGLEMERVVEAGWFDVLVGGNSEELISVPLEITEGCNLGR

J17-SEQ ID NO: 13
LSGESMIGVPLEGFADFCRKVAAEGAVLLKNDGGVLPLAEGDRVSVFGRIQINYYRSGTGSGGSVNVPYTTNL
LDGLRGKAKIRVNEDLARVYEKWVKENPFDNGGGGWAKEPWHQKEMPLSDELVADARSKSDKAVVVIGR
TAGEDKDNAPAPGSWYLTEEEMAMLEAVTRHFDKTIVVLNVSNIIDMEWVNDSRFVHPISAVIYAWHGGM
EGGNAIADVLAGDAAPSGKLTDTIAISIGDYPSTANYGGEEKNVYQEDIYVGYRYFETFCPEKVRYPFGFGLSY
TDFSIDGLQAESVIKDGLPRIDVRVKVTNAGRLHAGKEVVQVYVEAPQGKLGKPAKALAAFAKTRLLAPGESE
ELVITFPLARIASYDDAGLTGHRSAYVLEEGTYRIHAGTSVRHTVPVPVDGRDGFTLDRLLVVEQLEEALAPKE
AFRRMKPGGRKPDGTYELAWEETPTRTVDPARRIADRLPPAIPQTGDRGYTLKDVHEGTISMETFIAQLSDD
DLAAIVRGEGMSHPLVTPGTASAFGGVTERLRKFGIPLGCAADGPSGIRMDSGHKATQVPIGTLLAATWDP
ALVEELYVLEGRELVRNRIDTLLGPGINLRRHPLNGRNFEYFSEDPLITGAFAAACVRGIKRGGSTATIKHFACN
NQEKNRTKVDAVVSERALRELYLKGFEIAVKEGGANAVMTAYNPVNGFWTASCYDLNTTILRGEWKFDGIV
MTDWWAMMNDPVVGGEPSRTNTGAMVRAQNDLYMVVPSFGAETNAMEDNTLECLAAGKLTRGELQR

-continued

| Table of Illustrative Sequences |
| --- |
| SAMNICRFLMQVPAFFRKQDFETEPSVAIRPAAAAPEGGARIVEIGDEAFVRPEDGAAVVLHVREGGAFRVA GRFRAEGLYVAQRSTNVLLNGERLATLSSNGTQNKWVERKLARAELEAGYYVLTLEHVKPGLGIDGIGFSRIR |
| J18-SEQ ID NO: 14 VATSAYQIEGATQEDGRGPSIWDTFARRPGAIRDGSTGEPACDHYHRYEEDIALMQSLGVGAYRFSVAWPRI LPEGRGRINPKGLAFYDRLVDRLLAAGITPFLTLYHWDLPQALEDRGGWRSRETAFAFAEYAEAVARALADR VPFFATLNEPWCSAFLGHWTGEHAPGLRNLEAALRAAHHLLLGHGLAVEALRAAGTKRVGIVLNFAPVYGE DPEAVDVADRYHNRYFLDPILGRGYPESPFQDPPPAPILSRDLEAIARPLDFLGVNYYAPVRVAPGTGPLPVRY LPPEGPVTAMGWEVYPEGLYHLLKRLGREVPWPLYITENGAAYPDLWTGEAVVEDPERVAYLEAHVEAALR AREEGVDLRGYFVWSLMDNFEWAFGYTRRFGLYYVDFPSQRRIPKRSALWYRERIARAQTGGSAR |
| J19-SEQ ID NO: 15 SAQSSPTWFLWGTATAAYQIEGAVHEDGRGPSIWDTFSHTPGKAFQGQTGDIACDHYHRWPQDIELMRQ LGAQAYRFSIAWPRIFPEGSGRVNERGLDFYDRLVDALLEASIVPFVTLYHWDLPQALQDRGGWAERATVEA FVTYAETVARRLGDRVRYWITHNEPWVVAYLGHYLGVHAPGISDLATAIRVSHHLLVSHGLAARAIRAVAPH AEVGITLNLSPVVPASDAVADQAAAKAYDGILNRWFLDPLFGRGYPSDTRRLLGAFYDPPESDCDTIAEPLDF LGVNYYTPAFVGSASDQSAGAFGIRLLSPEELHARGYELTDMGWAVVPDGLEQLLVHLHREYRPRAIFITENG AAFPDEVVDGVVADDRRIAYLVGHIAAVQRAREAGVPVHGYFVWSFLDNFEWAHGYSKRFGIVYVDYATLA RLPKASFHWYRQLIANGGLPDR |
| J24-SEQ ID NO: 16 VQNARRIAVNQIGYPAGSEKKAVFWDEGEFEVIDAASGAVVHRGATSALRRDEASGEAVAFGDFTPLDAPG RYFIRHVRTGERSATFGIGPSLYDDVHRGALKAFYFFRCGMELSEPFAGPWTHKACHLSDGIVYREPDRRLAG RGGWHDAGDYGKYTVPAAKAAADLLLACECYPGAFRKPVPLPETDGRTPDVLHEVRWELEFLFRMQDPAT GGAFHKLTTKQFPPLDLKPEDDLGDLYFLPVSPTATADFAAIMAMASRVYRPFDAAFADRCLAAALRAWAW LEAHPDAPHFKNPADVLTGEYGDDCGDDERFWAAAELYRATGEARFHDEVKRLAGLPFSKTELGWADVGG YGSIAYLLMDESAADPALRSALAAEWKARADRLAAAAGESGFAVALAPGDYVWGSNMLVMNRAMHLLIA HRLFGDPAHEKAALDQVHYLLGRNALDISFVTGFGDRHVRHPHYRPGVADGVEEPVPGFVSGGPNAGLQD EKAREALAGMPPARCFIDHQDSYSTNEVAIYWNSPAVFVLSHWVR |
| J25-SEQ ID NO: 17 ElMRAVLVLSLLWLSGCDWLFPDGDNGKEPEPEPEPTVELCGRWDARDVAGGRYRVINNVWGAETAQCIE VGLETGNFTITRADHDNGNNVAAYPAIYFGCHWGACTNNSGLPRRVQELSDVRTSWTLTPITTGRWNAAY DIWFSPGTNSSNGYSGGAELMIWLNWNGGVMPGGSRVATVELAGATWEVWYADWDWNYIAYRRTTPT TSVAELDLKVFIDDAVARGYIRPEWYLHAVETGFELWEGGAGLRSADFSVTVQ |
| J26-SEQ ID NO: 18 ETMRAILVLSLLWLSGCDWLFPDGDNGKEPEPEPEPTVELCGRWDARDVAGGRYRVINNVWGAETAQCIE VGLETGNFTITRADHDNGNDVAAYPAIYFGCHWGACTNNSGLPRRVQELSDVRTSWTLTPITTGRWNAAY DIWFSPVTNSSNGYSGGAELMIWLNWNGGVMPGGSRVATVELAGATWEVWYADWDWNYIAYRRTTPT TSVSELDLKAFIDDAVARGYIRPEWYLHAVETGFELWEGGAGLRSADFSVTVQ |
| J29-SEQ ID NO: 19 NETAGTEVPDSPMQRLVDAMQPGWNLGNTFDATDGDETSWGNPKVTRELIRAIRAQGYNSIRIPVTWNH RMGPGPDYEIREAFMERIQEVVDWCLEAGFIVIINMHHDSRWMHNMENEREEVLAKFRAAWKQIARHFR DYDPERLLFEGINEPRFSEDWNEDRPIYFQMVDELQTAFHETVRESGGKNGVRPLVLTTLTGGHAQARLDAL YETIRKLDDPNVIATVHYYGYYPFSVNMAGATTFGETARKDVIHNLGRVHDTFTARGIPVIIGEFGLLGFDKYV ETIQHGEVLKYLEFVTHFAREKRMAHMLWDNGQHFNRKELRWNNPDFHAIMMSTLTGRSSYTERDSVYIR KGEDVRDVSMRLYLNGNELTGVRAGDRALAPGADYEADGEQLVLKAGLLKSLLGDGLGPQADLTLSFSAGA DWVIHVIQYETPELKDSKMSRANFAIPAKFKGDRLATMEALYVGGGIAGPDDWTPFKEFGKSFDPDYTYGLI RIKQEFFNDVKDGDIKLTFHFWSGTKLDYLLTVSGGEVVGKAPAPEGEEASDEGGGGDPADAAETAAPADG GGTADGAVPADASPQGASNRTLFWGVLVIAALAALVGLMVFRSVKG |
| J30-SEQ ID NO: 20 LPEFPKIAVVAGSEAESVFRVVDIGTGDVVYEGRLSDSVYDDASGDTVRHADFGEWKRPGSYSVTVGRSSSA PFRIGNDVYRAPLIQAARSYTLARAGVAIDDPVTGLRHDVGHAQDKQAMLFFEDPFHRQGDPIDVSGGWY DAGDYGKYVPTGAVAAAQLMLAWEMRPELWRSLSLSLPAGLSEPERRAGLPDLLVEIKYELDWLLRMQRPD GAVYLKVAGGAWPGYIRPEEDTADRYVFGLSTYGTAQFAGAAAMGARVYAPFLPDYARKLLDAAIRAQRYL EQHPDPEFRYDEGQNNGSGPYEKRTDREERFWAAAELLRTTDDARYDAYIREHFSDFLEGKTSAVFWGNTV LLGQWAYVNAERADADHKASVRASLTAYADELVRWASANGYRSVLRPTDYFWGSAREAMGRAQALLLAD AVAPNRAYLETALDQAHWLFGRNAAGTSFMTGIGMHSPQKPHHRLVASTQTLIPGLVVGGPNAQGGDPI MDRLLRESDPRVFPAKAYVDDWEAYSVNEPAIDYTAPAVFVLTRFAEDR |
| J36-SEQ ID NO: 21 QPQKDNFYDDRIDTTAKAPPKETPRTYSLPFIRVEGNRFVDEQGRTVVFRGVSIADPDRLERLGRWSRRIFEV LKNDWNANIVRIPVHPRAWRARGEEAYLKLLDQAVEWANELGLYLIIDWHSIGNLRTELFQHPMYNTTKTE TFRFWKTIAEHFRHNPIVAFYEVFNEPTRFNGTLGRMSWEEYKQIVEDIIYIIYAHDRTVIPLVGGFDWAYDLT YVRESPIAFPGIAYTAHPYPQKRQPPWEEKWEHDWGFVADTYPVFVTELGFMSADEPGAHVPVIGDETYGE AIINYMEKKGISWTAWVFDPVWSPQLIKNWDFEPTTQGRFFREKMRQLNPRN |
| J27-SEQ ID NO: 22 AKPGVVADLTWYIPDTDKARSAQALRELGSRWVRLHVQWREAEPQPGVFDEWWMSEYGRALSAARAAG QKVIVMLSEAPTWARVAQGSAPRDPMLFAGFLERFAARFRGRVDAYEIWNEPNIARFWGPRPDPAAYTELL GAAHGALRRADPHARVVFGGLSGNDWRFLEAAYSAGAKGRFDVLAAHPYPYCGASGPGRSRRSGGRITAD SFTGYRELRASMLARGDAKPIWFTEFGWNTSTVKCNPGSGQWQGGVSEERQALYLRRAFKLVERDRYVKV AIWYNLRDNWWQRGADEPEARFGLLRADYSRKPAFYAFKAYARPKLRPRATTVTVALAPRPAAGRGVRIEG |

-continued

Table of Illustrative Sequences

AVRGADAGRVRIAVKRWAGKGWRLWQRRSARLDSEGRYRVPLKPLGPGRYRARARYLGTDLHRPSASRW
RSWRVAPTRPASAGDGALGARARPGS

J28-SEQ ID NO: 23
AFEIHRGTNISHWLSQSSARGEERRRWFTREDVERIAGMGLDHVRLPVDEEQLWDEHGRRDPEAFELLGNA
LEWCAEAGLRVVVDLHILRTHHFNDRQTPRLFTDPDEATRFAGLWRDLSDFLRAWDVNHVAYELLNEPVAR
DPERWHAVAFVAFSAIREVEPARTIVLGSNWFNSTEQFGVLRVPDDPHCILTFHYYKPMFITHYRASWWPG
GRYGGRVRYPGRPVPEEELEGLSDEDRRLVEAANAPYDRGVMASEIALPVRVAREHGMRLYCGEFGVYHRT
PREYRLAWYRDLLSVLREHDIAWANWDYKGEGFGIVTAERRPTDIA

J31-SEQ ID NO: 24
ETLEFLEVRNGKIVGARSGREIRLRGTNIGGWLNMENFlNGYAGTDQTVRHAMKEALGEAKAHFFFERMLD
YFFTEDDVLFLKENGLNCVRLPVNYRRFEDDERPYVYKEEGFRRLDEALRLCEKYGIYAIIDMHAVQGYQNTH
WHSDNASRHSFFWHDATCQQRFFALWRAIAERYRDRAVVAGYDLMNEPCTNTPYGDYPHTFYANYKPD
WERMNRIYRKAVAEIRSVDPQHIIFLEGDRYAYRFDGLEAPFAENLAYQSHNYHAAGFGPGPYPGVIRPNNP
DAVQGVYWDMEQQRKAFLEHEGTVFAKKHNVPLLVGEFGSVYNGPAEEVPDRLRSMDDQIAVFEENGAH
WTTWTYKDVGVMGLVTLDPESEYMQRIASFLEKKYRLGTDDWMHWLPAAAARQLVSGVAEYLRETIDESI
HSGFNRRALMQHVLCVYAATLLEPEYAKVFKGLSEQQLDEILQSFSFKQCVVNRDLAGILRKHAGAE

J32-SEQ ID NO: 25
SEDLQPIPHTDVNPLGVNTLLNEEADPEKVERTLDMIAAGGFTFVRQMFAWYEIEPAKGVYVDPHTGQDT
WEKYDRIVNLAHERGLEIIARLDKPPRWAREGQPGVDQVPDGPPNNDADYADFVRAVVTRYRGKVRYIQI
WNEPNLYGEWGGQPINPARFTELLKAAYTAAKEANPEVVVLLAGLAPTDCIRGPENLNEFLFLQGMYDAGA
KDYFDIATAMVYGYGYSPYDRRVEFERNNFSRVIQMREVMVRNGDADKPIWAAEYGWVSLPDDWTGDAS
VWGRPVSAETQARYLLQGYLRAQREWPWLGAMCVWLFRFPTSPTATPDAGRNPTRGFAIVNYDFSPTPAY
TTLAGSRARLDRAYTGAYPASTRLIQQDGGWMLTGEGASQTLVPAAAGATLRIPFSGPRLDLLLDGSGQGL
MVTIDGKPAPGLPAEETGAAIAVPDEDGRVTVADGLDDGPHVAEVRSLAGGDGSVALAGFVVVRQPWQS
WAYPWIYGTFAVMVVLTLASLVWNWRYRPAESPHPTRDGANGHLPRRLTAADLRARSRTRQSTTRRR

J35-SEQ ID NO: 26
EWLRLEGARIVRASDHSPFYLRGIAVGGWLNTENFINGYSGNESSWAEALEEELGSDAAEAFFQAIREHFFSE
EDVAYIRSLGATAIRIPFHWRYADPANVTYLDRVVEWARRYGVYVILDLHAVPGWQNPGWHCDNPYGVSL
FWRETFYQDQVIALWRFLADRYKDEPAIAGYDLLNEPYAPSNELVVSFFERLIRAIREVDRRHLLFVEGNRYAR
DFEGFERLLEVDDQIVFSSHNYMTPTHEGSSFPGWLEVDGRRIWIDESWIEAHYRTTNAWFLERNLACYVGE
FGALYDAPLDAPSSKDLARLRALEAQIALFNKLGVHWTLWTYKDLGAQGVRVIDPDSAYYRRIKPFLTLKMRL
GVEEWTSRGRGPLARRIRALLQEMEEEVVRLLQDYALAKRQLEEALLLSALYGHIAGALNPLLARLFAGLSSSEI
YEEVKEGVRFSRTKERTVLAEVLRROLAGGEETKGGGEA

What is claimed is:

1. A composition comprising (i) an isolated ionic liquid-tolerant cellulase having β-glucosidase activity and comprising an amino acid sequence having at least 95% sequence identity to the amino acid sequence of SEQ ID NO:4; and (ii) an ionic liquid, wherein the ionic liquid has an imidazolium cation.

2. The composition of claim 1, wherein the ionic liquid-tolerant cellulase comprises an amino acid sequence having at least 98% sequence identity to the amino acid sequence of SEQ ID NO:4.

3. The composition of claim 1, further comprising a lignocellulosic biomass.

4. The composition of claim 1, wherein the ionic liquid-tolerant cellulase comprises the amino acid sequence of SEQ ID NO:4.

5. A method of increasing the yield of soluble sugar from a lignocellulosic biomass, the method comprising incubating lignocellulosic biomass with a composition comprising an ionic liquid-tolerant cellulase and an ionic liquid having an imidazolium cation in an enzymatic hydrolysis reaction, wherein the ionic liquid-tolerant cellulase has β-glucosidase activity and comprises an amino acid sequence having at least 95% sequence identity to the amino acid sequence of SEQ ID NO:4.

6. The method of claim 5, wherein the ionic liquid-tolerant cellulase has at least 98% sequence identity to the amino acid sequence of SEQ ID NO:4.

7. The method of claim 5, wherein the lignocellulosic biomass is pretreated with ionic liquid.

8. The composition of claim 1, wherein the ionic liquid is 1-ethyl-3-methyl-imidazolium acetate ([$C_2$mim][OAc]).

9. The method of claim 5, wherein the ionic liquid-tolerant cellulase comprises the amino acid sequence of SEQ ID NO:4.

10. The method of claim 5, wherein the ionic liquid is [$C_2$mim][OAc].

* * * * *

SEQUENCE LISTING

<160> NUMBER OF SEQ ID NOS: 29

<210> SEQ ID NO 1
<211> LENGTH: 864
<212> TYPE: PRT
<213> ORGANISM: Artificial Sequence
<220> FEATURE:
<223> OTHER INFORMATION: synthetic cellulase with ORF J01 encoding beta-
glucosidase activity

<400> SEQUENCE: 1

Val Arg Met Glu Glu Leu Val Gly Arg Leu Thr Leu Glu Glu Lys Ala
1 5 10 15

Ala Leu Leu Glu Gly Ala Asp Ser Trp Tyr Thr Asn Pro Val Pro Arg
20 25 30

Leu Gly Ile Pro Arg Leu His Leu Thr Asp Gly Pro His Gly Val Arg
35 40 45

Gln Val Arg Arg Ala Gly Gly Gly Phe Ser Val Ser Asp Asn Glu Pro
50 55 60

Ala Thr Ala Phe Pro Thr Ser Ala Ala Val Ala Ser Ser Trp Asn Pro
65 70 75 80

Glu Leu Ala Arg Arg Met Gly Glu Ala Ile Ala Glu Glu Cys Leu Ala
85 90 95

Ala Gly Val Asp Val Leu Leu Ala Pro Gly Ile Asn Ile Lys Arg Ser
100 105 110

-continued

```
Pro Leu Cys Gly Arg Asn Phe Glu Tyr Tyr Ser Glu Asp Pro Leu Val
        115                 120                 125

Ser Ala Ala Phe Gly Ala Ala Phe Val Gln Gly Val Gln Ser Lys Gly
    130                 135                 140

Val Gly Cys Cys Val Lys His Phe Ala Val Asn Ser Asn Glu Thr Phe
145                 150                 155                 160

Arg Phe Val Gly Asp Ser Val Val Asp Glu Arg Ala Leu Arg Glu Ile
                165                 170                 175

Tyr Leu Arg Ala Phe Glu Ser Val Val Lys Asn Ala Lys Pro Tyr Ala
            180                 185                 190

Val Met Ser Ala Tyr Asn Lys Val Asn Gly Thr Phe Ala Ser Glu Asn
        195                 200                 205

Arg Leu Leu Leu Thr Asp Ile Leu Arg Arg Glu Trp Gly Phe Asp Gly
    210                 215                 220

Val Val Met Thr Asp Trp Gly Ala Thr Cys Asp Arg Val Glu Gly Leu
225                 230                 235                 240

Leu Ala Gly Cys Asp Leu Asp Met Pro Gly Gly Ser Trp His Asn Arg
                245                 250                 255

Lys Ala Ile Leu Glu Ala Ala Arg Ser Gly Arg Leu Ala Ala Asp Val
            260                 265                 270

Leu Asp Ala Ser Val Arg Arg Met Leu Arg Leu Ile Gly Arg Cys Arg
        275                 280                 285

Thr Gly Lys Ala Glu Arg Gln Ala Ala Pro Asp Phe Glu Lys His Ala
    290                 295                 300

Ala Leu Ala Cys Asp Ile Ala Lys Glu Ser Ala Val Leu Leu Lys Asn
305                 310                 315                 320

Asp Gly Thr Leu Pro Leu Ser Gly Gly Glu Arg Leu Leu Val Val Gly
                325                 330                 335

Glu Met Phe Glu Lys Met Arg Phe Gln Gly Ala Gly Ser Ser Leu Val
            340                 345                 350

His Pro Thr Asp Val Val Thr Pro Lys Asp Ala Phe Asp Arg Arg Gly
        355                 360                 365

Ile Ser Tyr Ala Tyr Glu Lys Gly Tyr Arg Ser Phe Asp Pro Gly Arg
    370                 375                 380

Asp Glu Arg Leu Glu Gln Ala Ala Val Arg Ala Ala Glu Asp Ala Asp
385                 390                 395                 400

Val Ile Leu Phe Phe Gly Gly Leu Thr Asp Phe Glu Glu Ser Glu Gly
                405                 410                 415

Phe Asp Arg Glu His Met Arg Leu Gly Asp Asn Gln Thr Ala Leu Leu
            420                 425                 430

Glu Lys Leu Ala Ala Thr Gly Lys Lys Leu Val Phe Val Leu Phe Ala
        435                 440                 445

Gly Ala Pro Val Glu Leu Pro Phe His Asp Glu Leu Ser Ala Leu Leu
    450                 455                 460

Tyr Met Val Leu Pro Gly Gln Arg Gly Gly Glu Ala Ala Ala Ala Leu
465                 470                 475                 480

Leu Tyr Gly Glu Ala Ala Pro Ser Gly Lys Leu Ala Glu Ser Trp Pro
                485                 490                 495

Met Arg Leu Glu Asp Thr Ser Cys Phe Ala Asp Tyr Asn Arg Gly Pro
            500                 505                 510

Val Ser Arg Tyr Tyr Glu Ser Ile Tyr Val Gly Tyr Arg Ala Tyr Asp
        515                 520                 525

Lys Ala Gly Thr Lys Leu Arg Phe Pro Phe Gly Phe Gly Leu Ser Tyr
```

```
    530                 535                 540

Thr Thr Phe Ala Tyr Ala Gly Met Thr Val Arg Glu Glu Asp Gly Arg
545                 550                 555                 560

Val Ala Val Ser Ala Asp Ile Thr Asn Thr Gly Lys Arg Arg Gly Ala
                565                 570                 575

Glu Val Val Gln Leu Tyr Val Arg His Lys Ala Ser Ala Val Phe Arg
            580                 585                 590

Pro Asp Lys Glu Leu Lys Ala Phe Ala Lys Val Phe Leu Glu Pro Gly
        595                 600                 605

Glu Thr Lys Arg Val Glu Leu Ala Phe Asp Lys Arg Asp Leu Ala Phe
    610                 615                 620

Trp His Ala Gly Leu Gly Arg Trp Val Val Glu Asn Gly Thr Tyr Glu
625                 630                 635                 640

Leu Leu Leu Ala Ala Ser Ala Ala Asp Val Arg Leu Ala Ala Glu Leu
                645                 650                 655

Ser Val Thr Asp Gly Glu Thr Ile Gly Gly Thr Val Pro His Pro Tyr
            660                 665                 670

Pro Pro Asp Val Ala Asp Ala Tyr Ala Met Pro Pro Lys Asp Val Pro
        675                 680                 685

Ala Cys Phe Gly Arg Leu Ala Gly Arg Ala Asp Ala Gly Asp Asp Pro
    690                 695                 700

Ala Asp Gly Gln Ala Gly Gly Phe His Gly Glu Thr Asp Lys Pro Leu
705                 710                 715                 720

Gly Lys Pro Asp Gly Ser Gly Gly Asp Gly Thr Gly Gly Asn Gly Pro
                725                 730                 735

Gly Gly Lys Ala Asp Gly Arg Arg Arg Pro Ser Gly Arg Arg Arg His
            740                 745                 750

Pro Pro Leu Thr Met Glu Thr Gln Leu Arg Asp Phe Arg Arg Thr Phe
        755                 760                 765

Gly Gly Arg Ile Phe Tyr Glu Met Val Met Arg Ser Val Arg Arg Glu
    770                 775                 780

Tyr Glu Ala Ala Leu Ala Met Pro Asp Ser Leu Glu Arg Asp Ser Arg
785                 790                 795                 800

Leu Lys Asn Thr His Phe Phe Leu Arg Leu Met Pro Leu Asn Thr Pro
                805                 810                 815

Arg Thr Met Ser Met Ser Ser Gly Gly Ala Phe Pro Tyr Arg Val Ala
            820                 825                 830

Glu Ala Leu Val Ala Leu Ala Asn Gly Gln Met Leu Lys Gly Leu Ser
        835                 840                 845

Leu Leu Met Lys Lys Glu Lys Pro Val Pro Leu Pro Lys Asp Ala Glu
    850                 855                 860


<210> SEQ ID NO 2
<211> LENGTH: 795
<212> TYPE: PRT
<213> ORGANISM: Artificial Sequence
<220> FEATURE:
<223> OTHER INFORMATION: synthetic cellulase with ORF J02 encoding beta-
      glucosidase activity

<400> SEQUENCE: 2

Val Ser Ser Glu Thr Phe Ala Tyr Lys Asp Ser Ser Leu Pro Ile Asp
1               5                   10                  15

Gln Arg Ile Asp Asp Leu Leu Ser Arg Met Ser Ile Asp Glu Lys Ile
            20                  25                  30
```

```
Ala Gln Leu Gly Cys Ile Trp Ser Thr Asp Leu Ile Arg Glu Gly Arg
        35                  40                  45

Phe Asp Pro Asp Tyr Ala Ile Ser Gln Ile Pro Asn Gly Ile Gly Gln
    50                  55                  60

Val Thr Arg Ile Gly Ala Ala Thr Gly Leu Arg Pro Asn Glu Ser Ala
65                  70                  75                  80

Asn Leu Met Asn Ser Ile Gln Lys Val Val Ile Glu Arg Thr Arg Leu
                85                  90                  95

Gly Ile Pro Val Phe Ile His Glu Glu Ser Val Gly Gly Phe Cys His
            100                 105                 110

Arg Asp Ala Thr Val Phe Pro Gln Ala Leu Gly Leu Ala Cys Ser Trp
        115                 120                 125

Asn Pro Glu Leu Ile Glu Lys Val Ala Gln Val Ile Arg Glu Gln Met
    130                 135                 140

Leu Ala Val Gly Ala Arg Leu Ala Leu Ala Pro Val Leu Asp Val Ala
145                 150                 155                 160

Arg Asp Pro Arg Trp Gly Arg Val Glu Glu Thr Tyr Gly Glu Asp Pro
                165                 170                 175

Val Leu Val Gly Thr Met Gly Thr Ala Tyr Ile Lys Gly Leu Gln Gly
            180                 185                 190

Asp Asp Leu Ala Gln Gly Val Ala Ala Thr Gly Lys His Phe Leu Ala
        195                 200                 205

Tyr Ser Phe Ser Leu Gly Gly Arg Asn Trp Gly Pro Val His Val Gly
    210                 215                 220

Pro Arg Glu Leu Arg Glu Val Tyr Ala Glu Pro Phe Ala Ala Ala Ile
225                 230                 235                 240

Arg Asp Ala Gly Leu Ser Val Ile Met Asn Ser Tyr Ala Ser Val Asp
                245                 250                 255

Gly Leu Pro Cys Ala Gly Ser Lys Ser Ile Leu Thr Asp Leu Leu Arg
            260                 265                 270

Lys Glu Leu Gly Phe Lys Gly Ser Val Val Ala Asp Tyr Phe Ser Val
        275                 280                 285

Glu Met Leu Arg Ser Phe His Lys Val Ala Ala Asp Lys Ser Glu Ala
    290                 295                 300

Ala Cys Ile Ala Leu Asn Ala Gly Leu Asp Met Glu Leu Pro Ala Leu
305                 310                 315                 320

Asp Cys Phe Gly Glu Pro Leu Lys Lys Ala Ile Glu Ala Gly Ser Ile
                325                 330                 335

Asn Ile Glu Val Ile Asp Thr Ala Val Arg Arg Val Leu Glu Leu Lys
            340                 345                 350

Phe Arg Leu Gly Leu Phe Glu Asn Pro Tyr Val Asp Ala Gly Val Thr
        355                 360                 365

Ser Ser Lys Phe Gln Thr Pro Glu Gln Arg Gln Leu Ala Tyr Gln Ala
    370                 375                 380

Ala Ala Glu Ser Val Val Leu Leu Lys Asn Asp Gly Val Leu Pro Ile
385                 390                 395                 400

Ser Lys Asp Asp Val Lys Ser Ile Ala Val Ile Gly Pro Ala Ala Asp
                405                 410                 415

Asp Lys Arg Leu Leu Gln Gly Asp Tyr His Tyr Pro Ala His Leu Glu
            420                 425                 430

Ser Leu Phe Glu Ser Gln Ser Asp Thr Glu Ser Leu Gly Leu Leu Ser
        435                 440                 445

Glu Glu Pro Ala Pro Thr Pro Ala Gly Gln Leu Asn Leu Gly Asn Phe
```

```
    450                 455                 460

Ala Pro Gly Pro Tyr Tyr Thr Pro His Val Thr Pro Leu Gln Ala Ile
465                 470                 475                 480

Arg Asp Lys His Pro Asp Ile Asp Val Ile Tyr Glu Lys Gly Cys Asp
                485                 490                 495

Ile Leu Gly Asp Asp Arg Ser Gly Phe Ala Ala Ala Val Asn Ala Ala
            500                 505                 510

Ser Asn Ala Asp Val Ser Ile Val Phe Val Gly Gly Lys Ser Gly Leu
        515                 520                 525

Lys Arg Pro Ala Thr Ser Gly Glu Ala Asn Asp Ala Thr Ser Leu Ser
    530                 535                 540

Leu Thr Gly Val Gln Ala Asp Leu Val Arg Ala Ile Ala Glu Ala Ala
545                 550                 555                 560

Lys Lys Leu Val Val Val Val Ile Ser Gly Arg Val His Thr Leu Glu
                565                 570                 575

Asp Leu Val Asp Ser Thr Asn Ala Leu Ile Phe Cys Val Pro Pro Gly
            580                 585                 590

Glu Glu Gly Gly Asn Ala Ile Val Asp Val Leu Phe Gly Ser Val Cys
        595                 600                 605

Pro Ser Gly Lys Leu Pro Val Ser Phe Pro Arg Arg Val Gly Gln Val
    610                 615                 620

Pro Asp Tyr Phe Gly Gln Arg Asn Gly Gly Asp Arg Ala Met Phe Phe
625                 630                 635                 640

Gly Asp Tyr Ile Asp Ser Thr Val Asp Pro Leu Phe Pro Phe Gly Tyr
                645                 650                 655

Gly Leu Ser Tyr Thr His Phe Glu Tyr Ser Gln Pro Asn Ile Glu Val
            660                 665                 670

Gly Asp Thr Thr Lys Pro Thr Ala Ile Ser Phe Glu Ile Lys Asn Val
        675                 680                 685

Gly Glu Tyr Thr Gly Ser Glu Val Val Gln Leu Tyr Cys Gln Asp Val
    690                 695                 700

Val Ala Ser Val Ser Arg Pro Thr Asn Met Leu Leu Gly Phe Thr Lys
705                 710                 715                 720

Val Arg Leu Asp Pro Gly Gln Ser Lys Lys Leu Thr Phe Ile Val His
                725                 730                 735

Pro Ser Arg Leu Ala Phe Tyr Asn Glu Ala Met Gln Phe Val Thr Glu
            740                 745                 750

Pro Gly Gln Tyr Ile Phe Arg Val Gly Ser Ser Ser Val Asp Ile Arg
        755                 760                 765

His Glu Leu Asp Val Thr Leu Thr Gly Glu Ala Ala Tyr Tyr Asn Gln
    770                 775                 780

Arg Asp Val Val Ala Thr Thr Val Val Val Glu
785                 790                 795


<210> SEQ ID NO 3
<211> LENGTH: 755
<212> TYPE: PRT
<213> ORGANISM: Artificial Sequence
<220> FEATURE:
<223> OTHER INFORMATION: synthetic cellulase with ORF J03 encoding beta-
      glucosidase activity

<400> SEQUENCE: 3

Leu Thr Arg Asp Ile Lys Ser Leu Ile Ala Gln Met Thr Leu Glu Glu
1               5                   10                  15
```

```
Lys Ala Ser Leu Cys Ser Gly Leu Gly Phe Trp Asp Thr Lys Pro Ile
            20                  25                  30

Glu Arg Leu Gly Ile Pro Ser Ile Val Met Thr Asp Gly Pro His Gly
        35                  40                  45

Leu Arg Lys Gln Val Pro Gly Ser Gln Asn Phe Phe Asp Ser Val Pro
    50                  55                  60

Ala Thr Cys Phe Pro Thr Ala Ala Thr Ile Ala Cys Ser Trp Asp Arg
65                  70                  75                  80

Ser Leu Val Arg Glu Ile Gly Ile Ala Leu Gly Glu Glu Cys Gln Ala
                85                  90                  95

Glu Gly Val Ser Val Ile Leu Gly Pro Gly Val Asn Ile Lys Arg Ser
            100                 105                 110

Pro Leu Cys Gly Arg Asn Phe Glu Tyr Phe Ser Glu Asp Pro Phe Leu
        115                 120                 125

Ser Thr Glu Leu Ala Ala Ser Tyr Ile Glu Gly Val Gln Ser Gln Gly
    130                 135                 140

Val Gly Thr Ser Ile Lys His Phe Ala Ala Asn Asn Gln Glu His Arg
145                 150                 155                 160

Arg Met Ser Val Asn Ala Ile Val Asp Glu Arg Thr Leu Arg Glu Ile
                165                 170                 175

Tyr Leu Ala Ser Phe Glu Gly Ala Val Lys Lys Ser Lys Pro Trp Thr
            180                 185                 190

Val Met Cys Ala Tyr Asn Arg Leu Asn Gly Asp Tyr Cys Ser Glu Asn
        195                 200                 205

His Tyr Leu Leu Thr Lys Val Leu Arg Glu Asp Trp Gly Tyr Glu Gly
    210                 215                 220

Leu Val Val Ser Asp Trp Gly Ala Val Asn Glu Arg Val Lys Gly Leu
225                 230                 235                 240

Glu Ala Gly Leu Asp Leu Glu Met Pro Gly Asn Gly Gly Val Gly Asp
                245                 250                 255

Arg Lys Ile Ile Glu Ala Val Arg Ser Gly Glu Leu Ser Glu Glu Val
            260                 265                 270

Leu Asp Arg Ala Val Glu Arg Ile Leu Lys Leu Ile Phe Gln Ala Val
        275                 280                 285

Asp Asn Arg Lys Glu Asn Phe Arg Tyr Asp Ala Asp Ala His His Gln
    290                 295                 300

Leu Ala Arg Lys Ala Ala Arg Glu Ser Met Val Leu Leu Lys Asn Asp
305                 310                 315                 320

Asn Ser Ile Leu Pro Leu Arg Lys Glu Gly Thr Ile Ala Val Ile Gly
                325                 330                 335

Ala Phe Ala Lys His Pro Arg Phe Gln Gly Gly Gly Ser Ser His Val
            340                 345                 350

Asn Pro Thr Arg Ile Asp Ile Pro Tyr Asp Glu Ile Gln Lys Val Val
        355                 360                 365

Gly Asp Ser Val Arg Leu Leu Tyr Ser Asp Gly Tyr Gln Leu Gly Ser
    370                 375                 380

Asp Glu Val Asn Gln Pro Leu Ile Glu Glu Ala Arg Lys Ile Ala Ser
385                 390                 395                 400

Gln Ala Asn Val Ala Leu Ile Phe Ala Gly Leu Pro Glu Asn Tyr Glu
                405                 410                 415

Ser Glu Gly Tyr Asp Arg Val His Met Ser Met Pro Arg Ser His Leu
            420                 425                 430

Glu Leu Ile Gln Ala Val Ser Glu Ser Gln Pro Asn Thr Val Val Leu
```

```
        435                 440                 445

Leu Cys Asn Gly Ala Pro Val Glu Met Pro Trp Leu His Asn Val Pro
    450                 455                 460

Ala Val Leu Glu Cys Tyr Leu Gly Gly Gln Ala Val Gly Ser Ala Ile
465                 470                 475                 480

Ala Asp Leu Leu Phe Gly Glu Ala Ser Pro Cys Gly Lys Leu Ala Glu
                485                 490                 495

Thr Phe Pro Gln Lys Leu Ser Asp Asn Pro Ser Tyr Leu Asn Phe Pro
            500                 505                 510

Gly Glu Asp Asp Lys Val Glu Tyr Arg Glu Gly Ile Phe Val Gly Tyr
        515                 520                 525

Arg Tyr Tyr Asp Thr Lys Glu Ile Gln Pro Leu Phe Pro Phe Gly His
    530                 535                 540

Gly Leu Ser Tyr Thr Thr Phe Glu Tyr Ser Asp Leu Ser Val Asp Lys
545                 550                 555                 560

Lys Ser Ile Lys Asp Asn Glu Ile Val Asn Val Gln Val Thr Val Lys
                565                 570                 575

Asn Thr Gly Lys Phe Ala Gly Lys Glu Ile Val Gln Leu Tyr Val Arg
            580                 585                 590

Asp Leu Ala Ser Ser Val Arg Arg Pro Glu Lys Glu Leu Lys Gly Phe
        595                 600                 605

Glu Lys Val Asp Leu Gln Pro Gly Glu Glu Lys Thr Val Asn Phe Thr
    610                 615                 620

Leu Asp Lys Arg Ala Phe Ala Tyr Tyr Asn Val Asp Leu Ser Asp Trp
625                 630                 635                 640

Tyr Val Glu Thr Gly Glu Phe Glu Ile Cys Val Gly Arg Ser Ser Arg
                645                 650                 655

Asp Ile Val Leu Thr Glu Ile Ile His Val Asp Ser Thr Gln Ala Ile
            660                 665                 670

Pro Lys Arg Tyr His Arg Asn Ser Leu Ile Gly Asp Leu Gln Glu Asp
        675                 680                 685

Pro Lys Ala Ala Ala Leu Phe Asn Gln Met Met Gln Gln Gly Leu Ala
    690                 695                 700

Asn Thr Pro Phe Ala Ser Ser Gly Glu Phe Asn Ser Glu Met Ile Met
705                 710                 715                 720

Ala Leu Leu Arg Tyr Met Pro Leu Arg Ala Leu Val Asn Phe Ser Arg
                725                 730                 735

Gly Ser Phe Ser Glu Glu Asp Leu Asp Lys Leu Leu Asp Gln Leu Asn
            740                 745                 750

Ser Ala Gly
        755


<210> SEQ ID NO 4
<211> LENGTH: 485
<212> TYPE: PRT
<213> ORGANISM: Artificial Sequence
<220> FEATURE:
<223> OTHER INFORMATION: synthetic cellulase with ORF J05 encoding beta-
      glucosidase activity

<400> SEQUENCE: 4

Lys Ala Ile Ala Gln Val Leu Phe Pro Ala Leu Arg Trp Lys Asp Gly
1               5                   10                  15

Ser Gly Phe Asp His Glu Glu Gln Arg Ile Glu Glu Ala Leu Arg Ile
            20                  25                  30
```

```
Gly Val Gly Gly Phe Ile Leu Phe Gly Gly Glu Ala Ala Ala Val Arg
        35                  40                  45

Glu Leu Thr Ser Asp Leu Arg Arg Arg Ser Arg Thr Pro Leu Leu Ile
    50                  55                  60

Gly Ala Asp Leu Glu Arg Gly Ala Gly Gln Gln Phe Arg Gly Ala Thr
65                  70                  75                  80

Gln Leu Pro Pro Ala Ala Ala Leu Ala Ala Leu Asp Asp Leu Asp Ile
                85                  90                  95

Thr Arg Arg Ala Gly Glu Leu Thr Ala Arg Glu Ala Arg Ala Leu Gly
            100                 105                 110

Val Asp Trp Val Tyr Ala Pro Val Ala Asp Leu Asp Leu Glu Pro Arg
        115                 120                 125

Asn Pro Ile Val Gly Thr Arg Ser Phe Gly Ala Asp Pro Ala Arg Ala
    130                 135                 140

Ala Ala His Val Thr Ala Trp Ile Glu Gly Cys Arg Ala Gly Gly Ala
145                 150                 155                 160

Leu Ser Cys Ala Lys His Phe Pro Gly His Gly Arg Thr Leu Ala Asp
                165                 170                 175

Ser His Ala Glu Leu Pro Val Val Ala Ala Glu Arg His Glu Leu Glu
            180                 185                 190

Thr Asp Leu Ala Pro Phe Arg Ala Ala Ile Arg Ala Gly Val Asp Ala
        195                 200                 205

Val Met Thr Ala His Val Ala Phe Pro Ala Leu Asp Pro Ser Gly Ala
    210                 215                 220

Pro Ala Thr Leu Ser Ser Ala Ile Ile Gln Gly Leu Leu Arg Asp Glu
225                 230                 235                 240

Leu Gly Phe His Gly Ala Val Ser Thr Asp Ala Leu Asn Met Gln Gly
                245                 250                 255

Val Ile Glu Gly Gly Gly Glu Gly Gly Ala Ala Ala Val Arg Ala Leu
            260                 265                 270

Ala Ala Gly Cys Asp Val Leu Leu Tyr Pro Ala Glu Pro Ala Ala Ala
        275                 280                 285

Ala Ala Ala Leu Glu Asp Ala Leu Gly Gly Ala Leu Pro His Ala Arg
    290                 295                 300

Ala Glu Ala Ala Leu Ala Ala Ile Ala Arg Leu Arg Gln Arg Ala Asn
305                 310                 315                 320

Thr Met Thr Pro Gln Asn Ala Glu Trp Gly Arg Ala Glu Asp His Ala
                325                 330                 335

Trp Ala Leu Ser Val Ala Glu Arg Thr Leu Arg Val Val Arg Gly Glu
            340                 345                 350

Pro Leu Arg Leu Pro Asp Ala Leu Asp Leu Leu Thr Val Asp Asp Asp
        355                 360                 365

Val Gly Gly Pro Phe Pro Pro Gly Pro Arg Asp Ala Phe Pro Ala Thr
    370                 375                 380

Leu Arg Ser Ser Gly Ala Glu Val Thr Glu Val Ala Gln Pro Thr Pro
385                 390                 395                 400

Gly Arg Pro Leu Val Ile Ala Val Tyr Ala Asp Ile Arg Gly Trp Lys
                405                 410                 415

Gly Arg Ala Gly Leu Ser Thr Arg Ala Val Ala Ala Val Ala Asn Ala
            420                 425                 430

Leu Glu Val Ala Pro Asp Ala Thr Val Val Leu Phe Gly His Pro Arg
        435                 440                 445

Leu Ala Ala Glu Leu Pro Ala Lys Ala Thr His Val Leu Ala Ala Trp
```

```
    450                 455                 460

Gly Gly Glu Arg Leu Met Gln Glu Ala Ala Ala Arg Arg Leu Ala Ala
465                 470                 475                 480

Gly Arg Thr Asp Glu
                485


<210> SEQ ID NO 5
<211> LENGTH: 447
<212> TYPE: PRT
<213> ORGANISM: Artificial Sequence
<220> FEATURE:
<223> OTHER INFORMATION: synthetic cellulase with ORF J06 encoding beta-
      glucosidase activity

<400> SEQUENCE: 5

Ala Ile Ile Gln Phe Pro Gln Gly Phe Val Trp Gly Thr Ala Thr Ala
1               5                   10                  15

Ser Tyr Gln Ile Glu Gly Ala Tyr Asp Glu Asp Gly Arg Gly Leu Ser
            20                  25                  30

Ile Trp Asp Thr Phe Ser His Thr Pro Gly Asn Ile Arg Asn Gly Asp
        35                  40                  45

Asn Gly Asp Val Ala Cys Asp Ser Tyr His Arg Tyr Glu Glu Asp Ile
    50                  55                  60

Glu Leu Ile Lys Asn Leu Gly Thr Lys Ala Tyr Arg Phe Ser Ile Ala
65                  70                  75                  80

Trp Pro Arg Ile Ile Pro Asp Gly Asp Gly Ala Val Asn Pro Lys Gly
                85                  90                  95

Val Ala Tyr Tyr His Lys Phe Ile Asp Lys Leu Leu Glu Ala Gly Val
            100                 105                 110

Glu Pro Tyr Val Thr Ile Tyr His Trp Asp Leu Pro Gln Ala Leu Gln
        115                 120                 125

Asp Lys Gly Gly Trp Thr Ser Arg Ala Thr Ile Asp Ala Phe Val Arg
    130                 135                 140

Tyr Ala Glu Val Leu Phe Lys Glu Tyr Gly Gly Lys Val Lys Lys Trp
145                 150                 155                 160

Ile Thr Leu Asn Glu Pro Trp Cys Ala Ser Phe Leu Ser Tyr Thr Ile
                165                 170                 175

Gly Glu His Ala Pro Gly Tyr Arg Asp Leu Gln Met Gly Val Asp Ala
            180                 185                 190

Ala His Asn Leu Met Val Ala His Gly Lys Thr Val Arg Arg Phe Arg
        195                 200                 205

Glu Leu Gly Ile Ser Gly Glu Ile Gly Phe Ala Pro Asn Val Thr Trp
    210                 215                 220

Lys Val Pro Phe Ser Thr Arg Pro Glu Asp Ala Glu Ala Ala Arg Arg
225                 230                 235                 240

Glu Met Gly Trp Gln Asn Asp Trp Phe Leu Asp Pro Val Phe Lys Gly
                245                 250                 255

Glu Tyr Pro Gln Tyr Leu Ile Gly Ile Phe Glu Lys His Gly Ala Lys
            260                 265                 270

Leu His Val Gln Pro Gly Asp Met Glu Leu Ile Arg Glu Pro Leu Asp
        275                 280                 285

Phe Tyr Cys Ile Asn Tyr Tyr Ser Gly Asn Met Val Arg His Arg Asp
    290                 295                 300

Gly Ala Gly Met Phe Asp Ala Glu Tyr Val Asp Tyr Gly Arg Asp Arg
305                 310                 315                 320
```

```
Thr Glu Met Gly Trp Ile Ile Met Pro Glu Gly Leu Ser Ser Val Leu
                325                 330                 335

Leu His Phe Lys Gln Lys Tyr Gly Asp Met Pro Val Tyr Ile Ser Glu
            340                 345                 350

Asn Gly Ala Cys Tyr Asn Asp Glu Pro Gly Pro Asp Gly Arg Val Arg
        355                 360                 365

Asp Asp Arg Arg Ile Asp Tyr Leu Arg Ser His Ile Ala Glu Leu Gly
    370                 375                 380

Arg Ala Ile Ala Ser Gly Val Asn Leu Lys Gly Tyr Phe Leu Trp Ser
385                 390                 395                 400

Leu Leu Asp Asn Phe Glu Trp Ala Phe Gly Tyr Glu Lys Arg Phe Gly
                405                 410                 415

Ile Val His Val Asp Phe Arg Thr Leu Lys Arg Thr Pro Lys Asp Ser
            420                 425                 430

Tyr Tyr Trp Tyr Gln Lys Val Val Lys Asn Asn Trp Leu Glu Val
        435                 440                 445


<210> SEQ ID NO 6
<211> LENGTH: 446
<212> TYPE: PRT
<213> ORGANISM: Artificial Sequence
<220> FEATURE:
<223> OTHER INFORMATION: synthetic cellulase with ORF J07 encoding beta-
      glucosidase activity

<400> SEQUENCE: 6

Ala Ile Ile Arg Phe Pro Asp Gly Phe His Trp Gly Thr Ala Thr Ala
1               5                   10                  15

Ala Tyr Gln Ile Glu Gly Ala Trp Asn Glu Asp Gly Arg Gly Pro Ser
            20                  25                  30

Ile Trp Asp Thr Phe Ser His Thr Pro Gly Lys Val Lys Asn Gly Asp
        35                  40                  45

Asn Gly Asp Val Ala Cys Asp Ser Tyr His Arg Ile Glu Glu Asp Val
    50                  55                  60

Arg Leu Leu Lys Glu Leu Gly Val Thr Cys Tyr Arg Phe Ser Ile Ser
65                  70                  75                  80

Trp Pro Arg Val Ile Pro Ala Gly Val Gly Asp Val Asn Pro Lys Gly
                85                  90                  95

Leu Asp Tyr Tyr Arg Arg Leu Val Asp Arg Leu Leu Glu Asn Gly Ile
            100                 105                 110

Glu Pro Phe Cys Thr Leu Tyr His Trp Asp Leu Pro Gln Ala Leu Gln
        115                 120                 125

Asp Arg Gly Gly Trp Ala Asn Arg Asp Thr Ile Arg Ala Phe Ala Asp
    130                 135                 140

Tyr Ala Glu Leu Met Phe Lys Thr Phe Ala Gly Lys Ile Arg Phe Trp
145                 150                 155                 160

Leu Thr Ile Asn Glu Pro Trp Cys Val Ser Phe Leu Ser Asn Phe Leu
                165                 170                 175

Gly Val His Ala Pro Gly Asn Arg Asp Leu Gln Leu Ala Thr Asp Ile
            180                 185                 190

Ser His His Leu Leu Val Ala His Ala Glu Ala Val Arg Arg Phe Arg
        195                 200                 205

Gln Leu Gly Ile Glu Gly Gln Ile Gly Ile Val Pro Asn Val Thr Trp
    210                 215                 220

Val Glu Pro Tyr Ser Asn Arg Pro Glu Asp Val Glu Ala Cys Arg Arg
225                 230                 235                 240
```

```
Ala Thr Gly Trp Phe Val Glu Trp Phe Leu Asp Pro Val Phe Arg Gly
                245                 250                 255

Glu Tyr Pro Asp Phe Leu Leu Glu Trp Phe Arg Ala Lys Gly Val Ala
            260                 265                 270

Pro Arg Val Ala Asp Gly Asp Leu Glu Val Ile Arg Gly Ser Val Asp
        275                 280                 285

Phe Leu Gly Val Asn Tyr Tyr Thr Gly Asn Val Gly Arg Tyr Lys Glu
    290                 295                 300

Asn Glu Gly Leu Phe Asp Cys Glu Glu Ile Asp Glu Gly Tyr Glu Arg
305                 310                 315                 320

Thr Asp Ile Gly Trp Pro Ile Tyr Pro Glu Gly Leu Tyr Arg Val Leu
                325                 330                 335

Thr Tyr Met Thr Gln Arg Tyr Gly Arg Val Pro Ile Tyr Ile Thr Glu
            340                 345                 350

Asn Gly Ala Cys Tyr Asn His Glu Pro Glu Asp Gly Arg Val Arg Asp
        355                 360                 365

Gly Lys Arg Ile Asp Tyr Leu Arg Lys His Leu Ile Gln Leu His Arg
    370                 375                 380

Cys Leu Ser Ser Gly Val Asp Val Arg Gly Tyr Met Leu Trp Ser Leu
385                 390                 395                 400

Leu Asp Asn Phe Glu Trp Ala Glu Gly Tyr Ser Lys Arg Phe Gly Ile
                405                 410                 415

Val Phe Val Asp Phe Asp Thr Leu Glu Arg Ile Pro Lys Asp Ser Tyr
            420                 425                 430

Tyr Trp Tyr Arg Lys Val Ile Arg Asn Asn Trp Leu Asp Val
        435                 440                 445


<210> SEQ ID NO 7
<211> LENGTH: 457
<212> TYPE: PRT
<213> ORGANISM: Artificial Sequence
<220> FEATURE:
<223> OTHER INFORMATION: synthetic cellulase with ORF J08 encoding beta-
      glucosidase activity

<400> SEQUENCE: 7

Ser Gln Pro Arg Thr Asp Leu Ala Pro Gly Arg Phe Pro Ala Asp Phe
1               5                   10                  15

Thr Trp Gly Thr Ala Thr Ala Ala Tyr Gln Ile Glu Gly Ala Val Arg
            20                  25                  30

Glu Asp Gly Arg Gly Glu Ser Ile Trp Asp Arg Phe Ser His Thr Pro
        35                  40                  45

Gly Lys Thr His Asn Gly Asp Thr Gly Asp Val Ala Cys Asp His Tyr
    50                  55                  60

His Arg Trp Gln Gly Asp Ile Glu Leu Met Arg Arg Leu His Val Asn
65                  70                  75                  80

Ala Tyr Arg Phe Ser Ile Ala Trp Pro Arg Ile Leu Pro Glu Gly Trp
                85                  90                  95

Gly Arg Val Asn Pro Pro Gly Leu Asp Phe Tyr Asp Arg Leu Val Asp
            100                 105                 110

Gly Leu Leu Ala Ala Gly Ile Thr Pro Trp Val Thr Leu Tyr His Trp
        115                 120                 125

Asp Leu Pro Gln Ala Leu Glu Asp Arg Gly Gly Trp Pro Asn Pro Asp
    130                 135                 140

Thr Ser Lys Ala Phe Ala Glu Tyr Ala Asp Val Val Thr Arg Arg Leu
```

```
145                 150                 155                 160

Gly Asp Arg Val Lys His Trp Ile Thr Leu Asn Glu Pro Trp Val Val
                165                 170                 175

Ala Phe Leu Gly Tyr Phe Thr Gly Glu His Ala Pro Gly Arg Lys Glu
            180                 185                 190

Pro Glu Ser Tyr Leu Pro Val Val His Asn Leu Leu Leu Ala His Gly
        195                 200                 205

Leu Ala Val Pro Val Ile Arg Glu Asn Ser Arg Asp Ser Gln Val Gly
    210                 215                 220

Ile Thr Leu Asn Leu Thr His Ala Tyr Pro Ala Gly Asp Ser Ala Glu
225                 230                 235                 240

Asp Glu Ala Ala Ala Arg Arg Leu Asp Gly Phe Met Asn Arg Trp Phe
                245                 250                 255

Leu Asp Pro Leu Phe Thr Gly Gly Tyr Pro Arg Asp Met Ile Asp Val
            260                 265                 270

Phe Gly Ser Trp Val Pro Ser Phe Asp Glu Ser Asp Leu Gly Val Ile
        275                 280                 285

Gly Ala Pro Leu Asp Phe Leu Gly Val Asn Tyr Tyr Ser Pro Ser Phe
    290                 295                 300

Val Arg His Ser Glu Gly Asn Pro Pro Leu His Val Glu Gln Val Arg
305                 310                 315                 320

Val Asp Gly Glu Tyr Thr Asp Met Gly Trp Leu Val Tyr Pro Gln Gly
                325                 330                 335

Leu Tyr Asp Leu Leu Thr Arg Leu His Arg Asp Tyr Ser Pro Ala Ala
            340                 345                 350

Ile Val Ile Thr Glu Asn Gly Ala Ala Tyr Pro Asp Glu Pro Pro Val
        355                 360                 365

Glu Gly Arg Val His Asp Pro Lys Arg Val Glu Tyr Tyr Ala Ser His
    370                 375                 380

Leu Asp Ala Ala Gln Arg Ala Ile Arg Asp Gly Val Pro Leu Arg Gly
385                 390                 395                 400

Tyr Phe Ala Trp Ser Leu Met Asp Asn Phe Glu Trp Ala Phe Gly Tyr
                405                 410                 415

Ser Lys Arg Phe Gly Leu Tyr Tyr Val Asp Tyr Glu Thr Leu Glu Arg
            420                 425                 430

Thr Ile Lys Asp Ser Gly Leu Trp Tyr Ser Arg Val Val Ala Glu Gly
        435                 440                 445

Gln Leu Val Pro Thr Glu Ser Val Ala
    450                 455


<210> SEQ ID NO 8
<211> LENGTH: 457
<212> TYPE: PRT
<213> ORGANISM: Artificial Sequence
<220> FEATURE:
<223> OTHER INFORMATION: synthetic cellulase with ORF J09 encoding beta-
      glucosidase activity

<400> SEQUENCE: 8

Ser Gln Pro Arg Thr Asp Leu Ala Pro Gly Arg Phe Pro Ala Asp Phe
1               5                   10                  15

Thr Trp Gly Thr Ala Thr Ala Ala Tyr Gln Ile Glu Gly Ala Val Arg
            20                  25                  30

Glu Asp Gly Arg Gly Glu Ser Ile Trp Asp Arg Phe Ser His Thr Pro
        35                  40                  45
```

-continued

```
Gly Lys Thr His Asn Gly Asp Thr Gly Asp Val Ala Cys Asp His Tyr
    50                  55                  60

His Arg Trp Gln Gly Asp Ile Glu Leu Met Arg Arg Leu His Val Asn
65                  70                  75                  80

Ala Tyr Arg Phe Ser Ile Ala Trp Pro Arg Ile Leu Pro Glu Gly Trp
                85                  90                  95

Gly Arg Val Asn Pro Pro Gly Leu Asp Phe Tyr Asp Arg Leu Val Asp
            100                 105                 110

Gly Leu Leu Ala Ala Gly Ile Thr Pro Trp Val Thr Leu Tyr His Trp
        115                 120                 125

Asp Leu Pro Gln Ala Leu Glu Asp Arg Gly Gly Trp Pro Asn Pro Asp
    130                 135                 140

Thr Ser Lys Ala Phe Ala Glu Tyr Ala Asp Val Val Thr Arg Arg Leu
145                 150                 155                 160

Gly Asp Arg Val Lys His Trp Ile Thr Leu Asn Glu Pro Trp Val Val
                165                 170                 175

Ala Phe Leu Gly Tyr Phe Thr Gly Glu His Ala Pro Gly Arg Lys Glu
            180                 185                 190

Pro Glu Val Tyr Leu Pro Val Val His Asn Leu Leu Leu Ala His Gly
        195                 200                 205

Leu Ala Val Pro Ile Ile Arg Glu Asn Ser Arg Asp Ser Gln Val Gly
    210                 215                 220

Ile Thr Leu Asn Leu Thr His Ala Tyr Pro Ala Gly Asp Ser Ala Glu
225                 230                 235                 240

Asp Glu Ala Ala Ala Arg Arg Met Asp Gly Phe Met Asn Arg Trp Phe
                245                 250                 255

Leu Asp Pro Leu Phe Thr Arg Gly Tyr Pro Arg Asp Met Val Asp Val
            260                 265                 270

Phe Gly Ser Trp Val Pro Ser Phe Asp Glu Ser Asp Leu Gly Val Ile
        275                 280                 285

Gly Ala Pro Leu Asp Phe Leu Gly Val Asn Tyr Tyr Ser Pro Ser Phe
    290                 295                 300

Val Arg His Ser Glu Gly Asn Pro Pro Leu His Val Glu Gln Val Arg
305                 310                 315                 320

Val Asp Gly Glu Tyr Thr Asp Met Gly Trp Leu Val Tyr Pro Gln Gly
                325                 330                 335

Leu Tyr Asp Leu Leu Thr Arg Leu His Arg Asp Tyr Ser Pro Ala Ala
            340                 345                 350

Ile Val Ile Thr Glu Asn Gly Ala Ala Tyr Pro Asp Glu Pro Pro Val
        355                 360                 365

Glu Gly Arg Val His Asp Pro Lys Arg Val Glu Tyr Tyr Ala Ser His
    370                 375                 380

Leu Asp Ala Ala Gln Arg Ala Ile Arg Asp Gly Val Pro Leu Arg Gly
385                 390                 395                 400

Tyr Phe Ala Trp Ser Leu Met Asp Asn Phe Glu Trp Ala Phe Gly Tyr
                405                 410                 415

Ser Lys Arg Phe Gly Leu Tyr Tyr Val Asp Tyr Glu Thr Leu Glu Arg
            420                 425                 430

Thr Ile Lys Asp Ser Gly Leu Trp Tyr Ser Arg Val Val Ala Glu Gly
        435                 440                 445

Gln Leu Val Pro Thr Glu Ser Val Ala
    450                 455
```

```
<210> SEQ ID NO 9
<211> LENGTH: 840
<212> TYPE: PRT
<213> ORGANISM: Artificial Sequence
<220> FEATURE:
<223> OTHER INFORMATION: synthetic cellulase with ORF J11 encoding beta-
      glucosidase activity

<400> SEQUENCE: 9

Glu Asn Asn Leu Leu Gly Arg Leu Thr Leu Glu Glu Lys Ala Ala Leu
1               5                   10                  15

Leu Glu Gly Thr Asp Ala Trp Tyr Thr Asn Pro Val Pro Arg Leu Gly
            20                  25                  30

Ile Pro Gln Leu His Leu Thr Asp Gly Pro His Gly Val Arg Lys Val
        35                  40                  45

Arg Ser Ala Gly Gly Gly Phe Ser Val Ser Ala Asn Glu Pro Ala Thr
    50                  55                  60

Ala Phe Pro Thr Ser Ala Thr Val Ala Ser Ser Trp Asn Pro Glu Leu
65                  70                  75                  80

Ala Arg Arg Met Gly Glu Ala Ile Ala Glu Glu Cys Leu Ala Ala Gly
                85                  90                  95

Val Asp Val Leu Leu Ala Pro Gly Ile Asn Ile Lys Arg Ser Pro Leu
            100                 105                 110

Cys Gly Arg Asn Phe Glu Tyr Tyr Ser Glu Asp Pro Leu Val Ser Ala
        115                 120                 125

Ala Phe Gly Thr Ala Phe Val Arg Gly Val Gln Ser Arg Gly Val Gly
    130                 135                 140

Cys Cys Val Lys His Phe Ala Val Asn Ser Ser Glu Asn Phe Arg Phe
145                 150                 155                 160

Val Gly Asn Ser Val Val Asp Glu Arg Ala Leu Arg Glu Ile Tyr Leu
                165                 170                 175

Arg Ala Phe Glu Ser Val Val Lys Asn Ala Glu Pro Tyr Ala Val Met
            180                 185                 190

Cys Ser Tyr Asn Gln Ile Asn Gly Thr Phe Ala Ser Arg Asn Arg Arg
        195                 200                 205

Leu Leu Thr Asp Ile Leu Arg His Glu Trp Gly Phe Asp Gly Val Val
    210                 215                 220

Ile Thr Asp Trp Gly Ala Thr Cys Asp Arg Val Glu Gly Leu Leu Ala
225                 230                 235                 240

Gly Cys Asp Leu Asp Met Pro Gly Gly Val Trp His Asn Arg Lys Ser
                245                 250                 255

Ile Ile Glu Ala Ala Arg Ser Gly Arg Leu Pro Ala Glu Val Leu Asp
            260                 265                 270

Ala Ser Val Arg Arg Met Leu Arg Met Ile Glu Arg Cys Arg Ser Gly
        275                 280                 285

Lys Pro Gln Ala Val Ser Ala Lys Pro Asp Ala Pro Glu Gln Gly Lys
    290                 295                 300

Ala Gly Pro Gly Ala His Pro Asp Leu Gly Lys His Ala Glu Leu Ala
305                 310                 315                 320

Cys Lys Ile Ala Arg Glu Ser Ala Val Leu Leu Lys Asn Asp Gly Thr
                325                 330                 335

Leu Pro Leu His Gly Gly Glu Arg Leu Leu Val Val Gly Glu Met Phe
            340                 345                 350

Glu Lys Met Arg Phe Gln Gly Ala Gly Ser Ser Leu Val Gln Pro Thr
        355                 360                 365
```

```
Arg Val Ile Thr Pro Lys Glu Ala Phe Asp Arg Arg Gly Val Thr Tyr
    370                 375                 380

Val Tyr Glu Lys Gly Tyr Arg Cys Phe Asp Pro Arg Arg Asp Ala Arg
385                 390                 395                 400

Leu Glu Gln Ala Ala Val Arg Ala Ala Glu Glu Ala Asp Val Ile Leu
                405                 410                 415

Phe Phe Gly Gly Leu Thr Asp Leu Glu Glu Ser Glu Gly Phe Asp Arg
            420                 425                 430

Glu His Met Arg Leu Gly Asp Asn Gln Thr Glu Leu Met Asn Leu Leu
        435                 440                 445

Leu Ala Thr Gly Lys Lys Met Val Leu Val Leu Phe Ala Gly Ala Pro
    450                 455                 460

Val Glu Leu Pro Phe Phe Asp Gly Leu Ser Ala Leu Leu His Met Val
465                 470                 475                 480

Leu Pro Gly Met Cys Gly Gly Glu Ala Ala Ala Ala Leu Leu Phe Gly
                485                 490                 495

Glu Ala Thr Pro Ser Gly Lys Leu Ala Glu Ser Trp Pro Leu Arg Pro
            500                 505                 510

Glu Asp Thr Ser Cys His Ala Asp Tyr Asn Arg Gly Pro Val Ala Arg
        515                 520                 525

Tyr Tyr Glu Ser Ile Tyr Val Gly Tyr Arg Phe Tyr Asp Lys Ala Gly
    530                 535                 540

Thr Lys Leu Arg Phe Pro Phe Gly Tyr Gly Leu Ser Tyr Thr Thr Phe
545                 550                 555                 560

Arg Tyr Ala Asn Met Ser Val Arg Glu Glu Ser Gly Arg Ile Val Val
                565                 570                 575

Thr Ala Asp Ile Ser Asn Thr Gly Ser Arg Ser Gly Ala Glu Val Val
            580                 585                 590

Gln Leu Tyr Val Arg Ala Lys Ser Gly Ala Val Phe Arg Pro Asp Lys
        595                 600                 605

Glu Leu Val Ala Phe Ala Lys Val Tyr Leu Gln Pro Gly Glu Thr Lys
    610                 615                 620

Lys Val Glu Leu Ala Phe Asp Lys Glu Glu Leu Ser Phe Trp His Val
625                 630                 635                 640

Gly Leu Gly Arg Arg Val Leu Glu Asn Gly Val Tyr Glu Leu Leu Leu
                645                 650                 655

Ala Ala Ser Ala Ala Asp Ile Arg Leu Thr Ala Glu Leu Arg Val Thr
            660                 665                 670

Asp Gly Glu Glu Ala Gly Asn Pro Tyr Pro Pro Glu Val Val Glu Ala
        675                 680                 685

Tyr Ala Met Pro Pro Arg Asp Ile Pro Pro Cys Phe Asp Arg Met Ala
    690                 695                 700

Gly Tyr Ala Asp Ala Pro Glu Thr Pro Ser Pro Gly Arg Lys Lys Asn
705                 710                 715                 720

Arg Lys Pro Ala Phe Thr Met Glu Thr Pro Leu Met Glu Phe Arg Arg
                725                 730                 735

Ala Trp Thr Gly Arg Leu Phe Tyr Asn Thr Val Met Arg Ser Ile Arg
            740                 745                 750

Arg Glu Tyr Glu Asn Ala Leu Lys Met Pro Asp Ser Leu Glu Arg Asp
        755                 760                 765

Ser Arg Ile Lys Asn Thr His Phe Leu Ile Arg Met Leu Pro Phe Glu
    770                 775                 780

Ser Ile Arg Thr Met Cys Met Ser Ser Ser Gly Ala Leu Pro Tyr His
```

```
785                 790                 795                 800

Val Ala Glu Ala Val Val Glu Leu Ala Asn Gly Arg Trp Leu Arg Gly
                805                 810                 815

Leu Ser Leu Leu Met Lys Lys Glu Lys Pro Ile Pro Leu Pro Lys Glu
            820                 825                 830

Thr Ala Gln Arg Ser Ala Asp Gly
        835                 840


<210> SEQ ID NO 10
<211> LENGTH: 607
<212> TYPE: PRT
<213> ORGANISM: Artificial Sequence
<220> FEATURE:
<223> OTHER INFORMATION: synthetic cellulase with ORF J14 encoding beta-
      glucosidase activity

<400> SEQUENCE: 10

Ala Ser Ala Leu Trp Arg Arg Glu Asp Gly Val Thr Tyr Arg Asp Leu
1               5                   10                  15

Asn Lys Asn Gly Lys Leu Asp Pro Tyr Glu Asp Pro Arg Leu Pro Val
            20                  25                  30

Glu Ala Arg Ile Glu Asp Leu Leu Gly Arg Met Thr Leu Glu Glu Lys
        35                  40                  45

Ala Gly Met Leu Phe His Thr Gly Leu Gly Met Asn Pro Asp Gly Thr
    50                  55                  60

Leu Gln Glu Gly Asp Gly Thr Phe Gly Arg Ala Ser Thr Thr Glu Leu
65                  70                  75                  80

Val Thr Gln Lys Leu Leu Asn His Phe Asn Val Trp Ala Val Ala Asp
                85                  90                  95

Pro Arg Pro Met Ala Glu Trp Tyr Asn Arg Leu Gln Ala Leu Ala Glu
            100                 105                 110

Gly Thr Arg Leu Gly Ile Pro Val Thr Ile Ser Ser Asp Pro Arg His
        115                 120                 125

Ser Tyr Ser Asn Asn Pro Ala Ala Ser Leu Phe Ala Gly Arg Phe Ser
    130                 135                 140

Gln Trp Pro Glu Pro Ile Gly Leu Ala Ala Ile Gly Asp Asp Glu Leu
145                 150                 155                 160

Val Arg Ala Phe Gly Asp Ile Ala Arg Gln Glu Tyr Leu Ala Val Gly
                165                 170                 175

Ile Arg Val Ala Leu His Pro Met Ala Asp Leu Ala Thr Glu Pro Arg
            180                 185                 190

Trp Ala Arg Ile Ala Gly Thr Phe Gly Glu Asp Ala His Leu Ala Ala
        195                 200                 205

Arg Leu Val Ala Ala Tyr Ile Arg Gly Phe Gln Gly Glu His Leu Gly
    210                 215                 220

Ala His Ser Val Ala Cys Met Thr Lys His Phe Pro Gly Gly Gly Pro
225                 230                 235                 240

Gln Gln Asp Gly Glu Asp Pro His Phe Pro Tyr Gly Arg Glu Gln Val
                245                 250                 255

Tyr Pro Gly Asn Asn Phe Glu Tyr His Leu Ile Pro Phe Glu Ala Ala
            260                 265                 270

Phe Glu Ala Gly Thr Ala Gln Ile Met Pro Tyr Tyr Gly Met Pro Val
        275                 280                 285

Gly Leu Pro Leu Glu Glu Val Gly Phe Gly Phe Asn Arg Asp Val Ile
    290                 295                 300
```

```
Ala Gly Leu Leu Arg Gln Arg Tyr Gly Phe Gln Gly Val Val Cys Thr
305                 310                 315                 320

Asp Trp Gly Leu Leu Thr Asp His Arg Met Gly Asp Arg Val Leu Pro
                325                 330                 335

Ala Arg Ala Trp Gly Val Glu His Leu Ser Leu Glu Asp Arg Val Leu
            340                 345                 350

Lys Ala Leu Asp Ala Gly Val Asp Gln Phe Gly Gly Glu Ser Cys Pro
        355                 360                 365

Glu Val Val Val Gln Leu Val Arg Ser Gly Arg Leu Pro Glu Glu Arg
    370                 375                 380

Leu Asp Val Ser Val Arg Arg Leu Leu Arg Asp Lys Phe Arg Leu Gly
385                 390                 395                 400

Leu Phe Asp Asn Pro Phe Val Asp Pro Glu Glu Ala Glu Arg Val Val
                405                 410                 415

Gly Gln Glu Ala Phe Val Arg Ala Gly Glu Ala Ala Gln Arg Arg Ser
            420                 425                 430

Ile Val Leu Leu Thr Asn Gly Glu Thr Ser Gly Gly Arg Met Leu Pro
        435                 440                 445

Leu Arg Glu Gly Leu Arg Leu Tyr Val Glu Gly Val Asp Pro Gln Val
    450                 455                 460

Ala Ser Arg Tyr Ala Gln Val Val Asp Thr Pro Glu Gly Ala Asp Ala
465                 470                 475                 480

Ala Phe Ile Arg Leu Gln Ala Pro His Glu His Arg Asp Asn Leu Pro
                485                 490                 495

Leu Glu Ala Phe Phe His Ala Gly Asp Leu Ser Phe Pro Glu Pro Glu
            500                 505                 510

Leu Arg Arg Ile Leu Asp Leu Leu Arg Arg Val Pro Thr Val Val Gln
        515                 520                 525

Ile Tyr Leu Asp Arg Pro Ala Val Ile Pro Glu Ile Ala Arg Glu Ser
    530                 535                 540

Ala Ala Leu Leu Ala Asp Phe Gly Ala Ser Asp Glu Ala Val Leu Asp
545                 550                 555                 560

Val Ala Phe Gly Arg His Lys Pro Gly Gly Arg Leu Pro Phe Glu Met
                565                 570                 575

Pro Ser Ser Met Asp Ala Val Arg Lys Gln Leu Pro Asp Val Pro Cys
            580                 585                 590

Asp Ser Glu Asp Pro Leu Phe Pro Leu Gly His Gly Leu Thr Trp
        595                 600                 605
```

<210> SEQ ID NO 11
<211> LENGTH: 764
<212> TYPE: PRT
<213> ORGANISM: Artificial Sequence
<220> FEATURE:
<223> OTHER INFORMATION: synthetic cellulase with ORF J15 encoding beta-glucosidase activity

<400> SEQUENCE: 11

```
Pro Arg Ala Arg Thr Pro Pro Tyr Arg Asp Pro Thr Leu Pro Pro Glu
1               5                   10                  15

Glu Arg Val Ala Asp Leu Leu Ala Arg Met Thr Leu Glu Glu Lys Ala
            20                  25                  30

Ala Gln Met Leu Cys Val Trp Gln Lys Lys Ala Glu Thr Leu Val Asp
        35                  40                  45

Glu Gln Gly Asn Phe Asp Pro Ala Arg Ala Glu Ala Ala Phe Gly His
    50                  55                  60
```

```
Gly His Gly Leu Gly Gln Val Gly Arg Pro Ser Asp Ser Gly Gly Gly
65                  70                  75                  80

Lys Asp Ala Arg Ala Met Ala Glu Leu Thr Asn Ala Ile Gln Lys Phe
                85                  90                  95

Phe Ile Glu Arg Ser Arg Leu Gly Ile Pro Val Ile Phe His Glu Glu
            100                 105                 110

Cys Leu His Gly His Ala Ala Val Asp Ala Thr Ser Phe Pro Gln Pro
        115                 120                 125

Ile Ala Leu Ala Gly Thr Phe Asp Pro Glu Leu Val Gln Gln Val Tyr
    130                 135                 140

Ala Cys Thr Ala Glu Glu Ala Arg Leu Arg Gly Thr His Gln Ala Leu
145                 150                 155                 160

Thr Pro Val Leu Asp Val Ala Arg Asp Pro Arg Trp Gly Arg Val Glu
                165                 170                 175

Glu Thr Phe Gly Glu Asp Pro Tyr Leu Val Ala Gln Met Gly Ile Ala
            180                 185                 190

Ala Val Arg Gly Phe Gln Gly Asp Arg Thr Phe Arg Asp Arg Lys His
        195                 200                 205

Leu Ile Ala Thr Leu Lys His Phe Ala Ala His Gly Gln Pro Glu Ser
    210                 215                 220

Gly Met Asn Cys Ala Pro Ala Asn Val Ser Met Arg Val Leu Arg Glu
225                 230                 235                 240

Thr Phe Leu Tyr Pro Phe Arg Gln Ala Ile Arg Glu Ala Gly Ala Ile
                245                 250                 255

Ser Val Met Ala Ser Tyr Asn Glu Ile Asp Gly Val Pro Ser His Ala
            260                 265                 270

Asn Arg Trp Leu Leu Arg Asp Val Leu Arg Lys Glu Trp Gly Phe Asp
        275                 280                 285

Gly Phe Val Val Ser Asp Tyr Tyr Ala Ile Trp Glu Leu Ser Glu Arg
    290                 295                 300

Pro Asp Thr His Gly His Phe Val Ala Ala Asp Lys Arg Glu Ala Cys
305                 310                 315                 320

Ala Leu Ala Val Arg Ala Gly Val Asn Ile Glu Leu Pro Glu Pro Asp
                325                 330                 335

Cys Tyr Leu His Leu Val Asp Leu Val Arg Glu Gly Val Leu Ser Glu
            340                 345                 350

Ala Glu Leu Asp Glu Leu Val Ala Pro Ile Leu Leu Trp Lys Phe Arg
        355                 360                 365

Leu Gly Leu Phe Asp Asp Pro Tyr Val Asp Pro Glu Glu Ala Ala Arg
    370                 375                 380

Val Val Gly Cys Asp Ala Asn Arg Glu Leu Ala Leu Arg Ala Ala Arg
385                 390                 395                 400

Asp Ala Ile Thr Leu Leu Lys Asn Glu Asn Gly Leu Leu Pro Leu Asp
                405                 410                 415

Pro Asp Arg Ile Thr Thr Ile Ala Val Ile Gly Pro Asn Ala His Arg
            420                 425                 430

Val Leu Leu Gly Gly Tyr Ser Gly Val Pro Lys His Tyr Val Thr Val
        435                 440                 445

Leu Asp Gly Ile Arg Ala Arg Val Gly Asp Arg Val Glu Val Leu Tyr
    450                 455                 460

Ala Glu Gly Cys Lys Ile Thr Val Gly Gly Ser Trp Asn Gln Asp Glu
465                 470                 475                 480
```

```
Val Val Leu Pro Asp Pro Glu Glu Asp Arg Arg Gln Ile Gln Glu Ala
                485                 490                 495

Val Glu Val Ala Arg Arg Ala Asp Val Val Ile Leu Ala Ile Gly Glu
            500                 505                 510

Asn Glu Gln Val Ser Arg Glu Ala Trp Ser Arg Gln His Leu Gly Asp
        515                 520                 525

Arg Ala Ser Leu Asp Leu Val Gly Arg Gln Gln Glu Leu Ala Asp Ala
    530                 535                 540

Leu Leu Ala Thr Gly Lys Pro Val Val Val Leu Leu Phe Asn Gly Arg
545                 550                 555                 560

Pro Leu Ser Val Pro Ala Leu Ala Glu Arg Ala Pro Ala Leu Leu Glu
                565                 570                 575

Cys Trp Tyr Leu Gly Gln Glu Thr Gly Arg Ala Val Ala Glu Val Leu
            580                 585                 590

Phe Gly Asp His Asn Pro Gly Gly Lys Leu Pro Ile Thr Ile Pro Arg
        595                 600                 605

Ser Val Gly His Leu Pro Ala Tyr Tyr Asn Tyr Lys Pro Ser Ala Arg
    610                 615                 620

Arg Gly Tyr Leu Phe Asp Asp Val Ser Pro Leu Phe Pro Phe Gly Tyr
625                 630                 635                 640

Gly Leu Ser Tyr Thr Thr Phe Glu Ile Arg Asn Val Arg Leu Glu Asp
                645                 650                 655

Pro Val Ile Pro Thr Ser Gly Ser Thr Arg Val Leu Ala Asp Val Thr
            660                 665                 670

Asn Thr Gly Pro Arg Glu Gly Thr Glu Val Val Gln Leu Tyr Ile Arg
        675                 680                 685

Asp Arg Val Ser Ser Val Thr Arg Pro Val Lys Glu Leu Lys Gly Phe
    690                 695                 700

Val Lys Val Arg Leu Arg Pro Gly Glu Thr Arg Thr Val Ala Leu Asp
705                 710                 715                 720

Ile Thr Pro Glu Ser Leu Ala Phe Tyr Asn Ile Asp Met Glu Trp Val
                725                 730                 735

Val Glu Pro Gly Glu Phe Glu Ile Met Val Gly Thr Ser Ser Arg Asp
            740                 745                 750

Ser Asp Leu Thr Lys Val Val Leu Gln Val Arg Asp
        755                 760
```

<210> SEQ ID NO 12
<211> LENGTH: 774
<212> TYPE: PRT
<213> ORGANISM: Artificial Sequence
<220> FEATURE:
<223> OTHER INFORMATION: synthetic cellulase with ORF J16 encoding beta-glucosidase activity

<400> SEQUENCE: 12

```
Gln Glu Arg Pro Ala Tyr Leu Asp Pro Thr Leu Pro Ile Glu Val Arg
1               5                   10                  15

Val Glu Asp Leu Leu Gly Arg Met Thr Leu Glu Glu Lys Val Ala Gln
            20                  25                  30

Met Leu Ser Met Arg Gln Thr Lys Arg Leu Ile Val Asp Glu Gln Asn
        35                  40                  45

Arg Phe Asp Pro Ser Arg Ala Pro Glu Trp Phe Lys Leu Gly Ile Gly
    50                  55                  60

Arg Ile Glu Arg Pro Ser Glu Tyr Phe Gln Thr Ala Arg Glu Ala Ala
65                  70                  75                  80
```

```
Ala Phe Thr Asn Ala Ile Gln Arg Trp Val Arg Glu Asn Thr Arg Leu
                85                  90                  95

Gly Ile Pro Val Ile Phe His Glu Glu Ala Leu His Gly Leu Arg Ala
            100                 105                 110

Ala Glu Ala Thr Ser Tyr Pro Gln Ala Ile Ala Leu Ala Ser Thr Trp
        115                 120                 125

Asn Pro Ala Leu Val Glu Arg Val Tyr Gly Arg Ile Ala Arg Glu Val
    130                 135                 140

Arg Ala Arg Gly Val His Gln Val Leu Ala Pro Val Val Asp Val Gly
145                 150                 155                 160

Arg Glu Pro Arg Trp Gly Arg Ile Glu Glu Thr Phe Gly Glu Asp Pro
                165                 170                 175

Tyr Leu Val Ala Glu Met Gly Lys Ala Ala Val Trp Gly Leu Gln Gly
            180                 185                 190

Arg Arg Val Pro Pro Val Gly Pro Gly His Val Ile Ala Thr Leu Lys
        195                 200                 205

His Met Ala Gly His Gly Gln Pro Glu Ser Gly Ile Asn Val Ala Pro
    210                 215                 220

Val Phe Phe Gly Glu Arg His Leu Arg Glu Val Phe Leu Tyr Pro Phe
225                 230                 235                 240

Arg Glu Ala Val Glu Lys Ala His Ala Leu Ser Val Met Ala Ser Tyr
                245                 250                 255

Asn Glu Ile Asp Gly Ile Pro Ser His Ala Asn Ala Trp Met Leu Arg
            260                 265                 270

Asp Val Leu Arg Gly Glu Trp Gly Phe Arg Gly Val Ile Val Ser Asp
        275                 280                 285

Trp His Gly Ile Pro Gln Leu Ile Thr Arg His His Val Ala Glu Asn
    290                 295                 300

Leu Glu Glu Ala Ala Arg Leu Ala Leu Gln Ala Thr Val Asp Val Glu
305                 310                 315                 320

Leu Pro Asp Tyr Glu Ala Tyr Ala Thr Leu Val Asp Gln Val Arg Arg
                325                 330                 335

Glu Leu Ile Pro Glu Leu Ala Val Asp Glu Ala Val Arg Arg Leu Leu
            340                 345                 350

Trp Ala Lys Phe Ala Val Gly Leu Phe Asp Gly Glu Pro Tyr Val Asp
        355                 360                 365

Glu Ala Glu Ala Ser Arg Val Asn Ala Ser Glu Glu Asp Arg Ala Leu
    370                 375                 380

Ala Leu Glu Ala Ala Arg Glu Ala Ile Ile Leu Leu Lys Asn Asp Gly
385                 390                 395                 400

Leu Leu Pro Leu Glu Ala Gly Arg Leu Asp Arg Val Ala Val Ile Gly
                405                 410                 415

Pro His Ala Gly Glu Val Leu Leu Gly Gly Tyr Ser Gly Arg Pro Arg
            420                 425                 430

Tyr Thr Val Ser Ile Leu Glu Gly Leu Arg Glu Arg Leu Arg Gly Glu
        435                 440                 445

Ala Glu Val Leu Tyr Ala Glu Gly Val Arg Ile Thr Glu Asp Ser Val
    450                 455                 460

Phe Thr Asp Glu Pro Gln Pro His Phe Gly Gly Thr Trp Ala Gln Gln
465                 470                 475                 480

Arg Asn Ala Ala His Arg Val Val Phe Thr Pro Pro Glu Ala Asn Arg
                485                 490                 495
```

```
Ser Arg Ile Glu Glu Ala Val Ala Leu Ala Arg Thr Ser Asp Val Val
            500                 505                 510

Val Leu Val Val Gly Gly Asn Glu Gln Thr Ala Arg Glu Ala Tyr Ala
        515                 520                 525

Pro Tyr His Leu Gly Asp Arg Leu Ser Leu Arg Leu Pro Gly Gln Gln
    530                 535                 540

Glu Glu Leu Val Lys Ala Val Leu Ala Thr Gly Val Pro Val Val Leu
545                 550                 555                 560

Val Val Ile Gly Gly Gln Pro Tyr Val Ile Thr Glu Leu Val Asp Arg
                565                 570                 575

Val Gly Ala Ile Val Trp Gly Trp Tyr Leu Gly Gln Glu Thr Gly Arg
            580                 585                 590

Ala Val Ala Glu Val Leu Leu Gly Asp Tyr Asn Pro Ala Gly Arg Leu
        595                 600                 605

Pro Ile Thr Ile Pro Arg His Glu Gly Gln Leu Pro Ala Tyr Tyr Ser
    610                 615                 620

His Lys Pro Ser Lys Glu Leu Asp Tyr Val Asp Gly Pro Ser Arg Pro
625                 630                 635                 640

Leu Phe Pro Phe Gly Tyr Gly Leu Ser Tyr Thr Arg Phe Ala Tyr Arg
                645                 650                 655

Ser Val Arg Leu Glu Pro Asp Arg Val Gly Gly Cys Gly Val Val Arg
            660                 665                 670

Val Leu Val Glu Leu Glu Asn Val Gly Asp Arg Ala Gly Asp Glu Val
        675                 680                 685

Val Gln Val Tyr Val Arg Asp Arg Val Ser Ser Val Ala Arg Pro Val
    690                 695                 700

Lys Glu Leu Lys Gly Phe Arg Arg Val His Leu Gly Pro Gly Glu Arg
705                 710                 715                 720

Lys Val Val Glu Ile Glu Leu Gly Pro Glu Ala Phe Ala Phe Tyr Gly
                725                 730                 735

Leu Glu Met Glu Arg Val Val Glu Ala Gly Trp Phe Asp Val Leu Val
            740                 745                 750

Gly Gly Asn Ser Glu Glu Leu Ile Ser Val Pro Leu Glu Ile Thr Glu
        755                 760                 765

Gly Cys Asn Leu Gly Arg
    770


<210> SEQ ID NO 13
<211> LENGTH: 933
<212> TYPE: PRT
<213> ORGANISM: Artificial Sequence
<220> FEATURE:
<223> OTHER INFORMATION: synthetic cellulase with ORF J17 encoding beta-
      glucosidase activity

<400> SEQUENCE: 13

Leu Ser Gly Glu Ser Met Ile Gly Val Pro Leu Glu Gly Phe Ala Asp
1               5                   10                  15

Phe Cys Arg Lys Val Ala Ala Glu Gly Ala Val Leu Leu Lys Asn Asp
            20                  25                  30

Gly Gly Val Leu Pro Leu Ala Glu Gly Asp Arg Val Ser Val Phe Gly
        35                  40                  45

Arg Ile Gln Ile Asn Tyr Tyr Arg Ser Gly Thr Gly Ser Gly Gly Ser
    50                  55                  60

Val Asn Val Pro Tyr Thr Thr Asn Leu Leu Asp Gly Leu Arg Gly Lys
65                  70                  75                  80
```

```
Ala Lys Ile Arg Val Asn Glu Asp Leu Ala Arg Val Tyr Glu Lys Trp
                85                  90                  95

Val Lys Glu Asn Pro Phe Asp Asn Gly Gly Gly Gly Trp Ala Lys Glu
            100                 105                 110

Pro Trp His Gln Lys Glu Met Pro Leu Ser Asp Glu Leu Val Ala Asp
        115                 120                 125

Ala Arg Ser Lys Ser Asp Lys Ala Val Val Val Ile Gly Arg Thr Ala
    130                 135                 140

Gly Glu Asp Lys Asp Asn Ala Pro Ala Pro Gly Ser Trp Tyr Leu Thr
145                 150                 155                 160

Glu Glu Glu Met Ala Met Leu Glu Ala Val Thr Arg His Phe Asp Lys
                165                 170                 175

Thr Ile Val Val Leu Asn Val Ser Asn Ile Ile Asp Met Glu Trp Val
            180                 185                 190

Asn Asp Ser Arg Phe Val His Pro Ile Ser Ala Val Ile Tyr Ala Trp
        195                 200                 205

His Gly Gly Met Glu Gly Gly Asn Ala Ile Ala Asp Val Leu Ala Gly
    210                 215                 220

Asp Ala Ala Pro Ser Gly Lys Leu Thr Asp Thr Ile Ala Ile Ser Ile
225                 230                 235                 240

Gly Asp Tyr Pro Ser Thr Ala Asn Tyr Gly Gly Glu Glu Lys Asn Val
                245                 250                 255

Tyr Gln Glu Asp Ile Tyr Val Gly Tyr Arg Tyr Phe Glu Thr Phe Cys
            260                 265                 270

Pro Glu Lys Val Arg Tyr Pro Phe Gly Phe Gly Leu Ser Tyr Thr Asp
        275                 280                 285

Phe Ser Ile Asp Gly Leu Gln Ala Glu Ser Val Ile Lys Asp Gly Leu
    290                 295                 300

Pro Arg Ile Asp Val Arg Val Lys Val Thr Asn Ala Gly Arg Leu His
305                 310                 315                 320

Ala Gly Lys Glu Val Val Gln Val Tyr Val Glu Ala Pro Gln Gly Lys
                325                 330                 335

Leu Gly Lys Pro Ala Lys Ala Leu Ala Ala Phe Ala Lys Thr Arg Leu
            340                 345                 350

Leu Ala Pro Gly Glu Ser Glu Glu Leu Val Ile Thr Phe Pro Leu Ala
        355                 360                 365

Arg Ile Ala Ser Tyr Asp Asp Ala Gly Leu Thr Gly His Arg Ser Ala
    370                 375                 380

Tyr Val Leu Glu Glu Gly Thr Tyr Arg Ile His Ala Gly Thr Ser Val
385                 390                 395                 400

Arg His Thr Val Pro Val Pro Val Asp Gly Arg Asp Gly Phe Thr Leu
                405                 410                 415

Asp Arg Leu Leu Val Val Glu Gln Leu Glu Glu Ala Leu Ala Pro Lys
            420                 425                 430

Glu Ala Phe Arg Arg Met Lys Pro Gly Gly Arg Lys Pro Asp Gly Thr
        435                 440                 445

Tyr Glu Leu Ala Trp Glu Glu Thr Pro Thr Arg Thr Val Asp Pro Ala
    450                 455                 460

Arg Arg Ile Ala Asp Arg Leu Pro Pro Ala Ile Pro Gln Thr Gly Asp
465                 470                 475                 480

Arg Gly Tyr Thr Leu Lys Asp Val His Glu Gly Thr Ile Ser Met Glu
                485                 490                 495
```

-continued

```
Thr Phe Ile Ala Gln Leu Ser Asp Asp Asp Leu Ala Ala Ile Val Arg
            500                 505                 510

Gly Glu Gly Met Ser His Pro Leu Val Thr Pro Gly Thr Ala Ser Ala
        515                 520                 525

Phe Gly Gly Val Thr Glu Arg Leu Arg Lys Phe Gly Ile Pro Leu Gly
    530                 535                 540

Cys Ala Ala Asp Gly Pro Ser Gly Ile Arg Met Asp Ser Gly His Lys
545                 550                 555                 560

Ala Thr Gln Val Pro Ile Gly Thr Leu Leu Ala Ala Thr Trp Asp Pro
                565                 570                 575

Ala Leu Val Glu Glu Leu Tyr Val Leu Glu Gly Arg Glu Leu Val Arg
            580                 585                 590

Asn Arg Ile Asp Thr Leu Leu Gly Pro Gly Ile Asn Leu Arg Arg His
        595                 600                 605

Pro Leu Asn Gly Arg Asn Phe Glu Tyr Phe Ser Glu Asp Pro Leu Ile
    610                 615                 620

Thr Gly Ala Phe Ala Ala Ala Cys Val Arg Gly Ile Lys Arg Gly Gly
625                 630                 635                 640

Ser Thr Ala Thr Ile Lys His Phe Ala Cys Asn Asn Gln Glu Lys Asn
                645                 650                 655

Arg Thr Lys Val Asp Ala Val Val Ser Glu Arg Ala Leu Arg Glu Leu
            660                 665                 670

Tyr Leu Lys Gly Phe Glu Ile Ala Val Lys Glu Gly Gly Ala Asn Ala
        675                 680                 685

Val Met Thr Ala Tyr Asn Pro Val Asn Gly Phe Trp Thr Ala Ser Cys
    690                 695                 700

Tyr Asp Leu Asn Thr Thr Ile Leu Arg Gly Glu Trp Lys Phe Asp Gly
705                 710                 715                 720

Ile Val Met Thr Asp Trp Trp Ala Met Met Asn Asp Pro Val Val Gly
                725                 730                 735

Gly Glu Pro Ser Arg Thr Asn Thr Gly Ala Met Val Arg Ala Gln Asn
            740                 745                 750

Asp Leu Tyr Met Val Val Pro Ser Phe Gly Ala Glu Thr Asn Ala Met
        755                 760                 765

Glu Asp Asn Thr Leu Glu Cys Leu Ala Ala Gly Lys Leu Thr Arg Gly
    770                 775                 780

Glu Leu Gln Arg Ser Ala Met Asn Ile Cys Arg Phe Leu Met Gln Val
785                 790                 795                 800

Pro Ala Phe Phe Arg Lys Gln Asp Phe Glu Thr Glu Pro Ser Val Ala
                805                 810                 815

Ile Arg Pro Ala Ala Ala Ala Pro Glu Gly Gly Ala Arg Ile Val Glu
            820                 825                 830

Ile Gly Asp Glu Ala Phe Val Arg Pro Glu Asp Gly Ala Ala Val Val
        835                 840                 845

Leu His Val Arg Glu Gly Gly Ala Phe Arg Val Ala Gly Arg Phe Arg
    850                 855                 860

Ala Glu Gly Leu Tyr Val Ala Gln Arg Ser Thr Asn Val Leu Leu Asn
865                 870                 875                 880

Gly Glu Arg Leu Ala Thr Leu Ser Ser Asn Gly Thr Gln Asn Lys Trp
                885                 890                 895

Val Glu Arg Lys Leu Ala Arg Ala Glu Leu Glu Ala Gly Tyr Tyr Val
            900                 905                 910

Leu Thr Leu Glu His Val Lys Pro Gly Leu Gly Ile Asp Gly Ile Gly
```

```
        915                 920                 925

Phe Ser Arg Ile Arg
    930


<210> SEQ ID NO 14
<211> LENGTH: 425
<212> TYPE: PRT
<213> ORGANISM: Artificial Sequence
<220> FEATURE:
<223> OTHER INFORMATION: synthetic cellulase with ORF J18 encoding beta-
      glucosidase activity

<400> SEQUENCE: 14

Val Ala Thr Ser Ala Tyr Gln Ile Glu Gly Ala Thr Gln Glu Asp Gly
1               5                   10                  15

Arg Gly Pro Ser Ile Trp Asp Thr Phe Ala Arg Arg Pro Gly Ala Ile
            20                  25                  30

Arg Asp Gly Ser Thr Gly Glu Pro Ala Cys Asp His Tyr His Arg Tyr
        35                  40                  45

Glu Glu Asp Ile Ala Leu Met Gln Ser Leu Gly Val Gly Ala Tyr Arg
    50                  55                  60

Phe Ser Val Ala Trp Pro Arg Ile Leu Pro Glu Gly Arg Gly Arg Ile
65                  70                  75                  80

Asn Pro Lys Gly Leu Ala Phe Tyr Asp Arg Leu Val Asp Arg Leu Leu
                85                  90                  95

Ala Ala Gly Ile Thr Pro Phe Leu Thr Leu Tyr His Trp Asp Leu Pro
            100                 105                 110

Gln Ala Leu Glu Asp Arg Gly Gly Trp Arg Ser Arg Glu Thr Ala Phe
        115                 120                 125

Ala Phe Ala Glu Tyr Ala Glu Ala Val Ala Arg Ala Leu Ala Asp Arg
    130                 135                 140

Val Pro Phe Phe Ala Thr Leu Asn Glu Pro Trp Cys Ser Ala Phe Leu
145                 150                 155                 160

Gly His Trp Thr Gly Glu His Ala Pro Gly Leu Arg Asn Leu Glu Ala
                165                 170                 175

Ala Leu Arg Ala Ala His His Leu Leu Leu Gly His Gly Leu Ala Val
            180                 185                 190

Glu Ala Leu Arg Ala Ala Gly Thr Lys Arg Val Gly Ile Val Leu Asn
        195                 200                 205

Phe Ala Pro Val Tyr Gly Glu Asp Pro Glu Ala Val Asp Val Ala Asp
    210                 215                 220

Arg Tyr His Asn Arg Tyr Phe Leu Asp Pro Ile Leu Gly Arg Gly Tyr
225                 230                 235                 240

Pro Glu Ser Pro Phe Gln Asp Pro Pro Pro Ala Pro Ile Leu Ser Arg
                245                 250                 255

Asp Leu Glu Ala Ile Ala Arg Pro Leu Asp Phe Leu Gly Val Asn Tyr
            260                 265                 270

Tyr Ala Pro Val Arg Val Ala Pro Gly Thr Gly Pro Leu Pro Val Arg
        275                 280                 285

Tyr Leu Pro Pro Glu Gly Pro Val Thr Ala Met Gly Trp Glu Val Tyr
    290                 295                 300

Pro Glu Gly Leu Tyr His Leu Leu Lys Arg Leu Gly Arg Glu Val Pro
305                 310                 315                 320

Trp Pro Leu Tyr Ile Thr Glu Asn Gly Ala Ala Tyr Pro Asp Leu Trp
                325                 330                 335
```

```
Thr Gly Glu Ala Val Val Glu Asp Pro Glu Arg Val Ala Tyr Leu Glu
            340                 345                 350

Ala His Val Glu Ala Ala Leu Arg Ala Arg Glu Glu Gly Val Asp Leu
        355                 360                 365

Arg Gly Tyr Phe Val Trp Ser Leu Met Asp Asn Phe Glu Trp Ala Phe
    370                 375                 380

Gly Tyr Thr Arg Arg Phe Gly Leu Tyr Tyr Val Asp Phe Pro Ser Gln
385                 390                 395                 400

Arg Arg Ile Pro Lys Arg Ser Ala Leu Trp Tyr Arg Glu Arg Ile Ala
                405                 410                 415

Arg Ala Gln Thr Gly Gly Ser Ala Arg
            420                 425


<210> SEQ ID NO 15
<211> LENGTH: 452
<212> TYPE: PRT
<213> ORGANISM: Artificial Sequence
<220> FEATURE:
<223> OTHER INFORMATION: synthetic cellulase with ORF J19 encoding beta-
      glucosidase activity

<400> SEQUENCE: 15

Ser Ala Gln Ser Ser Pro Thr Trp Phe Leu Trp Gly Thr Ala Thr Ala
1               5                   10                  15

Ala Tyr Gln Ile Glu Gly Ala Val His Glu Asp Gly Arg Gly Pro Ser
            20                  25                  30

Ile Trp Asp Thr Phe Ser His Thr Pro Gly Lys Ala Phe Gln Gly Gln
        35                  40                  45

Thr Gly Asp Ile Ala Cys Asp His Tyr His Arg Trp Pro Gln Asp Ile
    50                  55                  60

Glu Leu Met Arg Gln Leu Gly Ala Gln Ala Tyr Arg Phe Ser Ile Ala
65                  70                  75                  80

Trp Pro Arg Ile Phe Pro Glu Gly Ser Gly Arg Val Asn Glu Arg Gly
                85                  90                  95

Leu Asp Phe Tyr Asp Arg Leu Val Asp Ala Leu Leu Glu Ala Ser Ile
            100                 105                 110

Val Pro Phe Val Thr Leu Tyr His Trp Asp Leu Pro Gln Ala Leu Gln
        115                 120                 125

Asp Arg Gly Gly Trp Ala Glu Arg Ala Thr Val Glu Ala Phe Val Thr
    130                 135                 140

Tyr Ala Glu Thr Val Ala Arg Arg Leu Gly Asp Arg Val Arg Tyr Trp
145                 150                 155                 160

Ile Thr His Asn Glu Pro Trp Val Val Ala Tyr Leu Gly His Tyr Leu
                165                 170                 175

Gly Val His Ala Pro Gly Ile Ser Asp Leu Ala Thr Ala Ile Arg Val
            180                 185                 190

Ser His His Leu Leu Val Ser His Gly Leu Ala Ala Arg Ala Ile Arg
        195                 200                 205

Ala Val Ala Pro His Ala Glu Val Gly Ile Thr Leu Asn Leu Ser Pro
    210                 215                 220

Val Val Pro Ala Ser Asp Ala Val Ala Asp Gln Ala Ala Ala Lys Ala
225                 230                 235                 240

Tyr Asp Gly Ile Leu Asn Arg Trp Phe Leu Asp Pro Leu Phe Gly Arg
                245                 250                 255

Gly Tyr Pro Ser Asp Thr Arg Arg Leu Leu Gly Ala Phe Tyr Asp Pro
            260                 265                 270
```

```
Pro Glu Ser Asp Cys Asp Thr Ile Ala Glu Pro Leu Asp Phe Leu Gly
        275                 280                 285

Val Asn Tyr Tyr Thr Pro Ala Phe Val Gly Ser Ala Ser Asp Gln Ser
    290                 295                 300

Ala Gly Ala Phe Gly Ile Arg Leu Leu Ser Pro Glu Glu Leu His Ala
305                 310                 315                 320

Arg Gly Tyr Glu Leu Thr Asp Met Gly Trp Ala Val Val Pro Asp Gly
                325                 330                 335

Leu Glu Gln Leu Leu Val His Leu His Arg Glu Tyr Arg Pro Arg Ala
            340                 345                 350

Ile Phe Ile Thr Glu Asn Gly Ala Ala Phe Pro Asp Glu Val Val Asp
        355                 360                 365

Gly Val Val Ala Asp Asp Arg Arg Ile Ala Tyr Leu Val Gly His Ile
    370                 375                 380

Ala Ala Val Gln Arg Ala Arg Glu Ala Gly Val Pro Val His Gly Tyr
385                 390                 395                 400

Phe Val Trp Ser Phe Leu Asp Asn Phe Glu Trp Ala His Gly Tyr Ser
                405                 410                 415

Lys Arg Phe Gly Ile Val Tyr Val Asp Tyr Ala Thr Leu Ala Arg Leu
            420                 425                 430

Pro Lys Ala Ser Phe His Trp Tyr Arg Gln Leu Ile Ala Asn Gly Gly
        435                 440                 445

Leu Pro Asp Arg
    450


<210> SEQ ID NO 16
<211> LENGTH: 539
<212> TYPE: PRT
<213> ORGANISM: Artificial Sequence
<220> FEATURE:
<223> OTHER INFORMATION: synthetic cellulase with ORF J24 encoding
      endoglucanase activity

<400> SEQUENCE: 16

Val Gln Asn Ala Arg Arg Ile Ala Val Asn Gln Ile Gly Tyr Pro Ala
1               5                   10                  15

Gly Ser Glu Lys Lys Ala Val Phe Trp Asp Glu Gly Glu Phe Glu Val
            20                  25                  30

Ile Asp Ala Ala Ser Gly Ala Val Val His Arg Gly Ala Thr Ser Ala
        35                  40                  45

Leu Arg Arg Asp Glu Ala Ser Gly Glu Ala Val Ala Phe Gly Asp Phe
    50                  55                  60

Thr Pro Leu Asp Ala Pro Gly Arg Tyr Phe Ile Arg His Val Arg Thr
65                  70                  75                  80

Gly Glu Arg Ser Ala Thr Phe Gly Ile Gly Pro Ser Leu Tyr Asp Asp
                85                  90                  95

Val His Arg Gly Ala Leu Lys Ala Phe Tyr Phe Phe Arg Cys Gly Met
            100                 105                 110

Glu Leu Ser Glu Pro Phe Ala Gly Pro Trp Thr His Lys Ala Cys His
        115                 120                 125

Leu Ser Asp Gly Ile Val Tyr Arg Glu Pro Asp Arg Arg Leu Ala Gly
    130                 135                 140

Arg Gly Gly Trp His Asp Ala Gly Asp Tyr Gly Lys Tyr Thr Val Pro
145                 150                 155                 160

Ala Ala Lys Ala Ala Ala Asp Leu Leu Leu Ala Cys Glu Cys Tyr Pro
```

-continued

```
                165                 170                 175

Gly Ala Phe Arg Lys Pro Val Pro Leu Pro Glu Thr Asp Gly Arg Thr
            180                 185                 190

Pro Asp Val Leu His Glu Val Arg Trp Glu Leu Glu Phe Leu Phe Arg
        195                 200                 205

Met Gln Asp Pro Ala Thr Gly Gly Ala Phe His Lys Leu Thr Thr Lys
    210                 215                 220

Gln Phe Pro Pro Leu Asp Leu Lys Pro Glu Asp Asp Leu Gly Asp Leu
225                 230                 235                 240

Tyr Phe Leu Pro Val Ser Pro Thr Ala Thr Ala Asp Phe Ala Ala Ile
                245                 250                 255

Met Ala Met Ala Ser Arg Val Tyr Arg Pro Phe Asp Ala Ala Phe Ala
            260                 265                 270

Asp Arg Cys Leu Ala Ala Ala Leu Arg Ala Trp Ala Trp Leu Glu Ala
        275                 280                 285

His Pro Asp Ala Pro His Phe Lys Asn Pro Ala Asp Val Leu Thr Gly
    290                 295                 300

Glu Tyr Gly Asp Asp Cys Gly Asp Asp Glu Arg Phe Trp Ala Ala Ala
305                 310                 315                 320

Glu Leu Tyr Arg Ala Thr Gly Glu Ala Arg Phe His Asp Glu Val Lys
                325                 330                 335

Arg Leu Ala Gly Leu Pro Phe Ser Lys Thr Glu Leu Gly Trp Ala Asp
            340                 345                 350

Val Gly Gly Tyr Gly Ser Ile Ala Tyr Leu Leu Met Asp Glu Ser Ala
        355                 360                 365

Ala Asp Pro Ala Leu Arg Ser Ala Leu Ala Ala Glu Trp Lys Ala Arg
    370                 375                 380

Ala Asp Arg Leu Ala Ala Ala Ala Gly Glu Ser Gly Phe Ala Val Ala
385                 390                 395                 400

Leu Ala Pro Gly Asp Tyr Val Trp Gly Ser Asn Met Leu Val Met Asn
                405                 410                 415

Arg Ala Met His Leu Leu Ile Ala His Arg Leu Phe Gly Asp Pro Ala
            420                 425                 430

His Glu Lys Ala Ala Leu Asp Gln Val His Tyr Leu Leu Gly Arg Asn
        435                 440                 445

Ala Leu Asp Ile Ser Phe Val Thr Gly Phe Gly Asp Arg His Val Arg
    450                 455                 460

His Pro His Tyr Arg Pro Gly Val Ala Asp Gly Val Glu Glu Pro Val
465                 470                 475                 480

Pro Gly Phe Val Ser Gly Gly Pro Asn Ala Gly Leu Gln Asp Glu Lys
                485                 490                 495

Ala Arg Glu Ala Leu Ala Gly Met Pro Pro Ala Arg Cys Phe Ile Asp
            500                 505                 510

His Gln Asp Ser Tyr Ser Thr Asn Glu Val Ala Ile Tyr Trp Asn Ser
        515                 520                 525

Pro Ala Val Phe Val Leu Ser His Trp Val Arg
    530                 535
```

<210> SEQ ID NO 17
<211> LENGTH: 260
<212> TYPE: PRT
<213> ORGANISM: Artificial Sequence
<220> FEATURE:
<223> OTHER INFORMATION: synthetic cellulase with ORF J25 encoding endoglucanase activity

```
<400> SEQUENCE: 17

Glu Ile Met Arg Ala Val Leu Val Leu Ser Leu Leu Trp Leu Ser Gly
1               5                   10                  15

Cys Asp Trp Leu Phe Pro Asp Gly Asp Asn Gly Lys Glu Pro Glu Pro
            20                  25                  30

Glu Pro Glu Pro Thr Val Glu Leu Cys Gly Arg Trp Asp Ala Arg Asp
        35                  40                  45

Val Ala Gly Gly Arg Tyr Arg Val Ile Asn Asn Val Trp Gly Ala Glu
    50                  55                  60

Thr Ala Gln Cys Ile Glu Val Gly Leu Glu Thr Gly Asn Phe Thr Ile
65                  70                  75                  80

Thr Arg Ala Asp His Asp Asn Gly Asn Asn Val Ala Ala Tyr Pro Ala
                85                  90                  95

Ile Tyr Phe Gly Cys His Trp Gly Ala Cys Thr Asn Asn Ser Gly Leu
            100                 105                 110

Pro Arg Arg Val Gln Glu Leu Ser Asp Val Arg Thr Ser Trp Thr Leu
        115                 120                 125

Thr Pro Ile Thr Thr Gly Arg Trp Asn Ala Ala Tyr Asp Ile Trp Phe
    130                 135                 140

Ser Pro Gly Thr Asn Ser Ser Asn Gly Tyr Ser Gly Gly Ala Glu Leu
145                 150                 155                 160

Met Ile Trp Leu Asn Trp Asn Gly Gly Val Met Pro Gly Gly Ser Arg
                165                 170                 175

Val Ala Thr Val Glu Leu Ala Gly Ala Thr Trp Glu Val Trp Tyr Ala
            180                 185                 190

Asp Trp Asp Trp Asn Tyr Ile Ala Tyr Arg Arg Thr Thr Pro Thr Thr
        195                 200                 205

Ser Val Ala Glu Leu Asp Leu Lys Val Phe Ile Asp Asp Ala Val Ala
    210                 215                 220

Arg Gly Tyr Ile Arg Pro Glu Trp Tyr Leu His Ala Val Glu Thr Gly
225                 230                 235                 240

Phe Glu Leu Trp Glu Gly Gly Ala Gly Leu Arg Ser Ala Asp Phe Ser
                245                 250                 255

Val Thr Val Gln
            260


<210> SEQ ID NO 18
<211> LENGTH: 260
<212> TYPE: PRT
<213> ORGANISM: Artificial Sequence
<220> FEATURE:
<223> OTHER INFORMATION: synthetic cellulase with ORF J26 encoding
      endoglucanase activity

<400> SEQUENCE: 18

Glu Thr Met Arg Ala Ile Leu Val Leu Ser Leu Leu Trp Leu Ser Gly
1               5                   10                  15

Cys Asp Trp Leu Phe Pro Asp Gly Asp Asn Gly Lys Glu Pro Glu Pro
            20                  25                  30

Glu Pro Glu Pro Thr Val Glu Leu Cys Gly Arg Trp Asp Ala Arg Asp
        35                  40                  45

Val Ala Gly Gly Arg Tyr Arg Val Ile Asn Asn Val Trp Gly Ala Glu
    50                  55                  60

Thr Ala Gln Cys Ile Glu Val Gly Leu Glu Thr Gly Asn Phe Thr Ile
65                  70                  75                  80
```

```
Thr Arg Ala Asp His Asp Asn Gly Asn Asp Val Ala Ala Tyr Pro Ala
                85                  90                  95

Ile Tyr Phe Gly Cys His Trp Gly Ala Cys Thr Asn Asn Ser Gly Leu
            100                 105                 110

Pro Arg Arg Val Gln Glu Leu Ser Asp Val Arg Thr Ser Trp Thr Leu
        115                 120                 125

Thr Pro Ile Thr Thr Gly Arg Trp Asn Ala Ala Tyr Asp Ile Trp Phe
    130                 135                 140

Ser Pro Val Thr Asn Ser Ser Asn Gly Tyr Ser Gly Gly Ala Glu Leu
145                 150                 155                 160

Met Ile Trp Leu Asn Trp Asn Gly Gly Val Met Pro Gly Gly Ser Arg
                165                 170                 175

Val Ala Thr Val Glu Leu Ala Gly Ala Thr Trp Glu Val Trp Tyr Ala
            180                 185                 190

Asp Trp Asp Trp Asn Tyr Ile Ala Tyr Arg Arg Thr Thr Pro Thr Thr
        195                 200                 205

Ser Val Ser Glu Leu Asp Leu Lys Ala Phe Ile Asp Asp Ala Val Ala
    210                 215                 220

Arg Gly Tyr Ile Arg Pro Glu Trp Tyr Leu His Ala Val Glu Thr Gly
225                 230                 235                 240

Phe Glu Leu Trp Glu Gly Gly Ala Gly Leu Arg Ser Ala Asp Phe Ser
                245                 250                 255

Val Thr Val Gln
            260


<210> SEQ ID NO 19
<211> LENGTH: 614
<212> TYPE: PRT
<213> ORGANISM: Artificial Sequence
<220> FEATURE:
<223> OTHER INFORMATION: synthetic cellulase with ORF J29 encoding
      endoglucanase activity

<400> SEQUENCE: 19

Asn Glu Thr Ala Gly Thr Glu Val Pro Asp Ser Pro Met Gln Arg Leu
1               5                   10                  15

Val Asp Ala Met Gln Pro Gly Trp Asn Leu Gly Asn Thr Phe Asp Ala
            20                  25                  30

Thr Asp Gly Asp Glu Thr Ser Trp Gly Asn Pro Lys Val Thr Arg Glu
        35                  40                  45

Leu Ile Arg Ala Ile Arg Ala Gln Gly Tyr Asn Ser Ile Arg Ile Pro
    50                  55                  60

Val Thr Trp Asn His Arg Met Gly Pro Gly Pro Asp Tyr Glu Ile Arg
65                  70                  75                  80

Glu Ala Phe Met Glu Arg Ile Gln Glu Val Val Asp Trp Cys Leu Glu
                85                  90                  95

Ala Gly Phe Ile Val Ile Ile Asn Met His His Asp Ser Arg Trp Met
            100                 105                 110

His Asn Met Glu Asn Glu Arg Glu Glu Val Leu Ala Lys Phe Arg Ala
        115                 120                 125

Ala Trp Lys Gln Ile Ala Arg His Phe Arg Asp Tyr Asp Pro Glu Arg
    130                 135                 140

Leu Leu Phe Glu Gly Ile Asn Glu Pro Arg Phe Ser Glu Asp Trp Asn
145                 150                 155                 160

Glu Asp Arg Pro Ile Tyr Phe Gln Met Val Asp Glu Leu Gln Thr Ala
```

```
                165                 170                 175

Phe His Glu Thr Val Arg Glu Ser Gly Gly Lys Asn Gly Val Arg Pro
            180                 185                 190

Leu Val Leu Thr Thr Leu Thr Gly Gly His Ala Gln Ala Arg Leu Asp
        195                 200                 205

Ala Leu Tyr Glu Thr Ile Arg Lys Leu Asp Asp Pro Asn Val Ile Ala
    210                 215                 220

Thr Val His Tyr Tyr Gly Tyr Tyr Pro Phe Ser Val Asn Met Ala Gly
225                 230                 235                 240

Ala Thr Thr Phe Gly Glu Thr Ala Arg Lys Asp Val Ile His Asn Leu
                245                 250                 255

Gly Arg Val His Asp Thr Phe Thr Ala Arg Gly Ile Pro Val Ile Ile
            260                 265                 270

Gly Glu Phe Gly Leu Leu Gly Phe Asp Lys Tyr Val Glu Thr Ile Gln
        275                 280                 285

His Gly Glu Val Leu Lys Tyr Leu Glu Phe Val Thr His Phe Ala Arg
    290                 295                 300

Glu Lys Arg Met Ala His Met Leu Trp Asp Asn Gly Gln His Phe Asn
305                 310                 315                 320

Arg Lys Glu Leu Arg Trp Asn Asn Pro Asp Phe His Ala Ile Met Met
                325                 330                 335

Ser Thr Leu Thr Gly Arg Ser Ser Tyr Thr Glu Arg Asp Ser Val Tyr
            340                 345                 350

Ile Arg Lys Gly Glu Asp Val Arg Asp Val Ser Met Arg Leu Tyr Leu
        355                 360                 365

Asn Gly Asn Glu Leu Thr Gly Val Arg Ala Gly Asp Arg Ala Leu Ala
    370                 375                 380

Pro Gly Ala Asp Tyr Glu Ala Asp Gly Glu Gln Leu Val Leu Lys Ala
385                 390                 395                 400

Gly Leu Leu Lys Ser Leu Leu Gly Asp Gly Leu Gly Pro Gln Ala Asp
                405                 410                 415

Leu Thr Leu Ser Phe Ser Ala Gly Ala Asp Trp Val Ile His Val Ile
            420                 425                 430

Gln Tyr Glu Thr Pro Glu Leu Lys Asp Ser Lys Met Ser Arg Ala Asn
        435                 440                 445

Phe Ala Ile Pro Ala Lys Phe Lys Gly Asp Arg Leu Ala Thr Met Glu
    450                 455                 460

Ala Leu Tyr Val Gly Gly Gly Ile Ala Gly Pro Asp Asp Trp Thr Pro
465                 470                 475                 480

Phe Lys Glu Phe Gly Lys Ser Phe Asp Pro Asp Tyr Thr Tyr Gly Leu
                485                 490                 495

Ile Arg Ile Lys Gln Glu Phe Phe Asn Asp Val Lys Asp Gly Asp Ile
            500                 505                 510

Lys Leu Thr Phe His Phe Trp Ser Gly Thr Lys Leu Asp Tyr Leu Leu
        515                 520                 525

Thr Val Ser Gly Gly Glu Val Val Gly Lys Ala Pro Ala Pro Glu Gly
    530                 535                 540

Glu Glu Ala Ser Asp Glu Gly Gly Gly Gly Asp Pro Ala Asp Ala Ala
545                 550                 555                 560

Glu Thr Ala Ala Pro Ala Asp Gly Gly Gly Thr Ala Asp Gly Ala Val
                565                 570                 575

Pro Ala Asp Ala Ser Pro Gln Gly Ala Ser Asn Arg Thr Leu Phe Trp
            580                 585                 590
```

```
Gly Val Leu Val Ile Ala Ala Leu Ala Ala Leu Val Gly Leu Met Val
        595                 600                 605

Phe Arg Ser Val Lys Gly
    610


<210> SEQ ID NO 20
<211> LENGTH: 542
<212> TYPE: PRT
<213> ORGANISM: Artificial Sequence
<220> FEATURE:
<223> OTHER INFORMATION: synthetic cellulase with ORF J30 encoding
      endoglucanase activity

<400> SEQUENCE: 20

Leu Pro Glu Phe Pro Lys Ile Ala Val Val Ala Gly Ser Glu Ala Glu
1               5                   10                  15

Ser Val Phe Arg Val Val Asp Ile Gly Thr Gly Asp Val Val Tyr Glu
            20                  25                  30

Gly Arg Leu Ser Asp Ser Val Tyr Asp Asp Ala Ser Gly Asp Thr Val
        35                  40                  45

Arg His Ala Asp Phe Gly Glu Trp Lys Arg Pro Gly Ser Tyr Ser Val
    50                  55                  60

Thr Val Gly Arg Ser Ser Ser Ala Pro Phe Arg Ile Gly Asn Asp Val
65                  70                  75                  80

Tyr Arg Ala Pro Leu Ile Gln Ala Ala Arg Ser Tyr Thr Leu Ala Arg
                85                  90                  95

Ala Gly Val Ala Ile Asp Asp Pro Val Thr Gly Leu Arg His Asp Val
            100                 105                 110

Gly His Ala Gln Asp Lys Gln Ala Met Leu Phe Phe Glu Asp Pro Phe
        115                 120                 125

His Arg Gln Gly Asp Pro Ile Asp Val Ser Gly Gly Trp Tyr Asp Ala
    130                 135                 140

Gly Asp Tyr Gly Lys Tyr Val Pro Thr Gly Ala Val Ala Ala Ala Gln
145                 150                 155                 160

Leu Met Leu Ala Trp Glu Met Arg Pro Glu Leu Trp Arg Ser Leu Ser
                165                 170                 175

Leu Ser Leu Pro Ala Gly Leu Ser Glu Pro Glu Arg Arg Ala Gly Leu
            180                 185                 190

Pro Asp Leu Leu Val Glu Ile Lys Tyr Glu Leu Asp Trp Leu Leu Arg
        195                 200                 205

Met Gln Arg Pro Asp Gly Ala Val Tyr Leu Lys Val Ala Gly Gly Ala
    210                 215                 220

Trp Pro Gly Tyr Ile Arg Pro Glu Glu Asp Thr Ala Asp Arg Tyr Val
225                 230                 235                 240

Phe Gly Leu Ser Thr Tyr Gly Thr Ala Gln Phe Ala Gly Ala Ala Ala
                245                 250                 255

Met Gly Ala Arg Val Tyr Ala Pro Phe Leu Pro Asp Tyr Ala Arg Lys
            260                 265                 270

Leu Leu Asp Ala Ala Ile Arg Ala Gln Arg Tyr Leu Glu Gln His Pro
        275                 280                 285

Asp Pro Glu Phe Arg Tyr Asp Glu Gly Gln Asn Asn Gly Ser Gly Pro
    290                 295                 300

Tyr Glu Lys Arg Thr Asp Arg Glu Glu Arg Phe Trp Ala Ala Ala Glu
305                 310                 315                 320

Leu Leu Arg Thr Thr Asp Asp Ala Arg Tyr Asp Ala Tyr Ile Arg Glu
```

```
                325                 330                 335

His Phe Ser Asp Phe Leu Glu Gly Lys Thr Ser Ala Val Phe Trp Gly
            340                 345                 350

Asn Thr Val Leu Leu Gly Gln Trp Ala Tyr Val Asn Ala Glu Arg Ala
        355                 360                 365

Asp Ala Asp His Lys Ala Ser Val Arg Ala Ser Leu Thr Ala Tyr Ala
    370                 375                 380

Asp Glu Leu Val Arg Trp Ala Ser Ala Asn Gly Tyr Arg Ser Val Leu
385                 390                 395                 400

Arg Pro Thr Asp Tyr Phe Trp Gly Ser Ala Arg Glu Ala Met Gly Arg
                405                 410                 415

Ala Gln Ala Leu Leu Leu Ala Asp Ala Val Ala Pro Asn Arg Ala Tyr
            420                 425                 430

Leu Glu Thr Ala Leu Asp Gln Ala His Trp Leu Phe Gly Arg Asn Ala
        435                 440                 445

Ala Gly Thr Ser Phe Met Thr Gly Ile Gly Met His Ser Pro Gln Lys
    450                 455                 460

Pro His His Arg Leu Val Ala Ser Thr Gln Thr Leu Ile Pro Gly Leu
465                 470                 475                 480

Val Val Gly Gly Pro Asn Ala Gln Gly Gly Asp Pro Ile Met Asp Arg
                485                 490                 495

Leu Leu Arg Glu Ser Asp Pro Arg Val Phe Pro Ala Lys Ala Tyr Val
            500                 505                 510

Asp Asp Trp Glu Ala Tyr Ser Val Asn Glu Pro Ala Ile Asp Tyr Thr
        515                 520                 525

Ala Pro Ala Val Phe Val Leu Thr Arg Phe Ala Glu Asp Arg
    530                 535                 540
```

<210> SEQ ID NO 21
<211> LENGTH: 341
<212> TYPE: PRT
<213> ORGANISM: Artificial Sequence
<220> FEATURE:
<223> OTHER INFORMATION: synthetic cellulase with ORF J36 encoding endoglucanase activity

<400> SEQUENCE: 21

```
Gln Pro Gln Lys Asp Asn Phe Tyr Asp Asp Arg Ile Asp Thr Thr Ala
1               5                   10                  15

Lys Ala Pro Pro Lys Glu Thr Pro Arg Thr Tyr Ser Leu Pro Phe Ile
            20                  25                  30

Arg Val Glu Gly Asn Arg Phe Val Asp Glu Gln Gly Arg Thr Val Val
        35                  40                  45

Phe Arg Gly Val Ser Ile Ala Asp Pro Asp Arg Leu Glu Arg Leu Gly
    50                  55                  60

Arg Trp Ser Arg Arg Ile Phe Glu Val Leu Lys Asn Asp Trp Asn Ala
65                  70                  75                  80

Asn Ile Val Arg Ile Pro Val His Pro Arg Ala Trp Arg Ala Arg Gly
                85                  90                  95

Glu Glu Ala Tyr Leu Lys Leu Leu Asp Gln Ala Val Glu Trp Ala Asn
            100                 105                 110

Glu Leu Gly Leu Tyr Leu Ile Ile Asp Trp His Ser Ile Gly Asn Leu
        115                 120                 125

Arg Thr Glu Leu Phe Gln His Pro Met Tyr Asn Thr Thr Lys Thr Glu
    130                 135                 140
```

```
Thr Phe Arg Phe Trp Lys Thr Ile Ala Glu His Phe Arg His Asn Pro
145                 150                 155                 160

Ile Val Ala Phe Tyr Glu Val Phe Asn Glu Pro Thr Arg Phe Asn Gly
                165                 170                 175

Thr Leu Gly Arg Met Ser Trp Glu Glu Tyr Lys Gln Ile Val Glu Asp
            180                 185                 190

Ile Ile Tyr Ile Ile Tyr Ala His Asp Arg Thr Val Ile Pro Leu Val
        195                 200                 205

Gly Gly Phe Asp Trp Ala Tyr Asp Leu Thr Tyr Val Arg Glu Ser Pro
    210                 215                 220

Ile Ala Phe Pro Gly Ile Ala Tyr Thr Ala His Pro Tyr Pro Gln Lys
225                 230                 235                 240

Arg Gln Pro Pro Trp Glu Glu Lys Trp Glu His Asp Trp Gly Phe Val
                245                 250                 255

Ala Asp Thr Tyr Pro Val Phe Val Thr Glu Leu Gly Phe Met Ser Ala
            260                 265                 270

Asp Glu Pro Gly Ala His Val Pro Val Ile Gly Asp Glu Thr Tyr Gly
        275                 280                 285

Glu Ala Ile Ile Asn Tyr Met Glu Lys Lys Gly Ile Ser Trp Thr Ala
    290                 295                 300

Trp Val Phe Asp Pro Val Trp Ser Pro Gln Leu Ile Lys Asn Trp Asp
305                 310                 315                 320

Phe Glu Pro Thr Thr Gln Gly Arg Phe Phe Arg Glu Lys Met Arg Gln
                325                 330                 335

Leu Asn Pro Arg Asn
            340
```

<210> SEQ ID NO 22
<211> LENGTH: 445
<212> TYPE: PRT
<213> ORGANISM: Artificial Sequence
<220> FEATURE:
<223> OTHER INFORMATION: synthetic cellulase with ORF J27 encoding endoglucanase activity

<400> SEQUENCE: 22

```
Ala Lys Pro Gly Val Val Ala Asp Leu Thr Trp Tyr Ile Pro Asp Thr
1               5                   10                  15

Asp Lys Ala Arg Ser Ala Gln Ala Leu Arg Glu Leu Gly Ser Arg Trp
            20                  25                  30

Val Arg Leu His Val Gln Trp Arg Glu Ala Glu Pro Gln Pro Gly Val
        35                  40                  45

Phe Asp Glu Trp Trp Met Ser Glu Tyr Gly Arg Ala Leu Ser Ala Ala
    50                  55                  60

Arg Ala Ala Gly Gln Lys Val Ile Val Met Leu Ser Glu Ala Pro Thr
65                  70                  75                  80

Trp Ala Arg Val Ala Gln Gly Ser Ala Pro Arg Asp Pro Met Leu Phe
                85                  90                  95

Ala Gly Phe Leu Glu Arg Phe Ala Ala Arg Phe Arg Gly Arg Val Asp
            100                 105                 110

Ala Tyr Glu Ile Trp Asn Glu Pro Asn Ile Ala Arg Phe Trp Gly Pro
        115                 120                 125

Arg Pro Asp Pro Ala Ala Tyr Thr Glu Leu Leu Gly Ala Ala His Gly
    130                 135                 140

Ala Leu Arg Arg Ala Asp Pro His Ala Arg Val Val Phe Gly Gly Leu
145                 150                 155                 160
```

```
Ser Gly Asn Asp Trp Arg Phe Leu Glu Ala Ala Tyr Ser Ala Gly Ala
                165                 170                 175

Lys Gly Arg Phe Asp Val Leu Ala Ala His Pro Tyr Pro Tyr Cys Gly
            180                 185                 190

Ala Ser Gly Pro Gly Arg Ser Arg Arg Ser Gly Gly Arg Ile Thr Ala
        195                 200                 205

Asp Ser Phe Thr Gly Tyr Arg Glu Leu Arg Ala Ser Met Leu Ala Arg
    210                 215                 220

Gly Asp Ala Lys Pro Ile Trp Phe Thr Glu Phe Gly Trp Asn Thr Ser
225                 230                 235                 240

Thr Val Lys Cys Asn Pro Gly Ser Gly Gln Trp Gln Gly Gly Val Ser
                245                 250                 255

Glu Glu Arg Gln Ala Leu Tyr Leu Arg Arg Ala Phe Lys Leu Val Glu
            260                 265                 270

Arg Asp Arg Tyr Val Lys Val Ala Ile Trp Tyr Asn Leu Arg Asp Asn
        275                 280                 285

Trp Trp Gln Arg Gly Ala Asp Glu Pro Glu Ala Arg Phe Gly Leu Leu
    290                 295                 300

Arg Ala Asp Tyr Ser Arg Lys Pro Ala Phe Tyr Ala Phe Lys Ala Tyr
305                 310                 315                 320

Ala Arg Pro Lys Leu Arg Pro Arg Ala Thr Thr Val Thr Val Ala Leu
                325                 330                 335

Ala Pro Arg Pro Ala Ala Gly Arg Gly Val Arg Ile Glu Gly Ala Val
            340                 345                 350

Arg Gly Ala Asp Ala Gly Arg Val Arg Ile Ala Val Lys Arg Trp Ala
        355                 360                 365

Gly Lys Gly Trp Arg Leu Trp Gln Arg Arg Ser Ala Arg Leu Asp Ser
    370                 375                 380

Glu Gly Arg Tyr Arg Val Pro Leu Lys Pro Leu Gly Pro Gly Arg Tyr
385                 390                 395                 400

Arg Ala Arg Ala Arg Tyr Leu Gly Thr Asp Leu His Arg Pro Ser Ala
                405                 410                 415

Ser Arg Trp Arg Ser Trp Arg Val Ala Pro Thr Arg Pro Ala Ser Ala
            420                 425                 430

Gly Asp Gly Ala Leu Gly Ala Arg Ala Arg Pro Gly Ser
        435                 440                 445


<210> SEQ ID NO 23
<211> LENGTH: 330
<212> TYPE: PRT
<213> ORGANISM: Artificial Sequence
<220> FEATURE:
<223> OTHER INFORMATION: synthetic cellulase with ORF J28 encoding
      endoglucanase activity

<400> SEQUENCE: 23

Ala Phe Glu Ile His Arg Gly Thr Asn Ile Ser His Trp Leu Ser Gln
1               5                   10                  15

Ser Ser Ala Arg Gly Glu Glu Arg Arg Arg Trp Phe Thr Arg Glu Asp
            20                  25                  30

Val Glu Arg Ile Ala Gly Met Gly Leu Asp His Val Arg Leu Pro Val
        35                  40                  45

Asp Glu Glu Gln Leu Trp Asp Glu His Gly Arg Arg Asp Pro Glu Ala
    50                  55                  60

Phe Glu Leu Leu Gly Asn Ala Leu Glu Trp Cys Ala Glu Ala Gly Leu
```

```
65                  70                  75                  80

Arg Val Val Val Asp Leu His Ile Leu Arg Thr His His Phe Asn Asp
                85                  90                  95

Arg Gln Thr Pro Arg Leu Phe Thr Asp Pro Asp Glu Ala Thr Arg Phe
            100                 105                 110

Ala Gly Leu Trp Arg Asp Leu Ser Asp Phe Leu Arg Ala Trp Asp Val
        115                 120                 125

Asn His Val Ala Tyr Glu Leu Leu Asn Glu Pro Val Ala Arg Asp Pro
    130                 135                 140

Glu Arg Trp His Ala Val Ala Phe Val Ala Phe Ser Ala Ile Arg Glu
145                 150                 155                 160

Val Glu Pro Ala Arg Thr Ile Val Leu Gly Ser Asn Trp Phe Asn Ser
                165                 170                 175

Thr Glu Gln Phe Gly Val Leu Arg Val Pro Asp Asp Pro His Cys Ile
            180                 185                 190

Leu Thr Phe His Tyr Tyr Lys Pro Met Phe Ile Thr His Tyr Arg Ala
        195                 200                 205

Ser Trp Trp Pro Gly Gly Arg Tyr Gly Gly Arg Val Arg Tyr Pro Gly
    210                 215                 220

Arg Pro Val Pro Glu Glu Glu Leu Glu Gly Leu Ser Asp Glu Asp Arg
225                 230                 235                 240

Arg Leu Val Glu Ala Ala Asn Ala Pro Tyr Asp Arg Gly Val Met Ala
                245                 250                 255

Ser Glu Ile Ala Leu Pro Val Arg Val Ala Arg Glu His Gly Met Arg
            260                 265                 270

Leu Tyr Cys Gly Glu Phe Gly Val Tyr His Arg Thr Pro Arg Glu Tyr
        275                 280                 285

Arg Leu Ala Trp Tyr Arg Asp Leu Leu Ser Val Leu Arg Glu His Asp
    290                 295                 300

Ile Ala Trp Ala Asn Trp Asp Tyr Lys Gly Glu Gly Phe Gly Ile Val
305                 310                 315                 320

Thr Ala Glu Arg Arg Pro Thr Asp Ile Ala
                325                 330


<210> SEQ ID NO 24
<211> LENGTH: 490
<212> TYPE: PRT
<213> ORGANISM: Artificial Sequence
<220> FEATURE:
<223> OTHER INFORMATION: synthetic cellulase with ORF J31 encoding
      endoglucanase activity

<400> SEQUENCE: 24

Glu Thr Leu Glu Phe Leu Glu Val Arg Asn Gly Lys Ile Val Gly Ala
1               5                   10                  15

Arg Ser Gly Arg Glu Ile Arg Leu Arg Gly Thr Asn Ile Gly Gly Trp
            20                  25                  30

Leu Asn Met Glu Asn Phe Ile Asn Gly Tyr Ala Gly Thr Asp Gln Thr
        35                  40                  45

Val Arg His Ala Met Lys Glu Ala Leu Gly Glu Ala Lys Ala His Phe
    50                  55                  60

Phe Phe Glu Arg Met Leu Asp Tyr Phe Phe Thr Glu Asp Asp Val Leu
65                  70                  75                  80

Phe Leu Lys Glu Asn Gly Leu Asn Cys Val Arg Leu Pro Val Asn Tyr
                85                  90                  95
```

```
Arg Arg Phe Glu Asp Asp Glu Arg Pro Tyr Val Tyr Lys Glu Glu Gly
            100                 105                 110

Phe Arg Arg Leu Asp Glu Ala Leu Arg Leu Cys Glu Lys Tyr Gly Ile
        115                 120                 125

Tyr Ala Ile Ile Asp Met His Ala Val Gln Gly Tyr Gln Asn Thr His
    130                 135                 140

Trp His Ser Asp Asn Ala Ser Arg His Ser Phe Phe Trp His Asp Ala
145                 150                 155                 160

Thr Cys Gln Gln Arg Phe Phe Ala Leu Trp Arg Ala Ile Ala Glu Arg
                165                 170                 175

Tyr Arg Asp Arg Ala Val Val Ala Gly Tyr Asp Leu Met Asn Glu Pro
            180                 185                 190

Cys Thr Asn Thr Pro Tyr Gly Asp Tyr Pro His Thr Phe Tyr Ala Asn
        195                 200                 205

Tyr Lys Pro Asp Trp Glu Arg Met Asn Arg Ile Tyr Arg Lys Ala Val
    210                 215                 220

Ala Glu Ile Arg Ser Val Asp Pro Gln His Ile Ile Phe Leu Glu Gly
225                 230                 235                 240

Asp Arg Tyr Ala Tyr Arg Phe Asp Gly Leu Glu Ala Pro Phe Ala Glu
                245                 250                 255

Asn Leu Ala Tyr Gln Ser His Asn Tyr His Ala Ala Gly Phe Gly Pro
            260                 265                 270

Gly Pro Tyr Pro Gly Val Ile Arg Pro Asn Asn Pro Asp Ala Val Gln
        275                 280                 285

Gly Val Tyr Trp Asp Met Glu Gln Gln Arg Lys Ala Phe Leu Glu His
    290                 295                 300

Glu Gly Thr Val Phe Ala Lys Lys His Asn Val Pro Leu Leu Val Gly
305                 310                 315                 320

Glu Phe Gly Ser Val Tyr Asn Gly Pro Ala Glu Glu Val Pro Asp Arg
                325                 330                 335

Leu Arg Ser Met Asp Asp Gln Ile Ala Val Phe Glu Glu Asn Gly Ala
            340                 345                 350

His Trp Thr Thr Trp Thr Tyr Lys Asp Val Gly Val Met Gly Leu Val
        355                 360                 365

Thr Leu Asp Pro Glu Ser Glu Tyr Met Gln Arg Ile Ala Ser Phe Leu
    370                 375                 380

Glu Lys Lys Tyr Arg Leu Gly Thr Asp Asp Trp Met His Trp Leu Pro
385                 390                 395                 400

Ala Ala Ala Ala Arg Gln Leu Val Ser Gly Val Ala Glu Tyr Leu Arg
                405                 410                 415

Glu Thr Ile Asp Glu Ser Ile His Ser Gly Phe Asn Arg Arg Ala Leu
            420                 425                 430

Met Gln His Val Leu Cys Val Tyr Ala Ala Thr Leu Leu Glu Pro Glu
        435                 440                 445

Tyr Ala Lys Val Phe Lys Gly Leu Ser Glu Gln Gln Leu Asp Glu Ile
    450                 455                 460

Leu Gln Ser Phe Ser Phe Lys Gln Cys Val Val Asn Arg Asp Leu Ala
465                 470                 475                 480

Gly Ile Leu Arg Lys His Ala Gly Ala Glu
                485                 490
```

<210> SEQ ID NO 25
<211> LENGTH: 556
<212> TYPE: PRT

```
<213> ORGANISM: Artificial Sequence
<220> FEATURE:
<223> OTHER INFORMATION: synthetic cellulase with ORF J32 encoding
      endoglucanase activity

<400> SEQUENCE: 25

Ser Glu Asp Leu Gln Pro Ile Pro His Thr Asp Val Asn Pro Leu Gly
1               5                   10                  15

Val Asn Thr Leu Leu Asn Glu Glu Ala Asp Pro Glu Lys Val Glu Arg
            20                  25                  30

Thr Leu Asp Met Ile Ala Ala Gly Gly Phe Thr Phe Val Arg Gln Met
        35                  40                  45

Phe Ala Trp Tyr Glu Ile Glu Pro Ala Lys Gly Val Tyr Val Asp Pro
    50                  55                  60

His Thr Gly Gln Asp Thr Trp Glu Lys Tyr Asp Arg Ile Val Asn Leu
65                  70                  75                  80

Ala His Glu Arg Gly Leu Glu Ile Ile Ala Arg Leu Asp Lys Pro Pro
                85                  90                  95

Arg Trp Ala Arg Glu Gly Gln Pro Gly Val Asp Gln Val Pro Asp Gly
            100                 105                 110

Pro Pro Asn Asn Asp Ala Asp Tyr Ala Asp Phe Val Arg Ala Val Val
        115                 120                 125

Thr Arg Tyr Arg Gly Lys Val Arg Tyr Ile Gln Ile Trp Asn Glu Pro
    130                 135                 140

Asn Leu Tyr Gly Glu Trp Gly Gly Gln Pro Ile Asn Pro Ala Arg Phe
145                 150                 155                 160

Thr Glu Leu Leu Lys Ala Ala Tyr Thr Ala Ala Lys Glu Ala Asn Pro
                165                 170                 175

Glu Val Val Val Leu Leu Ala Gly Leu Ala Pro Thr Asp Gln Arg Gly
            180                 185                 190

Pro Glu Asn Leu Asn Glu Phe Leu Phe Leu Gln Gly Met Tyr Asp Ala
        195                 200                 205

Gly Ala Lys Asp Tyr Phe Asp Ile Ala Thr Ala Met Val Tyr Gly Tyr
    210                 215                 220

Gly Tyr Ser Pro Tyr Asp Arg Arg Val Glu Phe Glu Arg Asn Asn Phe
225                 230                 235                 240

Ser Arg Val Ile Gln Met Arg Glu Val Met Val Arg Asn Gly Asp Ala
                245                 250                 255

Asp Lys Pro Ile Trp Ala Ala Glu Tyr Gly Trp Val Ser Leu Pro Asp
            260                 265                 270

Asp Trp Thr Gly Asp Ala Ser Val Trp Gly Arg Pro Val Ser Ala Glu
        275                 280                 285

Thr Gln Ala Arg Tyr Leu Leu Gln Gly Tyr Leu Arg Ala Gln Arg Glu
    290                 295                 300

Trp Pro Trp Leu Gly Ala Met Cys Val Trp Leu Phe Arg Phe Pro Thr
305                 310                 315                 320

Ser Pro Thr Ala Thr Pro Asp Ala Gly Arg Asn Pro Thr Arg Gly Phe
                325                 330                 335

Ala Ile Val Asn Tyr Asp Phe Ser Pro Thr Pro Ala Tyr Thr Thr Leu
            340                 345                 350

Ala Gly Ser Arg Ala Arg Leu Asp Arg Ala Tyr Thr Gly Ala Tyr Pro
        355                 360                 365

Ala Ser Thr Arg Leu Ile Gln Gln Asp Gly Gly Trp Met Leu Thr Gly
    370                 375                 380
```

```
Glu Gly Ala Ser Gln Thr Leu Val Pro Ala Ala Ala Gly Ala Thr Leu
385                 390                 395                 400

Arg Ile Pro Phe Ser Gly Pro Arg Leu Asp Leu Leu Leu Asp Gly Ser
                405                 410                 415

Gly Gln Gly Leu Met Val Thr Ile Asp Gly Lys Pro Ala Pro Gly Leu
            420                 425                 430

Pro Ala Glu Glu Thr Gly Ala Ala Ile Ala Val Pro Asp Glu Asp Gly
        435                 440                 445

Arg Val Thr Val Ala Asp Gly Leu Asp Asp Gly Pro His Val Ala Glu
    450                 455                 460

Val Arg Ser Leu Ala Gly Gly Asp Gly Ser Val Ala Leu Ala Gly Phe
465                 470                 475                 480

Val Val Val Arg Gln Pro Trp Gln Ser Trp Ala Tyr Pro Trp Ile Tyr
                485                 490                 495

Gly Thr Phe Ala Val Met Val Val Leu Thr Leu Ala Ser Leu Val Trp
            500                 505                 510

Asn Trp Arg Tyr Arg Pro Ala Glu Ser Pro His Pro Thr Arg Asp Gly
        515                 520                 525

Ala Asn Gly His Leu Pro Arg Arg Leu Thr Ala Ala Asp Leu Arg Ala
    530                 535                 540

Arg Ser Arg Thr Arg Gln Ser Thr Thr Arg Arg Arg
545                 550                 555


<210> SEQ ID NO 26
<211> LENGTH: 476
<212> TYPE: PRT
<213> ORGANISM: Artificial Sequence
<220> FEATURE:
<223> OTHER INFORMATION: synthetic cellulase with ORF J35 encoding
      endoglucanase activity

<400> SEQUENCE: 26

Glu Trp Leu Arg Leu Glu Gly Ala Arg Ile Val Arg Ala Ser Asp His
1               5                   10                  15

Ser Pro Phe Tyr Leu Arg Gly Ile Ala Val Gly Gly Trp Leu Asn Thr
            20                  25                  30

Glu Asn Phe Ile Asn Gly Tyr Ser Gly Asn Glu Ser Ser Trp Ala Glu
        35                  40                  45

Ala Leu Glu Glu Glu Leu Gly Ser Asp Ala Ala Glu Ala Phe Phe Gln
    50                  55                  60

Ala Ile Arg Glu His Phe Phe Ser Glu Glu Asp Val Ala Tyr Ile Arg
65                  70                  75                  80

Ser Leu Gly Ala Thr Ala Ile Arg Ile Pro Phe His Trp Arg Tyr Ala
                85                  90                  95

Asp Pro Ala Asn Val Thr Tyr Leu Asp Arg Val Val Glu Trp Ala Arg
            100                 105                 110

Arg Tyr Gly Val Tyr Val Ile Leu Asp Leu His Ala Val Pro Gly Trp
        115                 120                 125

Gln Asn Pro Gly Trp His Cys Asp Asn Pro Tyr Gly Val Ser Leu Phe
    130                 135                 140

Trp Arg Glu Thr Phe Tyr Gln Asp Gln Val Ile Ala Leu Trp Arg Phe
145                 150                 155                 160

Leu Ala Asp Arg Tyr Lys Asp Glu Pro Ala Ile Ala Gly Tyr Asp Leu
                165                 170                 175

Leu Asn Glu Pro Tyr Ala Pro Ser Asn Glu Leu Val Val Ser Phe Phe
            180                 185                 190
```

```
Glu Arg Leu Ile Arg Ala Ile Arg Glu Val Asp Arg Arg His Leu Leu
        195                 200                 205

Phe Val Glu Gly Asn Arg Tyr Ala Arg Asp Phe Glu Gly Phe Glu Arg
    210                 215                 220

Leu Leu Glu Val Asp Asp Gln Ile Val Phe Ser Ser His Asn Tyr Met
225                 230                 235                 240

Thr Pro Thr His Glu Gly Ser Ser Phe Pro Gly Trp Leu Glu Val Asp
                245                 250                 255

Gly Arg Arg Ile Trp Ile Asp Glu Ser Trp Ile Glu Ala His Tyr Arg
            260                 265                 270

Thr Thr Asn Ala Trp Phe Leu Glu Arg Asn Leu Ala Cys Tyr Val Gly
        275                 280                 285

Glu Phe Gly Ala Leu Tyr Asp Ala Pro Leu Asp Ala Pro Ser Ser Lys
    290                 295                 300

Asp Leu Ala Arg Leu Arg Ala Leu Glu Ala Gln Ile Ala Leu Phe Asn
305                 310                 315                 320

Lys Leu Gly Val His Trp Thr Leu Trp Thr Tyr Lys Asp Leu Gly Ala
                325                 330                 335

Gln Gly Val Arg Val Ile Asp Pro Asp Ser Ala Tyr Tyr Arg Arg Ile
            340                 345                 350

Lys Pro Phe Leu Thr Leu Lys Met Arg Leu Gly Val Glu Glu Trp Thr
        355                 360                 365

Ser Arg Gly Arg Gly Pro Leu Ala Arg Arg Ile Arg Ala Leu Leu Gln
    370                 375                 380

Glu Met Glu Glu Glu Val Val Arg Leu Leu Gln Asp Tyr Ala Leu Ala
385                 390                 395                 400

Lys Arg Gln Leu Glu Glu Ala Leu Leu Leu Ser Ala Leu Tyr Gly His
                405                 410                 415

Ile Ala Gly Ala Leu Asn Pro Leu Leu Ala Arg Leu Phe Ala Gly Leu
            420                 425                 430

Ser Ser Ser Glu Ile Tyr Glu Glu Val Lys Glu Gly Val Arg Phe Ser
        435                 440                 445

Arg Thr Lys Glu Arg Thr Val Leu Ala Glu Val Leu Arg Arg Gln Leu
    450                 455                 460

Ala Gly Gly Glu Glu Thr Lys Gly Gly Gly Glu Ala
465                 470                 475


<210> SEQ ID NO 27
<211> LENGTH: 15
<212> TYPE: PRT
<213> ORGANISM: Artificial Sequence
<220> FEATURE:
<223> OTHER INFORMATION: synthetic polypeptide insertion sequence

<400> SEQUENCE: 27

Ala Ala Ile Val Ile Thr Glu Asn Gly Ala Ala Tyr Pro Asp Glu
1               5                   10                  15


<210> SEQ ID NO 28
<211> LENGTH: 9
<212> TYPE: PRT
<213> ORGANISM: Artificial Sequence
<220> FEATURE:
<223> OTHER INFORMATION: synthetic polypeptide insertion sequence

<400> SEQUENCE: 28

Asn Ala Val Lys Val Thr Ala Ala Ala
```

```
1               5


<210> SEQ ID NO 29
<211> LENGTH: 251
<212> TYPE: DNA
<213> ORGANISM: Artificial Sequence
<220> FEATURE:
<223> OTHER INFORMATION: synthetic pUC57 T7, Gateway attB1/attB2 and His
      tag sequence

<400> SEQUENCE: 29

gaattctaaa ttaatacgac tcactatagg gagaccacaa cggtttccct ctagaaataa     60

ttttgtttaa ctttaagaag gagatataca tatgacaagt ttgtacaaaa aagcaggctt    120

cgctagccca atccaatctc gaggacccag ctttcttgta caaagtggtc catcatcacc    180

atcaccatta acaataacta gcataacccc ttggggcctc taaacgggtc ttgaggggtt    240

ttttggagct c                                                         251
```